US008849458B2

(12) United States Patent
Weinert et al.

(10) Patent No.: US 8,849,458 B2
(45) Date of Patent: Sep. 30, 2014

(54) COLLECTION DEVICE WITH SELECTIVE DISPLAY OF TEST RESULTS, METHOD AND COMPUTER PROGRAM PRODUCT THEREOF

(75) Inventors: Stefan Weinert, Pendleton, IN (US); Matthias Essenpreis, Weinheim (DE); Nigel Surridge, Carmel, IN (US); Remmert Laan, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/818,875

(22) Filed: Jun. 18, 2010

(65) Prior Publication Data

US 2011/0152656 A1     Jun. 23, 2011

Related U.S. Application Data

(63) Continuation-in-part of application No. 12/643,415, filed on Dec. 21, 2009.

(60) Provisional application No. 61/140,270, filed on Dec. 23, 2008.

(51) Int. Cl.
| | |
|---|---|
| G05B 21/00 | (2006.01) |
| G06F 19/00 | (2011.01) |
| G06Q 50/22 | (2012.01) |
| A61B 5/00 | (2006.01) |
| A61B 5/145 | (2006.01) |

(52) U.S. Cl.
CPC .......... *A61B 5/0002* (2013.01); *G06F 19/3406* (2013.01); *G06Q 50/22* (2013.01); *G06F 19/3418* (2013.01); *G06F 19/363* (2013.01); *A61B 5/14532* (2013.01)
USPC ............................... 700/266; 702/23; 702/19

(58) Field of Classification Search
USPC ............................................. 702/19; 700/266
See application file for complete search history.

(56) References Cited

U.S. PATENT DOCUMENTS

| | | | |
|---|---|---|---|
| 4,151,845 A | 5/1979 | Clemens | |
| 4,731,726 A | 3/1988 | Allen, III | |
| 4,803,625 A | 2/1989 | Fu et al. | |
| 5,364,346 A | 11/1994 | Schrezenmeir | |
| 5,377,258 A | 12/1994 | Bro | |
| 5,572,421 A | 11/1996 | Altman et al. | |
| 5,576,952 A | 11/1996 | Stutman et al. | |
| 5,665,065 A | 9/1997 | Colman et al. | |
| 5,722,418 A | 3/1998 | Bro | |
| 5,822,715 A | 10/1998 | Worthington et al. | |
| 5,840,020 A | 11/1998 | Heinonen et al. | |
| 5,868,669 A | 2/1999 | Iliff | |
| 5,879,163 A | 3/1999 | Brown et al. | |
| 5,897,493 A | 4/1999 | Brown | |
| 5,971,922 A | 10/1999 | Arita et al. | |
| 6,018,713 A | 1/2000 | Coli et al. | |
| 6,039,688 A | 3/2000 | Douglas et al. | |
| 6,108,665 A | 8/2000 | Bair et al. | |
| 6,234,964 B1 | 5/2001 | Iliff | |
| 6,241,633 B1 | 6/2001 | Conroy | |
| 6,269,314 B1 | 7/2001 | Itawaki et al. | |
| 6,326,160 B1 | 12/2001 | Dunn et al. | |
| 6,338,039 B1 | 1/2002 | Lonski et al. | |
| 6,352,505 B1 | 3/2002 | Bortz | |
| 6,379,301 B1 | 4/2002 | Worthington et al. | |
| 6,424,847 B1 | 7/2002 | Mastrototaro et al. | |
| 6,425,863 B1 | 7/2002 | Werner et al. | |
| 6,544,212 B2 | 4/2003 | Galley et al. | |
| 6,567,785 B2 | 5/2003 | Clendenon | |
| 6,575,900 B1 | 6/2003 | Zweig et al. | |
| 6,645,368 B1 | 11/2003 | Beaty et al. | |
| 6,656,114 B1 | 12/2003 | Poulsen et al. | |
| 6,691,043 B2 | 2/2004 | Ribeiro, Jr. | |
| 6,770,029 B2 | 8/2004 | Iliff | |
| 6,835,175 B1 | 12/2004 | Porumbescu | |
| 6,879,970 B2 | 4/2005 | Shiffman et al. | |
| 6,923,763 B1 | 8/2005 | Kovatchev et al. | |
| 6,954,662 B2 | 10/2005 | Freger et al. | |
| 7,179,226 B2 | 2/2007 | Crothall et al. | |

(Continued)

FOREIGN PATENT DOCUMENTS

| | | |
|---|---|---|
| DE | 102005041627 A1 | 3/2007 |
| EP | 1 702 559 A2 | 9/2006 |
| EP | 1 728 469 A2 | 12/2006 |
| EP | 1 956 508 A2 | 12/2007 |
| EP | 2006786 A1 | 12/2008 |
| WO | 94/20916 | 9/1994 |
| WO | 9901836 | 1/1999 |
| WO | 0009007 | 2/2000 |
| WO | 0122343 A2 | 3/2001 |
| WO | 0133314 A2 | 5/2001 |

(Continued)

OTHER PUBLICATIONS

Gerstein et al., "A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia Treatment) Study", Diabetic Medicine, vol. 23, pp. 736-742, 2006.

Hirsch et al., "A Real-World Approach to Insulin Therapy in Primary Care Practice", Practical Pointers, Clinical Diabetes, vol. 23, Nov. 2, 2005.

(Continued)

*Primary Examiner* — Natalia Levkovich
(74) *Attorney, Agent, or Firm* — Dinsmore & Shohl LLP

(57) ABSTRACT

A collection device with a selective display of test results and method thereof are disclosed. A structured collection procedure defining data collection times and the associated context of the collection also defines what information regarding the results of the collection may be viewable by a user performing the structured collection procedure on the device. In this manner, the patient can be monitored according to the structured collection procedure while preventing the patient from modifying his or her behavior based on collection results.

31 Claims, 19 Drawing Sheets

(56) References Cited

U.S. PATENT DOCUMENTS

| | | |
|---|---|---|
| 7,229,430 B2 | 6/2007 | Hickle et al. |
| 7,241,265 B2 | 7/2007 | Cummings et al. |
| 7,266,400 B2 | 9/2007 | Fine et al. |
| 7,278,983 B2 | 10/2007 | Ireland et al. |
| 7,381,523 B2 | 6/2008 | Efendic |
| 7,389,133 B1 | 6/2008 | Kotulla et al. |
| 7,404,796 B2 | 7/2008 | Ginsberg |
| 7,405,196 B2 | 7/2008 | Rosskamp et al. |
| 7,413,749 B2 | 8/2008 | Wright et al. |
| 7,415,447 B2 | 8/2008 | Shiffman et al. |
| 7,509,156 B2 | 3/2009 | Flanders |
| 7,523,040 B2 | 4/2009 | Kirchhoff et al. |
| 7,553,281 B2 | 6/2009 | Hellwig et al. |
| 7,685,000 B1 | 3/2010 | Petit et al. |
| 7,734,323 B2 | 6/2010 | Blomquist et al. |
| 7,761,310 B2 | 7/2010 | Rodgers |
| 7,766,830 B2 | 8/2010 | Fox et al. |
| 2002/0107476 A1 | 8/2002 | Mann et al. |
| 2002/0143563 A1 | 10/2002 | Hufford et al. |
| 2002/0161288 A1 | 10/2002 | Shin et al. |
| 2003/0028399 A1 | 2/2003 | Davis et al. |
| 2003/0104982 A1 | 6/2003 | Wittmann et al. |
| 2003/0130616 A1 | 7/2003 | Steil et al. |
| 2003/0208113 A1 | 11/2003 | Mault et al. |
| 2003/0211617 A1* | 11/2003 | Jones .......................... 436/14 |
| 2004/0122701 A1 | 6/2004 | Dahlin et al. |
| 2004/0122709 A1* | 6/2004 | Avinash et al. ................ 705/2 |
| 2004/0247748 A1 | 12/2004 | Bronkema |
| 2005/0016844 A1 | 1/2005 | Burke et al. |
| 2005/0020903 A1 | 1/2005 | Krishnan et al. |
| 2005/0021372 A1 | 1/2005 | Mikkelsen et al. |
| 2005/0049179 A1 | 3/2005 | Davidson et al. |
| 2005/0119540 A1 | 6/2005 | Potts et al. |
| 2005/0119788 A1 | 6/2005 | Engleson et al. |
| 2006/0010098 A1 | 1/2006 | Goodnow et al. |
| 2006/0025931 A1 | 2/2006 | Rosen et al. |
| 2006/0030890 A1 | 2/2006 | Cosentino et al. |
| 2006/0031094 A1 | 2/2006 | Cohen et al. |
| 2006/0171503 A1 | 8/2006 | O'Hara et al. |
| 2006/0173406 A1 | 8/2006 | Hayes et al. |
| 2006/0195022 A1 | 8/2006 | Trepagnier et al. |
| 2006/0195029 A1 | 8/2006 | Shults et al. |
| 2006/0195342 A1 | 8/2006 | Khan et al. |
| 2006/0253296 A1 | 11/2006 | Liisberg et al. |
| 2006/0271404 A1 | 11/2006 | Brown |
| 2006/0287883 A1 | 12/2006 | Turgiss et al. |
| 2007/0048691 A1 | 3/2007 | Brown |
| 2007/0055483 A1 | 3/2007 | Lee et al. |
| 2007/0100659 A1 | 5/2007 | Preiss |
| 2007/0106135 A1 | 5/2007 | Sloan et al. |
| 2007/0162304 A1 | 7/2007 | Rodgers |
| 2007/0198296 A1 | 8/2007 | Pellinat et al. |
| 2007/0213604 A1 | 9/2007 | Brown |
| 2007/0253904 A1 | 11/2007 | Gunton et al. |
| 2007/0282636 A1 | 12/2007 | Sauk et al. |
| 2008/0025591 A1 | 1/2008 | Bhanot et al. |
| 2008/0109043 A1 | 5/2008 | Salo et al. |
| 2008/0125636 A1 | 5/2008 | Ward et al. |
| 2008/0146895 A1 | 6/2008 | Olson et al. |
| 2008/0154513 A1 | 6/2008 | Kovatchev et al. |
| 2008/0172027 A1 | 7/2008 | Blomquist |
| 2008/0177119 A1 | 7/2008 | Juttu et al. |
| 2008/0177149 A1 | 7/2008 | Weinert et al. |
| 2008/0177165 A1 | 7/2008 | Blomquist et al. |
| 2008/0183494 A1 | 7/2008 | Cuddihy et al. |
| 2008/0201325 A1 | 8/2008 | Doniger et al. |
| 2008/0206799 A1 | 8/2008 | Blomquist |
| 2008/0214919 A1 | 9/2008 | Harmon et al. |
| 2008/0228056 A1 | 9/2008 | Blomquist et al. |
| 2008/0234943 A1 | 9/2008 | Ray et al. |
| 2008/0234992 A1 | 9/2008 | Ray et al. |
| 2008/0243902 A1 | 10/2008 | Rong et al. |
| 2008/0255438 A1 | 10/2008 | Saidara et al. |
| 2008/0262745 A1 | 10/2008 | Polidori |
| 2008/0269585 A1 | 10/2008 | Ginsberg |
| 2008/0306353 A1 | 12/2008 | Douglas et al. |
| 2008/0319384 A1 | 12/2008 | Yodfat et al. |
| 2009/0006061 A1 | 1/2009 | Thukral et al. |
| 2009/0018406 A1 | 1/2009 | Yodfat et al. |
| 2009/0150177 A1 | 6/2009 | Buck et al. |
| 2009/0150186 A1 | 6/2009 | Cohen et al. |
| 2009/0164239 A1 | 6/2009 | Hayter et al. |
| 2009/0176692 A1 | 7/2009 | Habermann et al. |
| 2009/0177147 A1 | 7/2009 | Blomquist et al. |
| 2009/0234262 A1 | 9/2009 | Reid et al. |
| 2009/0247836 A1 | 10/2009 | Cole et al. |
| 2009/0253970 A1 | 10/2009 | Bashan et al. |
| 2009/0253973 A1 | 10/2009 | Bashan et al. |
| 2009/0281393 A1 | 11/2009 | Smith |
| 2010/0016700 A1 | 1/2010 | Sieh et al. |
| 2010/0138197 A1 | 6/2010 | Sher |
| 2010/0141656 A1 | 6/2010 | Krieftewirth |
| 2010/0160757 A1 | 6/2010 | Weinert et al. |
| 2010/0174553 A1 | 7/2010 | Kaufman et al. |
| 2010/0198142 A1 | 8/2010 | Sloan et al. |
| 2010/0198520 A1 | 8/2010 | Breton et al. |
| 2010/0222765 A1 | 9/2010 | Blomquist et al. |
| 2010/0262434 A1 | 10/2010 | Shaya |
| 2010/0265073 A1 | 10/2010 | Harper |
| 2010/0274497 A1 | 10/2010 | Rush |
| 2010/0330598 A1 | 12/2010 | Thukral et al. |
| 2010/0331650 A1 | 12/2010 | Batman et al. |
| 2010/0331651 A1 | 12/2010 | Groll |
| 2011/0071365 A1 | 3/2011 | Lee et al. |
| 2012/0226117 A1 | 9/2012 | Lamego et al. |

FOREIGN PATENT DOCUMENTS

| | | |
|---|---|---|
| WO | 01/52727 A1 | 7/2001 |
| WO | 03/002258 A1 | 1/2003 |
| WO | 03/046695 A2 | 6/2003 |
| WO | 03/082096 A1 | 10/2003 |
| WO | 2004/015539 A2 | 2/2004 |
| WO | 2004/084820 A2 | 10/2004 |
| WO | 2007/081853 A2 | 7/2007 |
| WO | 2007117719 A2 | 10/2007 |
| WO | 2007/149319 A2 | 12/2007 |
| WO | 2007144419 A2 | 12/2007 |
| WO | 2008/091320 A2 | 7/2008 |
| WO | 2008/105859 A1 | 9/2008 |
| WO | 2008/131324 A1 | 10/2008 |
| WO | 2009/009528 A2 | 1/2009 |
| WO | 2009/013637 A2 | 1/2009 |
| WO | 2009/075925 A1 | 6/2009 |
| WO | 2009/146119 A2 | 12/2009 |
| WO | 2010/000266 A1 | 1/2010 |
| WO | 2010/039743 A1 | 4/2010 |
| WO | 2010/075350 A1 | 7/2010 |
| WO | 2010072387 A2 | 7/2010 |
| WO | 2010/089305 A1 | 8/2010 |
| WO | 2010/089306 A1 | 8/2010 |
| WO | 2010089304 A1 | 8/2010 |
| WO | 2010089307 A1 | 8/2010 |
| WO | 2010/097796 A1 | 9/2010 |

OTHER PUBLICATIONS

Nathan et al., Medical Management of Hyperglycemia in Type 2 Diabetes: A Consensus Algorithm for the Initiation and Adjustment of Therapy, Diabetes Care, vol. 31, No. 12: pp. 1-11, Dec. 2008.

Riddle et al., "The Treat-to_Target Trial, Ramdomized addition of glargine or human NPH insulin to oral therapy of type 2 diabetic patients" Diabetes Care, vol. 26, No. 11: pp. 2080-3086, Nov. 2003.

Non-final Office Action pertaining to U.S. Appl. No. 12/818,310, dated Sep. 26, 2012.

Non-final Office Action pertaining to U.S. Appl. No. 12/818,795 dated Sep. 6, 2012.

Non-final Office Action pertaining to U.S. Appl. No. 12/643,415 dated Sep. 13, 2012.

Breton, M. et al.; Analysis, Modeling, and Simulation of the Accuracy of Continuous Glucose Sensors; Journal of Diabetes Science and Technology; Sep. 2008; pp. 853-862; vol. 2, Issue 5; Diabetes Technology Society.

* cited by examiner

| 145 | | | | 163 | 158 |
|---|---|---|---|---|---|
| 237a | 240a | 256a | Y ←159 | 12/23/2009 8:00 | 1 |
| 237b | 240b | 256b | N | 12/23/2009 9:00 | 2 | 5, 1 |
| 237c | 240c | 256c | N | 12/23/2009 9:30 | 3 | 5, 1 |
| 237d | 240d | 256d | N | 12/23/2009 10:00 <null> | |
| ... | ... | ... | ... | ... | ... |
| 237n | 240n | 256n | N | mm/dd/yyyy hh:mm n | |

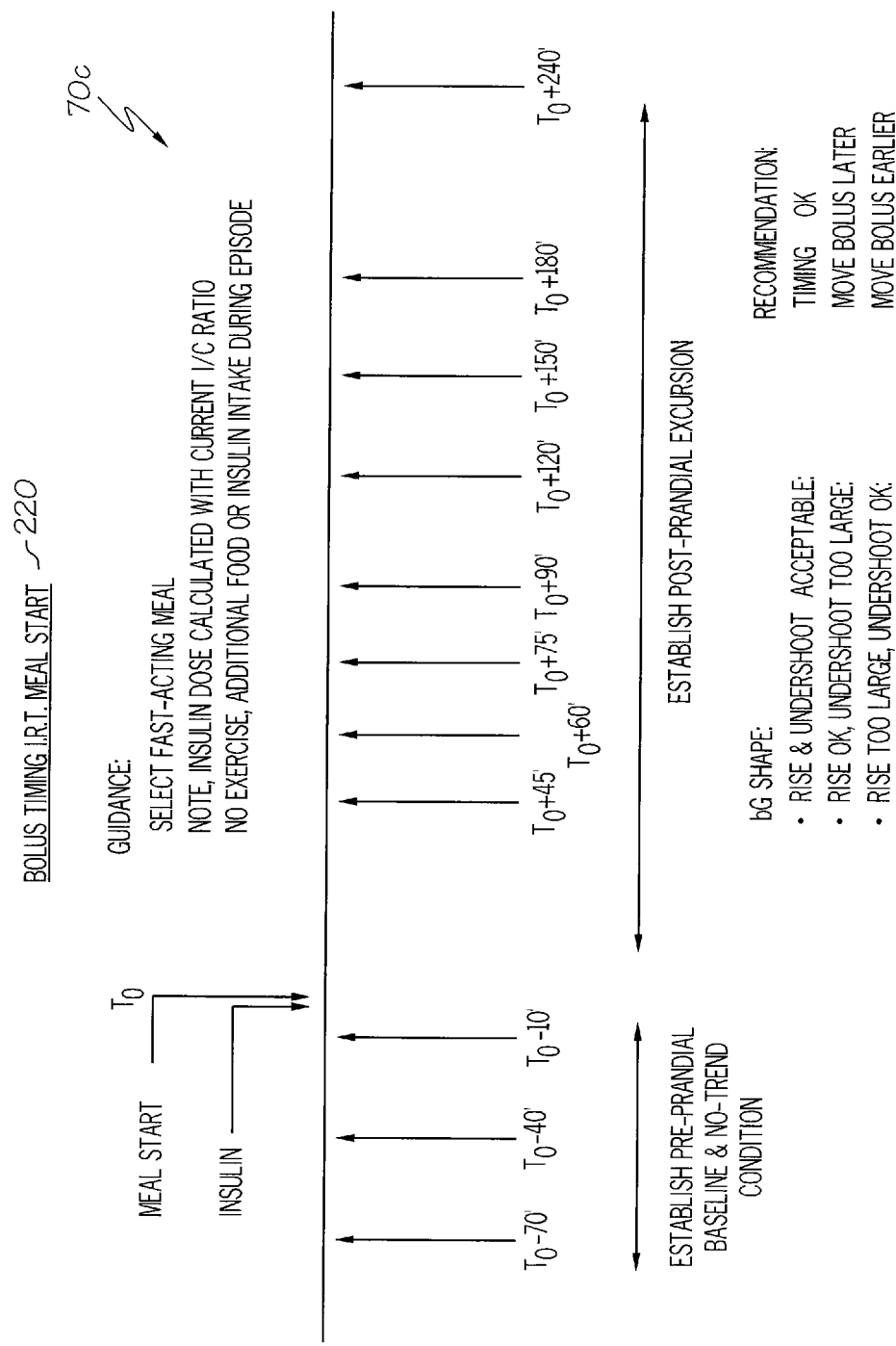

| PARAMETERS | bG (BIOSENSOR) MEASUREMENT | MEAL SIZE (S, M, OR L) | ENERGY LEVEL (1-5) | TIMING | ADHERENCE CRITERIA | GUIDANCE | OPTIONS | View flag |
|---|---|---|---|---|---|---|---|---|
| bG LEVEL TRENDING | | | | | | | | |
| ENTRY CRITERIA | | | | MM-DD-YYYY | AFFIRMS GUIDANCE, IF NOT ADD 1 DAY TO TIMING | ARE YOU WILLING TO CONDUCT A TEST OVER 3 CONSECUTIVE DAYS? | | |
| EXIT CRITERIA | | | | MM-DD-YYYY | ENTRY TIMING + 3 DAYS | | | |
| BEFORE BREAKFAST | Y | | Y | HH:MM | | PLEASE INDICATE ENERGY LEVEL | 1 | Y |
| $n_1$ HOURS AFTER BREAKFAST | Y | Y | Y | $n_1$ | ± 30 MINUTES OF $n_1$ | PLEASE INDICATE MEAL SIZE & ENERGY LEVEL | | N |
| BEFORE LUNCH | Y | | Y | | | PLEASE INDICATE ENERGY LEVEL | | N |
| $n_2$ HOURS AFTER LUNCH | Y | Y | Y | $n_2$ | ± 30 MINUTES OF $n_2$ | PLEASE INDICATE MEAL SIZE & ENERGY LEVEL | 2 | AC |
| BEFORE DINNER | Y | | Y | | | PLEASE INDICATE ENERGY LEVEL | | N |
| $n_3$ HOURS AFTER DINNER | Y | Y | Y | $n_3$ | ± 30 MINUTES OF $n_3$ | PLEASE INDICATE MEAL SIZE & ENERGY LEVEL | 3 | nAC |
| BEFORE BED | Y | | Y | | | PLEASE INDICATE ENERGY LEVEL | | N |

COLLECTION DEVICE WITH SELECTIVE DISPLAY OF TEST RESULTS, METHOD AND COMPUTER PROGRAM PRODUCT THEREOF

CROSS REFERENCE TO RELATED APPLICATIONS

The present application is a continuation in part of U.S. patent application Ser. No. 12/643,415, filed Dec. 21, 2009, which claims priority to U.S. Provisional Application Ser. No. 61/140,270 filed Dec. 23, 2008, both of which are incorporated by reference herein in their entirety.

TECHNICAL FIELD

Embodiments of the invention relate generally to meters used for physiological monitoring, and in particular, to a collection device with selective display of test results, method and computer program product thereof.

BACKGROUND

For people with diabetes, successful management requires monitoring the effects lifestyle changes can have in both short-term and long-term time frames. Regular testing of their blood glucose level can be an important part of diabetes management as a way to track changes throughout the day. For example, portable handheld medical diagnostic devices are often employed to measure concentrations of biologically significant components of bodily fluids, such as, for example, glucose concentration in blood. To test glucose with a glucose meter, a small sample of blood may be placed on a disposable test strip. The portable handheld glucose meter may include a strip port that receives the disposable test strip. The test strip may be coated with chemicals (glucose oxidase, dehydrogenase, or hexokinase) that combine with glucose in blood allowing it to measure the concentration of glucose in the blood sample. The portable handheld glucose meter then displays the glucose concentration as a number (or glucose measurement value). As a result, the portable handheld medical diagnostic devices and their accessories may work together to measure the amount of glucose in blood and be used to monitor glucose levels in one's home, healthcare facility or other location, for example, by persons having diabetes or by a healthcare professional.

Patients and healthcare professionals may thereby track and analyze glucose measurements over a period of time to assess changes in the patient over the course of a day, week or other desirable timeframe. In other examples, some healthcare professionals may instruct a patient to obtain glucose measurements several times a day over a course of a few consecutive days as part of a test regime or protocol implemented in hopes to observe and assess changes in a patient's physiological condition. For example, the protocol may specify taking blood glucose measurements which correlate to certain eating times, meal types and size, exercising, and so forth.

It is to be appreciated that in conventional glucose meters the results of such glucose measurements are readily viewable by the patient as well as any other data that may be collected by the meter. However, patients following a certain protocol for testing a physiological parameter like glucose and optionally collecting additional information as prescribed by the protocol may change intentionally or unintentionally their behavior when they see the test results. Since such a protocol may be used to assess a certain aspect of a patient's current medical situation, a modification of the patient's behavior while following the protocol may negatively impact the validity of the test results.

SUMMARY

It is against the above background that the present invention discloses a method, system, and computer program product for providing a selective display of test results. Using the embodiments of the present invention, a clinician can monitor a patient according to a desired structured collection procedure while preventing the patient from modifying his or her behavior based on the collection results obtained from the patient performing the collection procedure. For example, if a patient typically measures blood glucose once per day at a specific time and the patient's clinician wants to gather additional blood glucose readings but does not want the patient to change his or her eating or other habits based on the additional test results, the clinician can define a structured collection procedure which instructs the patient to test multiple times per day but only allows the collection device to present a single test result to the patient corresponding to the patient's normal testing time. In this manner, the patient will not be able to modify his or her normal behavior based on the additional test results.

In one embodiment, a portable collection device is disclosed and comprises a display; a user interface; a measurement engine to measure a biomarker value; memory containing a data file and a structured collection procedure. The structured collection procedure has parameters defining: a schedule of collection events having one or more collection events which provide a request for a measurement of the biomarker value under defined conditions which are related to the biomarker value as contextual information associated with the biomarker value, and a view flag associated with each of the one or more collection events. The view flag has a viewable value and a non-viewable value. The device further comprises a processor is connected to the display, the user interface, the measurement engine, and the memory, a power supply for powering the device, and software. The software has instructions that when executed by the processor causes the processor to: read the structured collection procedure from memory, permit an authorized user to select at least one criterion under which a data record of the data file for the structured collection procedure is designated as viewable, run the structured collection procedure, send automatically the request of each of the one or more collection events according to the structured collection procedure, store automatically biomarker value(s) measured by the measurement engine or information entered via the user interface in an associated data record of the data file in the memory in response to sent request, store and link automatically contextual information associated with each biomarker value or the information entered in the associated data record of the data file to form contextualized biomarker data, designate automatically the associated data record in the memory containing the contextualized biomarker data as viewable if the view flag associated with the sent request in the structured collection procedure has the viewable value or the at least one criterion is met and as not viewable if the view flag has the non-viewable value or the at least one criterion is not met, and provide only biomarker values associated to data records containing the contextualized biomarker data if the data records are designated in the memory as viewable.

In another embodiment, a method of monitoring a patient according to a desired structured collection procedure while preventing the patient from modifying his or her behavior based on collection results is disclosed. The method comprises providing a portable collection device according to the above embodiment of the present invention, and running the software provided on the collection device. In running the software, the processor: reads the structured collection procedure from memory, runs the structured collection procedure, sends automatically requests to the display according to the timing of the collection events prescribed by the structured collection procedure, stores automatically each biomarker value measured by the measurement engine or information entered via the user interface in an associated data record of the data file in the memory in response to the sent requests, stores and links automatically contextual information associated with each biomarker value or the information entered in the associated data record of the data file to form contextualized biomarker data, designates automatically the associated data record containing the contextualized biomarker data in the memory as viewable if the view flag provided in the structured collection procedure for the collection event has the viewable value and as not viewable if the view flag has the non-viewable value, and provides to the display only data records containing the contextualized biomarker data designated in the memory as viewable.

In still another embodiment, a computer readable storage medium is disclosed which stores software comprising instructions that when executed by a collection device having a processor, a measurement engine for measuring a biomarker value, a user interface, memory, and a display performs a method for monitoring a patient according to a desired structured collection procedure while preventing the patient from modifying his or her behavior based on collection results. The method executed by the processor comprises: running the structured collection procedure; sending automatically requests to the user interface according to timing of collection events prescribed by the structured collection procedure; storing automatically each biomarker value measured by the measurement engine or information entered via the user interface in an associated data record in a data file provided in the memory in response to the sent requests; storing and linking automatically contextual information associated with each biomarker value or the information entered in the associated data record of the data file to form contextualized biomarker data, designating automatically the associated data record containing the contextualized biomarker data in the memory as viewable if the view flag provided in the structured collection procedure for the collection event has the viewable value and as not viewable if the view flag has the non-viewable value; and providing to the display only data records containing the contextualized biomarker data designated in the memory as viewable.

These and other advantages, features, and embodiments of the invention disclosed herein will be made more apparent from the description, drawings and claims that follow.

BRIEF DESCRIPTION OF THE DRAWINGS

The following detailed description of the embodiments of the present invention can be best understood when read in conjunction with the following drawings, in which:

FIG. 4 shows a depiction in tabular format of a data record embodiment created from using a structured collection procedure on the collection device of FIG. 3 according to the present invention;

FIGS. 6A, 6B, 6C, 6D, and 6E show various structured collection procedures embodiments defined according to the present invention;

FIG. 7B depicts a structured collection procedure according to an embodiment of the present invention which may be implemented on the collection device in the embodiment shown by FIG. 3;

FIGS. 8B and 8C show a method of implementing a structured collection procedure via a graphical user interface provided on a collection device, such as depicted by FIG. 3, according to an embodiment of the present invention.

DETAILED DESCRIPTION

Figure 1:
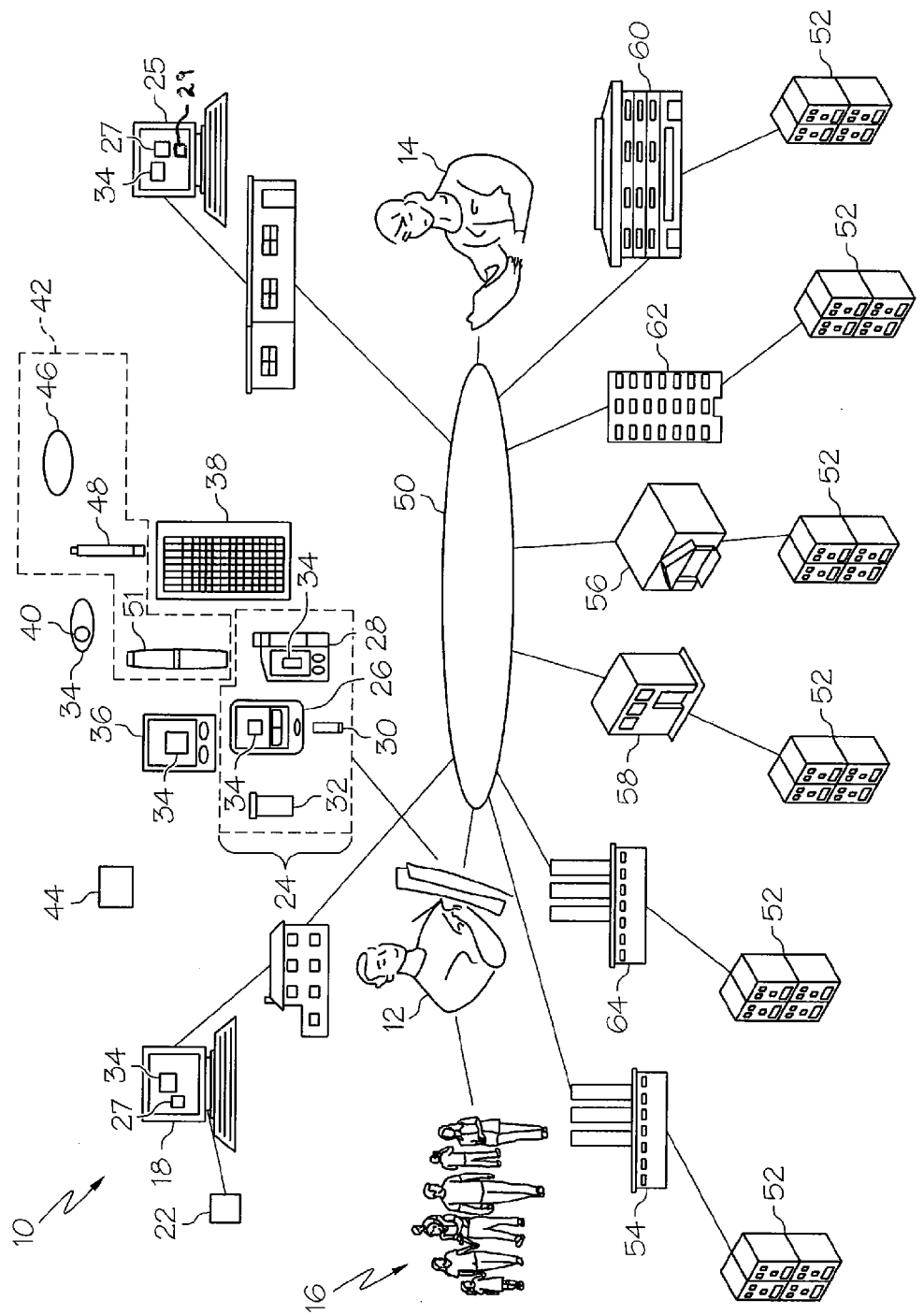
FIG. 1 is a diagram showing a chronic care management system for a diabetes patient and a clinician along with others having an interest in the chronic care management of the patient according to an embodiment of the present invention.

The present invention will be described below relative to various illustrative embodiments. Those skilled in the art will appreciate that the present invention may be implemented in a number of different applications and embodiments and is not specifically limited in its application to the particular embodiments depicted herein. In particular, the present invention will be discussed below in connection with diabetes management via sampling blood, although those of ordinary skill will recognize that the present invention could be modified to be used with other types of fluids or analytes besides glucose, and/or useful in managing other diseases besides diabetes.

As used herein with the various illustrated embodiments described below, the following terms include, but are not limited to, the following meanings.

The term "biomarker" can mean a physiological variable measured to provide data relevant to a patient such as for example, a blood glucose value, an interstitial glucose value, an HbA1c value, a heart rate measurement, a blood pressure measurement, lipids, triglycerides, cholesterol, and the like.

The term "contextualizing" can mean documenting and interrelating conditions that exist or will occur surrounding a collection of a specific biomarker measurement. Preferably, data about documenting and interrelating conditions that exist or will occur surrounding a collection of a specific biomarker are stored together with the collected biomarker data and are linked to it. In particular, a further assessment of the collected biomarker data takes into account the data about documenting and interrelating conditions so that not only the data as such are evaluated but also the link between data to which it is contextualized. The data about documenting and interrelating conditions can include, for example, information about the time, food and/or exercises which occurs surrounding a collection of a specific biomarker measurement and/or simultaneously thereto. For example, the context of a structured collection procedure in an embodiment according to the present invention can be documented by utilizing entry criterion for verifying a fasting state with the user before accepting a biomarker value during a Basal titration optimization structured collection procedure.

The term "contextualized biomarker data" can mean the information on the interrelated conditions in which a specific biomarker measurement was collected combined with the measured value for the specific biomarker. In particular, the biomarker data are stored together with the information on the interrelated conditions under which a specific biomarker measurement was collected and are linked thereto.

The term "criteria" can mean one criterion or more criteria, and can be at least one or more of a guideline(s), rule(s), characteristic(s), and dimension(s) used to judge whether one or more conditions are satisfied or met to begin, accept, and/or end one or more procedural steps, actions, and/or values.

The term "adherence" can mean that a person following a structured collection procedure performs requested procedural steps appropriately. For example, the biomarker data should be measured under prescribed conditions of the structured collection procedure. If then the prescribed conditions are given for a biomarker measurement the adherence is defined as appropriate. For examples, the prescribed conditions are time related conditions and/or exemplarily can include eating of meals, taking a fasting sample, eating a type of meal with a requested window of time, taking a fasting sample at a requested time, sleeping a minimum amount of time, and the like. The adherence can be defined as appropriate or not appropriate for a structured collection procedure, a group of sample instances, or a single data point of a contextualized (biomarker) data. Preferably, the adherence can be defined as appropriate or not appropriate by a range of a prescribed condition(s) or by a selectively determined prescribed condition(s). Moreover the adherence can be calculated as a rate of adherence describing in which extent the adherence is given for a structured collection procedure, or a single data point in particular of a contextualized biomarker data.

The term "adherence event" can mean when a person executing a structured collection procedure fails to perform a procedural step. For example, if a person did not collect data when requested by the collection device, the adherence is determined as not appropriate resulting in an adherence event. In another example, adherence criteria could be a first criterion for the patient to fast 6 hours and a second criterion for collecting a fasting bG value at a requested time. In this example, if the patient provides the bG sampling at the requested time but fasted only 3 hours before providing the bG sample, then although the second adherence criterion is met, the first adherence criterion is not, and hence an adherence event for the first criterion would occur.

The term "violation event" is a form of an adherence event in which the person executing the structured collection (testing) procedure (protocol) does not administer a therapeutic at a recommended time, does not administer a recommended amount, or both.

The term "adherence criterion" can include adherence and can also mean a basis for comparison (e.g., assessment) of a measured value, a value related to a measured value and/or a calculated value with a defined value or defined range of the value wherein based on the comparison data are accepted with approval and positive reception. Adherence criterion can take into account time related values and/or adherence in one embodiment, but also can take into account noise in other embodiments, and the like. Furthermore, adherence criterion can be applied to contextualized biomarker data so that a biomarker data is accepted depending on a comparison of the contextualized data about documenting and interrelating conditions that exists or occurs surrounding the collection of the specific biomarker. Adherence criterion can be akin to a sanity check for a given piece of information, or group of information. Preferably, the single data point/information or group of data or information is rejected if the accepted criterion is not fulfilled. In particular, such rejected data are then not used for further calculations which are used to provide a therapy recommendation. Mainly the rejected data are only used to assess the adherence and/or to trigger automatically at least one further action. For example, such a triggered action prompts the user then to follow a structured collection procedure or a single requested action so that based on that the adherence criterion can be fulfilled. The adherence criterion(s) additionally can be used as a trigger or logical switch for a filtering action, such as, deciding what information can be displayed.

The term "data event request" can mean an inquiry for a collection of data at a single point in space-time defined by a special set of circumstances, for example, defined by time-related or not time-related events.

The term "medical use case or question" can mean at least one or more of a procedure, situation, condition, and/or question providing an uncertainty about the factuality, or existence of some medical facts, combined with a concept that is not yet verified but that if true would explain certain facts or phenomena. A medical use case or question can be pre-loaded in the system so that the user can select between different medical use cases or questions. Alternatively, the medical use case or question can be defined by the user themselves.

The terms "focused", "structured", and "episodic" are used herein interchangeably with the term "testing" and can mean a predefined sequence in which to conduct the testing.

The terms "software" and "program" may be used interchangeably herein.

FIG. 1 shows a chronic care management system 10 for a diabetes patient(s) 12 and a clinician(s) 14 along with others 16 having an interest in the chronic care management of the patient 12. Patient 12, having dysglycemia, may include persons with a metabolic syndrome, pre-diabetes, type 1 diabetes, type 2 diabetes, and gestational diabetes. The others 16 with an interest in the patient's care may include family members, friends, support groups, and religious organizations all of which can influence the patient's conformance with therapy. The patient 12 may have access to a patient computer 18, such as a home computer, which can connect to a public network 50 (wired or wireless), such as the internet, cellular network, etc., and couple to a dongle, docking station, or device reader 22 for communicating with an external portable device, such as a portable collection device 24. An example of a device reader is shown in the manual "Accu-Chek® Smart Pix Device Reader User's Manual" (2008) available from Roche Diagnostics.

The collection device 24 can be essentially any portable electronic device that can function as an acquisition mechanism for determining and storing digitally a biomarker value(s) according to a structured collection procedure, and which can function to run the structured collection procedure and the method of the present invention. In a preferred embodiment, the collection device 24 can be a self-monitoring blood glucose meter 26 or a continuous glucose monitor 28. Greater details regarding these various illustrated embodiments of the structured collection procedure are provided hereafter in later sections.

In addition to the collection device 24, the patient 12 can use a variety of products to manage his or her diabetes including: test strips 30 carried in a vial 32 for use in the collection device 24; diabetes software 34 which can operate on the patient computer 18, the collection device 24, a handheld computing device 36, such as a laptop computer, a personal digital assistant, and/or a mobile phone; and paper tools 38. Software 34 can be pre-loaded or provided either via a computer readable medium 40 or over the public network 50 and loaded for operation on the patient computer 18, the collection device 24, the clinician computer/office workstation 25, and the handheld computing device 36, if desired. In still other embodiments, the software 34 can also be integrated into the device reader 22 that is coupled to the computer (e.g., computers 18 or 25) for operation thereon, or accessed remotely through the public network 50, such as from a server 52.

The patient 12 can also use for certain diabetes therapies additional therapy devices 42 and other devices 44. Additionally, therapy devices 42 can include devices such as an ambulatory infusion pump 46, an insulin pen 48, and a lancing device 51. An example of an ambulatory insulin pump 46 include but not limited thereto the Accu-Chek® Spirit pump described in the manual "Accu-Chek® Spirit Insulin Pump System Pump User Guide" (2007) available from Disetronic Medical Systems AG. The other devices 44 can be medical devices that provide patient data such as blood pressure, fitness devices that provide patient data such as exercise information, and elder care device that provide notification to care givers. The other devices 44 can be configured to communicate with each other according to standards planned by Continua® Health Alliance.

The clinicians 14 for diabetes are diverse and can include e.g., nurses, nurse practitioners, physicians, endocrinologists, and other such health care providers. The clinician 14 typically has access to a clinician computer 25, such as a clinician office computer, which can also be provided with the software 34. A healthcare record system 27, such as Microsoft® HealthVault™ and Google™ Health, may also be used by the patient 12 and the clinician 14 on computers 18, 25 to exchange information via the public network 50 or via other network means (LANs, WANs, VPNs, etc.), and to store information such as collection data from the collection device 24 to an electronic medical record of the patient e.g., EMR 53 (FIG. 2A) which can be provided to and from computers 18, 25 and/or server 52.

Figure 2:
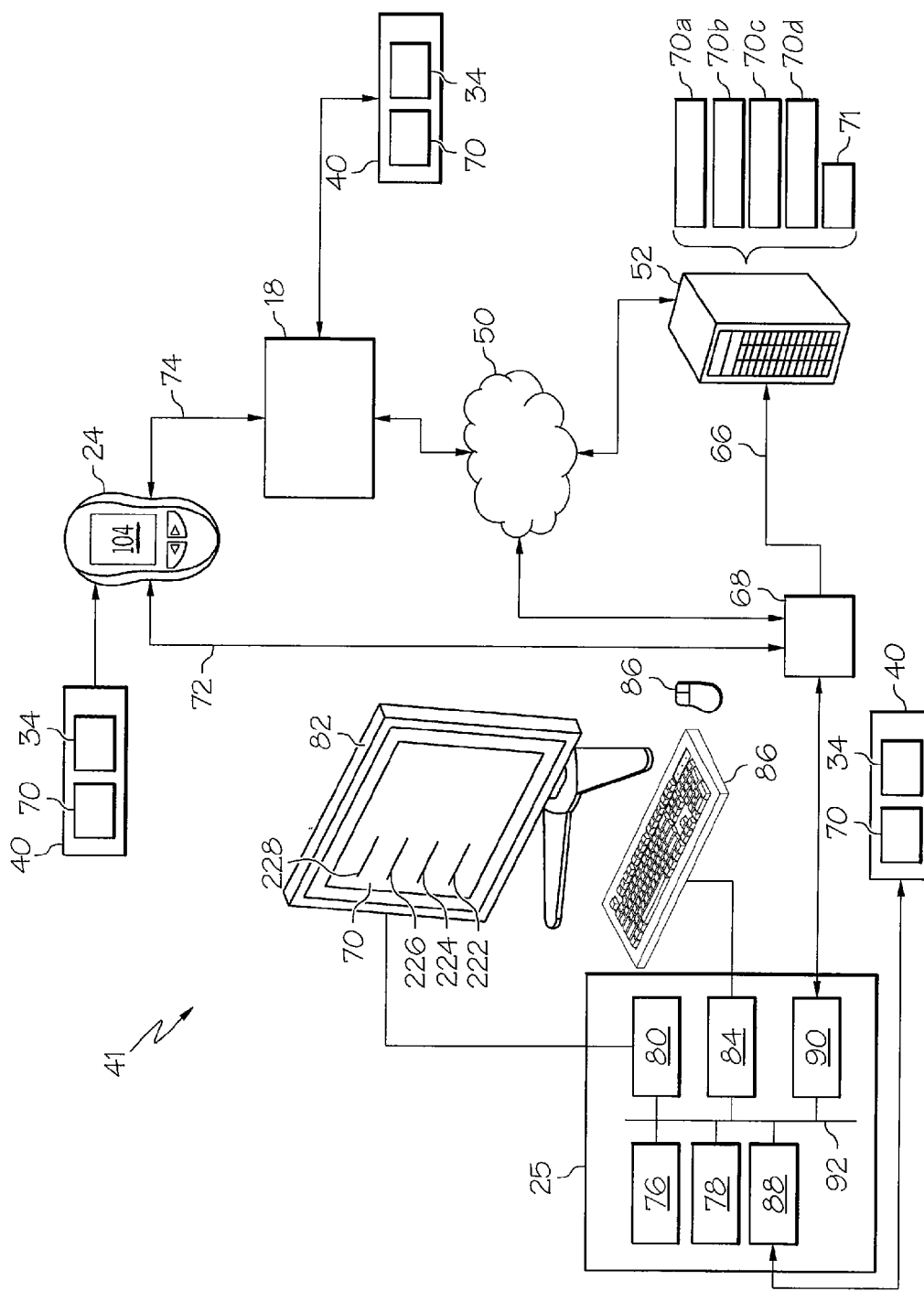
FIGS. 2 and 2A are diagrams showing embodiments of a system suitable for implementing a structured collecting procedure according to an embodiment of the present invention.

Most patients 12 and clinicians 14 can interact over the public network 50 with each other and with others having computers/servers 52. Such others can include the patient's employer 54, a third party payer 56, such as an insurance company who pays some or all of the patient's healthcare expenses, a pharmacy 58 that dispenses certain diabetic consumable items, a hospital 60, a government agency 62, which can also be a payer, and companies 64 providing healthcare products and services for detection, prevention, diagnosis and treatment of diseases. The patient 12 can also grant permissions to access the patient's electronic health record to others, such as the employer 54, the payer 56, the pharmacy 58, the hospital 60, and the government agencies 62 via the healthcare record system 27, which can reside on the clinician computer 25 and/or one or more servers 52. Reference hereafter is also made to FIG. 2.

FIG. 2 shows a system embodiment suitable for implementing a structured testing method according to an embodiment of the present invention, which in another embodiment can be a part of the chronic care management system 10 and communicate with such components, via conventional wired or wireless communication means. The system 41 can include the clinician computer 25 that is in communication with a server 52 as well as the collection device 24. Communications between the clinician computer 25 and the server 52 can be facilitated via a communication link to the public network 50, to a private network 66, or combinations thereof. The private network 66 can be a local area network or a wide are network (wired or wireless) connecting to the public network 50 via a network device 68 such as a (web) server, router, modem, hub, and the likes.

In one embodiment, the server 52 can be a central repository for a plurality of structured collection procedures (or protocols) 70a, 70b, 70c, 70d, in which the details of a few exemplary structured collection procedures are provided in later sections. The server 52, as well as the network device 68, can function also as a data aggregator for completed ones of the structured collection procedures 70a, 70b, 70c, 70d. Accordingly, in such an embodiment, data of a completed collection procedure(s) from a collection device of the patient 12 can then be provided from the server 52 and/or network device 68 to the clinician computer 25 when requested in response to a retrieval for such patient data.

Figure 2A:
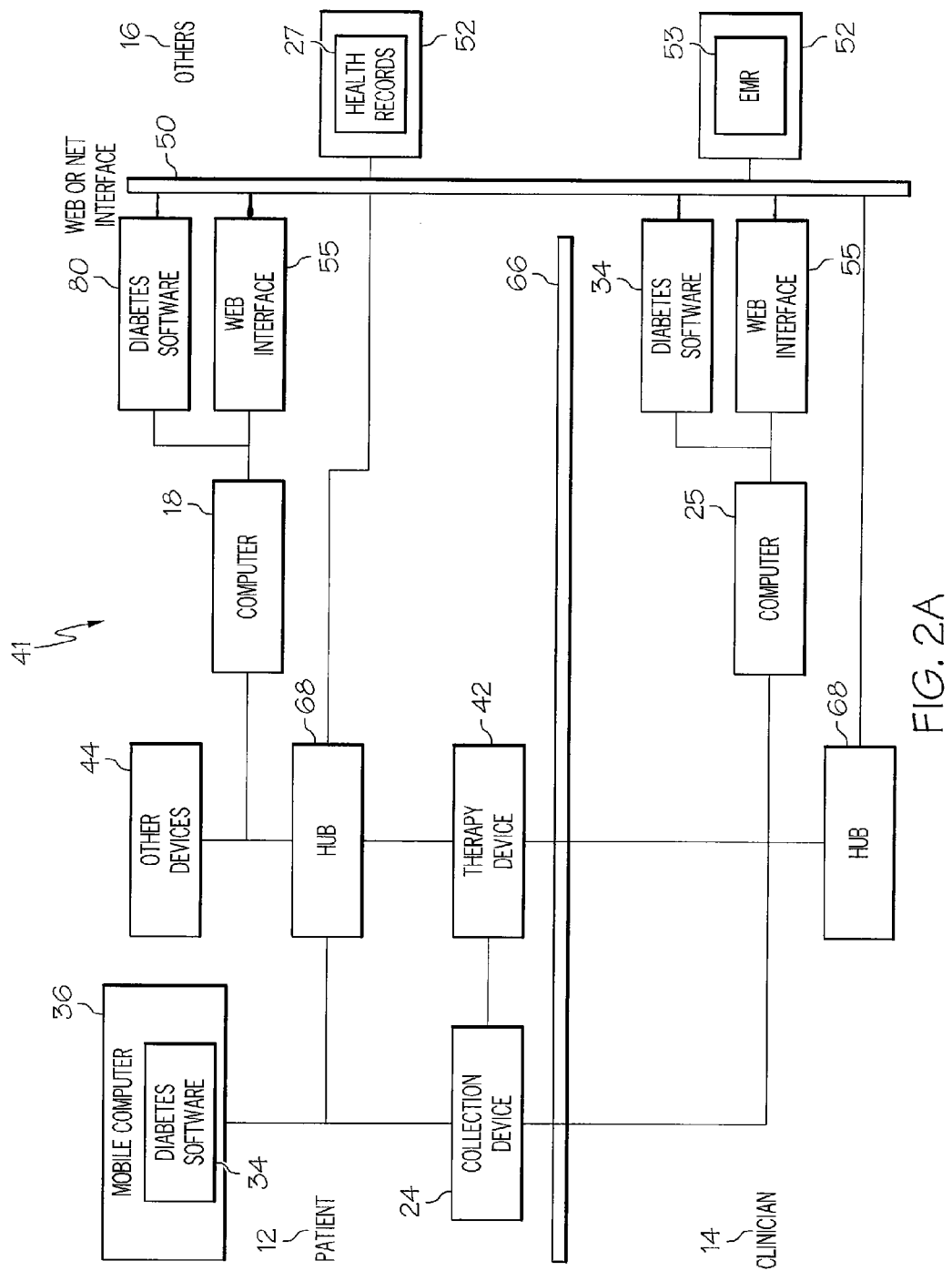

In one embodiment, one or more of the plurality of structured collection procedures 70a, 70b, 70c, 70d on the server 52 can be provided over the public network 50, such as through a secure web interface 55 (FIG. 2A, showing another embodiment of the system 41) implemented on the patient computer 18, the clinician computer 25, and/or the collection device 24. In another embodiment, the clinician computer 25 can serve as the interface (wired or wireless) 72 between the server 52 and the collection device 24. In still another embodiment, the structured collection procedures 70a, 70b, 70c, 70d, as well as software 34, may be provided on a computer readable medium 40 and loaded directly on the patient computer 18, the clinician computer 25, and/or the collection device 24. In still another embodiment, the structured collection procedures 70a, 70b, 70c, 70d may be provided pre-loaded (embedded) in memory of the collection device 24. In still other embodiments, new/updated/modified structured collection procedures 70a, 70b, 70c, 70d may be sent between the patient computer 18, the clinician computer 25, the server 52 and/or the collection device 24 via the public network 50, the private network 66, via a direct device connection (wired or wireless) 74, or combinations thereof. Accordingly, in one embodiment the external devices e.g., computers 18 and/or 25, can be used to establish a communication link 72, 74 between the collection device 24 and still further electronic devices such as other remote Personal Computer (PC), and/or servers such as through the public network 50, such as the Internet and/or other communication networks (e.g., LANs, WANs, VPNs, etc.), such as private network 66.

Figure 3:
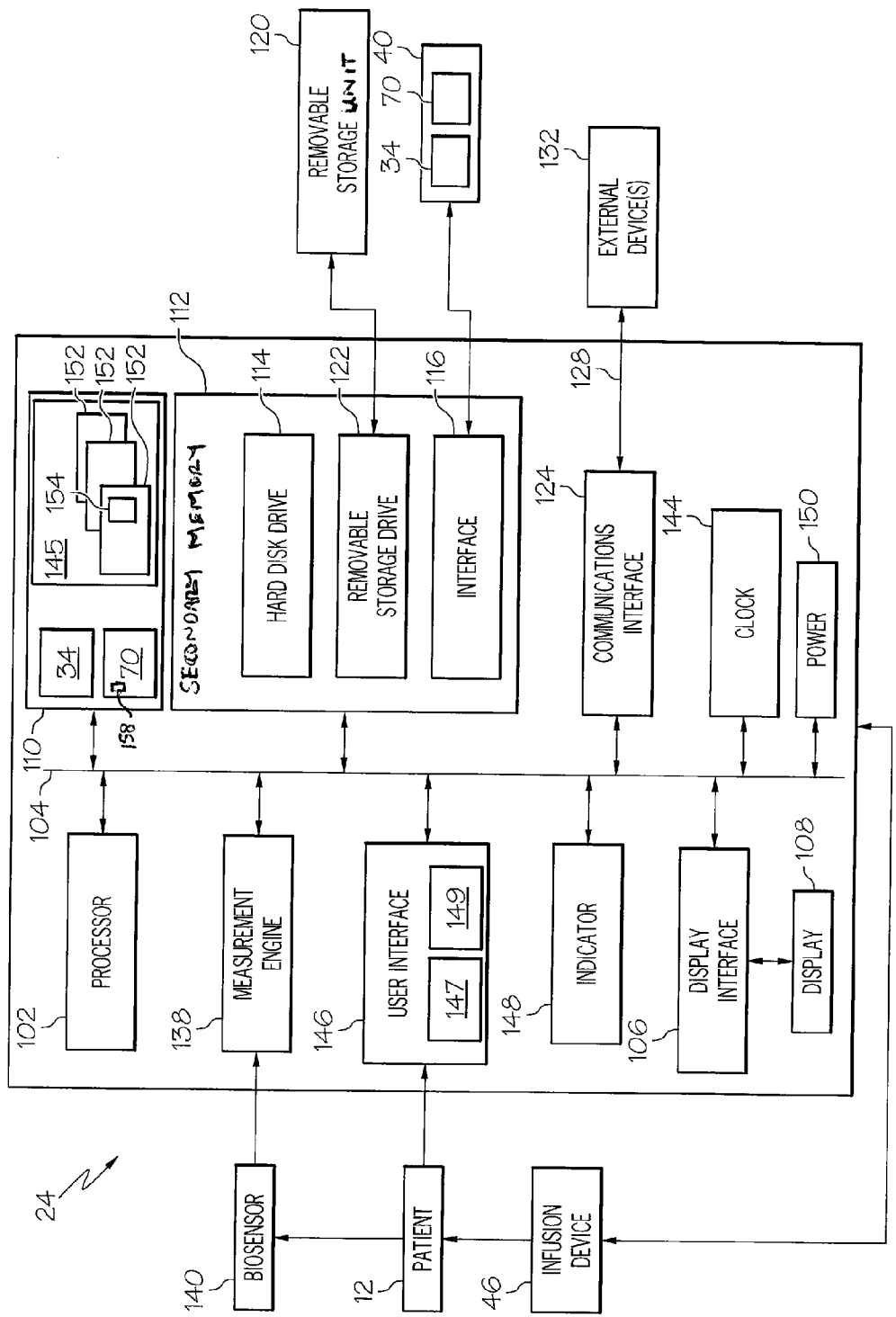
FIG. 3 depicts a block diagram conceptually illustrating a portable collection device useful to implement the various embodiments of the present invention.

The clinician computer 25, as a conventional personal computer/workstation, can include a processor 76 which executes programs, such as software 34, and such as from memory 78 and/or computer readable medium 40. Memory 78 can include system memory (RAM, ROM, EEPROM, etc.), and storage memory, such as hard drives and/or flash memory (internal or external). The clinician computer 25 can also include a display driver 80 to interface a display 82 with the processor 76, input/output connections 84 for connecting user interface devices 86, such as a keyboard and mouse (wired or wireless), and computer readable drives 88 for portable memory and discs, such as computer readable medium 40. The clinician computer 25 can further include communication interfaces 90 for connections to the public network 50 and other devices, such as collection device 24 (wired or wireless), and a bus interface 92 for connecting the above mentioned electronic components to the processor 76. Reference hereafter is now made to FIG. 3.

FIG. 3 is a block diagram conceptually illustrating a portable collection device 24 utilized to implement the present invention such as, for example, the portable collection device 24 depicted in FIG. 2. It is to be appreciated that the collection device 24 can be essentially any portable electronic device that can function as an acquisition mechanism for determining and storing digitally a biomarker value(s) according to a structured collection procedure, and which can function to run the structured collection procedure and the method of the present invention.

In one embodiment, the collection device 24 is a portable, self-monitoring blood glucose meter (e.g., meter 26) which makes a determination of a blood glucose level via a measurement instrument that reads glucose concentrations by optical, electrochemical, electromechanical or calorimetric detection/measurement methods. An example of a blood glucose meter is an Accu-Chek® Aviva described in the booklet "Accu-Chek® Aviva Blood Glucose Meter Owner's Booklet (2007), portions of which are disclosed in U.S. Pat. No. 6,645,368 B1 entitled "Meter and method of using the meter for determining the concentration of a component of a fluid" assigned to Roche Diagnostics Operations, Inc., which is hereby incorporated by reference.

In another embodiment, the collection device 24 can be a continuous glucose monitor (e.g., monitor 28). As a continuous glucose monitor, the collection device 24 can be used to obtain time-resolved data to identify fluctuations and trends that would otherwise go unnoticed with spot monitoring of blood glucose levels and standard HbA1c tests such as low overnight glucose levels, high blood glucose levels between meals, early morning spikes in blood glucose levels, and how diet and physical activity affect blood glucose along with the effect of therapy changes. An example of a continuous glucose monitor is shown in U.S. Pat. No. 7,389,133 "Method and device for continuous monitoring of the concentration of an analyte" (Jun. 17, 2008) assigned to Roche Diagnostics Operations, Inc., which is hereby incorporated by reference.

In the illustrated embodiment of FIG. 3, the collection device 24 includes one or more microprocessors, such as processor 102, which may be a central processing unit comprising a single or multi-core and cache memory, which is connected to a communication bus 104, which may include data, memory, control and/or address buses. The collection device 24 may include a display interface 106 providing graphics, text, and other data from the bus 104 (or from a frame buffer not shown) for display on a display 108. The display interface 106 may be a display driver of an integrated graphics solution that utilizes a portion of main memory 110 of the collection device 24, such as random access memory (RAM) and processing from the processor 102 or may be a dedicated graphic processing unit. In another embodiment, the display interface 106 and display 108 additionally provide a touch screen interface for providing data to the collection device 24 in a well-known manner.

Main memory 110 in one embodiment is random access memory (RAM), and in other embodiments may include other memory such as a ROM, PROM, EPROM or EEPROM, and combinations thereof. In one embodiment, the collection device 24 can include secondary memory 112 which may include, for example, a hard disk drive 114 and/or a removable storage drive, representing a floppy disk drive, a magnetic tape drive, an optical disk drive, a flash memory connector (e.g., USB connector, Firewire connector, and PC card slot), etc. The removable storage drive 122 reads from and/or writes to a removable storage unit 120 in a well-known manner. Removable storage unit 120 represents a floppy disk, magnetic tape, optical disk, flash drive, PC card, etc., which is read by and written to by removable storage drive 122. As will be appreciated, the removable storage unit 120 includes a computer usable storage medium having stored therein computer software and/or data.

In alternative embodiments, secondary memory 112 may include other means for allowing computer programs or other instructions to be loaded into the collection device 24. Such means may include, for example, the removable computer readable medium 40 and an interface connector 116. Examples of such a removable computer readable medium/interface include a program cartridge and cartridge interface, a removable memory chip (e.g., ROM, PROM, EPROM, EEPROM, etc.) and associated socket, and other removable computer readable medium 40 and interface connector 116 which allow software and data to be transferred from the removable computer readable medium 40 to the collection device 24.

The collection device 24 in one embodiment includes a communication module 124. The communication module 124 allows software and data to be transferred between the collection device 24 and an external device(s) 132. Examples of communication module 124 may include one or more of a modem, a network interface (such as an Ethernet card), a communications port (e.g., USB, firewire, serial, parallel, etc.), a PC or PCMCIA slot and card, a wireless transceiver, and combinations thereof. The external device(s) 132 can be a personal computer (PC), a personal digital assistance (PDA), a mobile (cellular) phone, and/or a device docking station. In such an embodiment, the docking station may provided and/or connect to one or more of a modem, a network interface (such as an Ethernet card), a communications port (e.g., USB, firewire, serial, parallel, etc.), a PCMCIA slot and card, a wireless transceiver, and combinations thereof. Software and data transferred via communication module 124 are in the form of wired or wireless signals 128 which may be electronic, electromagnetic, optical, or other signals capable of being sent and received by communication module 124. For example, as is known, signals 128 may be sent between communication module 124 and the external device(s) 132 using wire or cable, fiber optics, a phone line, a cellular phone link, an RF link, an infrared link, other communications channels, and combinations thereof.

In one embodiment, the external device 132 is used for establishing a communication link between the collection device 24 and still further electronic devices such as a remote Personal Computer (PC) of the patient, e.g., patient computer 18, and/or a health care provider (HCP) computer, e.g., clinician computer 25, directly or indirectly, such as through a communication network, such as the public network 50 and/or other communication networks, e.g., private network 66 (e.g., LANs, WANs, VPNs, etc.). The communication module 124 and/or external device(s) 132 may also be used to communicate with further data gathering and/or storage devices such as insulin delivering devices, cellular phones, personal digital assistants (PDA), etc. Specific techniques for connecting electronic devices through wired and/or wireless connections (e.g. USB and Bluetooth, respectively) are well known in the art. In another embodiment, the collection device 24 is used with the external device 132, such as provided as a handheld computer or a mobile phone, to perform actions such as prompt a patient to take an action, acquire a data event, and perform calculations on information. An example of a collection device combined with such an external device 132 provided as a hand held computer is disclosed in U.S. patent application Ser. No. 11/424,757 filed Jun. 16, 2006 entitled "System and method for collecting patient information from which diabetes therapy may be determined," assigned to Roche Diagnostics Operations, Inc., which is hereby incorporated by reference. The collection device 24 may also communicate with other device as discussed previously above, which can be medical devices that provide patient data such as blood pressure, fitness devices that provide patient data such as exercise information, and elder care device that provide notification to care givers.

In the illustrative embodiment, the collection device 24 provides a measurement engine 138 for reading a biosensor 140. The biosensor 140, which in one embodiment is a disposable test strip (e.g., test strip 30), is used with the collection device 24 to receive a sample such as for example, of capillary blood, which is exposed to an enzymatic reaction and measured by electrochemistry techniques, optical techniques, or both by the measurement engine 138 to measure and provide a biomarker value, such as for example, a blood glucose level. An example of a disposable biosensor and measurement engine is disclosed in U.S. Patent Pub. No. 2005/0016844 A1 entitled "Reagent stripe for test strip" (Jan. 27, 2005), and assigned to Roche Diagnostics Operations, Inc., which is hereby incorporated by reference. In other embodiments, the measurement engine 138 and biosensor 140 is of a type used to provide a biomarker value for other types of sampled fluids or analytes besides or in addition to glucose, heart rate, blood pressure measurement, and combinations thereof. In still another embodiment, the biosensor 140 may be a sensor with an indwelling catheter(s) or being a subcutaneous tissue fluid sampling device(s), such as when the collection device 24 is implemented as a continuous glucose monitor (CGM) (e.g., monitor 28) in communication with infusion pump 46.

Data, comprising the information provided by the biosensor 140, is provided by the measurement engine 138 to the processor 102, which may execute a computer program stored in memory 110 to perform various calculations and processes using the data. For example, such a computer program is described by U.S. patent application Ser. No. 12/492,667, filed Jun. 26, 2009, titled "Method, system, and computer program product for providing both an estimated true mean blood glucose value and estimated glycated hemoglobin (HbA1C) value from structured spot measurements of blood glucose," and assigned to Roche Diagnostics Operations, Inc., which is hereby incorporated by reference. The data from the measurement engine 138 and the results of the calculation and processes by the processor 102 using the data is herein called self-monitored data. The self-monitored data may include, but not limited thereto, the glucose values of a patient 12, the insulin dose values, the insulin types, and the parameter values used by processor 102 to calculate future glucose values, supplemental insulin doses, and carbohydrate supplement amounts as well as such values, doses, and amounts. Such data along with a date and time for each measured glucose value and administered insulin dose value is stored in a data file 145 of memory 110 and/or 112. An included clock 144 of the collection device 24 supplies the current date and time to processor 102 for such use.

The collection device 24 further provides a user interface 146 such as, for example, buttons, keys, a trackball, touchpad, touch screen, etc., for data entry, program control, information requests, and the likes. In one embodiment, the user interface 146 comprises buttons 147, 149 for entry and navigation of the data provided in memory 110 and/or 112. In one embodiment, the buttons 147, 149 are used by the patient to enter (document) contextualizing information, such as data related to the everyday lifestyle of the patient 12 and to acknowledge that prescribed tasks are completed. Such lifestyle data may relate to food intake, medication use, energy levels, exercise, sleep, general health conditions and overall well-being sense of the patient 12 (e.g., happy, sad, rested, stressed, tired, etc.). Such lifestyle data can be recorded into memory 110 and/or 112 of the collection device 24 as part of the self-monitored data via navigating through a selection menu displayed on display 108 using buttons 147, 149 and/or via a touch screen user interface provided by the display 108. It is to be appreciated that the user interface 146 can also be used to display on the display 108 the self monitored data or portions thereof if made viewable as governed by the method according to the present invention which is discussed hereafter in later sections.

In one embodiment, the collection device 24 is switched on by pressing any one of the buttons 147, 149. In another embodiment, in which the biosensor 140 is a test-strip, the collection device 24 is automatically switched on when the test-strip is inserted into the collection device 24 for measurement by the measurement engine 138 of a glucose level in a sample of blood placed on the test-strip. In one embodiment, the collection device 24 can be switched off by holding down one of the buttons 147, 149 for a pre-defined period of time, or in another embodiment shut down automatically after a pre-defined period of non-use of the user interface 146.

An indicator 148 is also connected to processor 102, and operates under the control of processor 102 to emit audible, tactile (vibrations), and/or visual alerts/reminders to the patient of daily times for bG measurements and events, such as for example, to take a meal, of possible future hypoglycemia, and the likes. A suitable power supply 150 is also provided to power the collection device 24 as is well known to make the device portable.

The software 34 when received by the processor 102 of the collection device 24 is stored in main memory 110 (as illustrated) and/or secondary memory 112. The software 34 contains instructions, when executed by the processor 102, enables the processor to perform the features/functions of the present invention as discussed herein in later sections. In another embodiment, the software 34 may be stored in a computer program product and loaded by the processor 102 into cache memory to cause the processor 102 to perform the features/functions of the invention as described herein. In another embodiment, the software 34 is implemented primarily in hardware logic using, for example, hardware components such as application specific integrated circuits (ASICs). Implementation of the hardware state machine to perform the feature/functions described herein will be apparent to persons skilled in the relevant art(s). In yet another embodiment, the invention is implemented using a combination of both hardware and software.

In an example software embodiment of the invention, the methods described hereafter are implemented in the C++ programming language, but could be implemented in other programs such as, but not limited to, Visual Basic, C, C#, Java or other programs available to those skilled in the art or alternatively using script language or other proprietary interpretable language used in conjunction with an interpreter. Reference hereafter is also made to FIG. 4.

FIG. 4 depicts in tabular form a data file 145 containing data records 152 of self-monitored data 154 resulting from a structured collection procedure according to an embodiment of the present invention. The data records 152 (e.g., rows)

along with the self-monitoring data 154 (e.g., various one of the columns) can also provide associated therewith contextual information 156 (e.g., other various ones of the columns as well as via row and column header information). Such contextual information 156 can be collected either automatically, such as for example via input received automatically from the measurement engine, the biosensor, and/or any one of the other devices, or via input received from the user interface which was manually enter by the patient in response to a collection request (e.g., a question displayed by the processor 102 on the display 108) during the structured collection procedure. Accordingly, as such contextual information 156 can be provided with each data record 152 in a preferred embodiment, such information is readily available to a clinician and no further collection of such information is necessarily needed to be provided again by the patient either manually or orally after completing the structured collection procedure. In another embodiment, if such contextual information 156 and/or additional contextual information is collected after completion of a structured collection procedure according to the present invention, such information may be provided in the associated data file and/or data record 145, 152 at a later time such as via one of the computers 18, 25. Such information would then be associated with the self-monitored data in the data file 145, and thus would not need to be provided again orally or manually. Such a process in the latter embodiment may be needed in the situation where the structured collection procedure is implemented as or partly as a paper tool 38 which is used with a collection device incapable of running the software 34 implementing such a structured collection procedure.

It is to be appreciated that the date file 145 (or portions thereof, such as only the self-monitored data 154) can be sent/downloaded (wired or wireless) from the collection device 24 via the communication module 124 to another electronic device, such the external device 132 (PC, PDA, or cellular telephone), or via the public network 50 to the clinician computer 25. Clinicians can use the diabetes software provided on the clinician computer 25 to evaluate the received self-monitored data 154 as well as the contextual information 156 of the patient 12 for therapy results. An example of some of the functions which may be incorporated into the diabetes software and which is configured for a personal computer is the Accu-Chek® 360 Diabetes Management System available from Roche Diagnostics that is disclosed in U.S. patent application Ser. No. 11/999,968 filed Dec. 7, 2007, titled "Method and system for setting time block," and assigned to Roche Diagnostics Operations, Inc.

In a preferred embodiment, the collection device 24 can be provided as portable blood glucose meter, which is used by the patient 12 for recording self-monitored data comprising insulin dosage readings and spot measured glucose levels. Examples of such bG meters as mentioned above previously include but are not limited to, the Accu-Chek® Active meter and the Accu-Chek® Aviva system both by Roche Diagnostics, Inc., which are compatible with the Accu-Chek® 360° Diabetes management software to download test results to a personal computer or the Accu-Chek® Pocket Compass Software for downloading and communication with a PDA. Accordingly, it is to be appreciated that the collection device 24 can include the software and hardware necessary to process, analyze and interpret the self monitored data in accordance with predefined flow sequences (as described below in detail) and generate an appropriate data interpretation output. In one embodiment, the results of the data analysis and interpretation performed upon the stored patient data by the collection device 24, and if such stored patient data is designated as viewable as described hereafter in later sections, can be displayed in the form of a report, trend-monitoring graphs, and charts to help patients manage their physiological condition and support patient-doctor communications. In other embodiments, the bG data from the collection device 24, again if designated as viewable, may be used to generated reports (hardcopy or electronic) via the external device 132 and/or the patient computer 18 and/or the clinician computer 25.

The collection device 24 in other embodiments can further provide the patient 12, with at least one or more of the capabilities comprising: a) editing data descriptions, e.g., the title and description of a record; b) saving records at a specified location, in particular in user-definable directories as described above; c) recalling viewable records for display; d) searching viewable records according to different criteria (date, time, title, description etc.); e) sorting viewable records according to different criteria (e.g., values of the bG level, date, time, duration, title, description, etc.); and if permitted, f) deleting records; g) exporting records; and/or h) performing data comparisons, modifying records, and excluding records as is well known.

As used herein, lifestyle can be described in general as a pattern in an individual's habits such as meals, exercise, and work schedule. The individual additionally may be on medications such as insulin therapy or orals that they are required to take in a periodic fashion. Influence of such action on glucose is implicitly considered by the present invention.

It is to be appreciated that the processor 102 of the collection device 24 can implement one or more structured collection procedures 70 provided in memory 110 and/or 112. Each structured collection procedure 70 in one embodiment can be stand-alone software, thereby providing the necessary program instructions which when executed by the processor 102 causes the processor to perform the structured collection procedure 70 as well as other prescribed functions. In other embodiments, each structured collection procedure 70 can be part of the software 34, and can be then be selectively executed by the processor 102 either via receiving a selection from a menu list provided in the display 108 from the user interface 146 in one embodiment or via activation of a particular user interface, such as a structured collection procedure run mode button (not shown) provided to the collection device 24 in another embodiment. It is to be appreciated that the software 34, likewise, provides the necessary program instructions which when executed by the processor 102 causes the processor to perform the structured collection procedure 70 as well as other prescribed functions of the software 34 discussed herein. One suitable example of having a selectable structured collection procedure provided as a selectable mode of a collection meter is disclosed by in U.S. patent application Ser. No. 12/491,523, filed Jun. 25, 2009, titled "Episodic blood glucose monitoring system with an interactive graphical user interface and methods thereof," assigned to Roche Diagnostics Operations, Inc.

In still another embodiment, a command instruction can be sent from the clinician computer 25 and received by the processor 102 via the communication module 124, which places the collection device 24 in a collection mode which runs automatically the structured collection procedure 70. Such a command instruction may specify which of the one or more structured collection procedures to run and/or provide a structured collection procedure to run. In still another embodiment, a list of defined medical use cases or medical questions can be presented on the display 108 by the processor 102, and a particular structured collection procedure 70 can be automatically chosen by the processor 102 from a plurality of structured collection procedures (e.g., procedures 70a, 70b, 70c, and 70d) depending on the selection of the defined medical use cases or medical questions received by the processor 102 via the user interface 146.

In still another embodiment, after selection, the structured collection procedure(s) 70 can be provided through the computer readable medium 40 and loaded by the collection device 24, downloaded from computers 18 and/or 25, the other device(s) 132, or server 52. Server 52, for example, may be a healthcare provider or company providing such pre-defined structured collection procedures 70 for downloading according to a selected defined medical use case or question. It is to be appreciated that the structured collection procedure(s) 70 may be developed by a healthcare company (e.g. company 64) and implemented via the public network 50 through a webpage and/or made available for downloading on server 52, such as illustrated in FIG. 2. In still other embodiments, notices that a new structured collection procedure 70 is available for use on the collection device 24 to help address a particular use case/medical question that a user (e.g., healthcare provider and patient) may have can be provided in any standard fashion, such for via postal letters/cards, email, text messaging, tweets, and the likes.

In some embodiments, as mentioned above previously, a paper tool 38 can perform some of the functions provided by the diabetes software 34. An example of some of the functions which may be incorporated into the diabetes software 34 and which is configured as a paper tool 38 is the Accu-Chek® 360 View Blood Glucose Analysis System paper form available from Roche Diagnostics also disclosed in U.S. patent application Ser. No. 12/040,458 filed Feb. 29, 2007 entitled "Device and method for assessing blood glucose control," assigned to Roche Diagnostic Operations, Inc.

In still another embodiment, the software 34 can be implemented on the continuous glucose monitor 28 (FIG. 1). In this manner, the continuous glucose monitor 28 can be used to obtain time-resolved data. Such time-resolved data can be useful to identify fluctuations and trends that would otherwise go unnoticed with spot monitoring of blood glucose levels and standard HbA1c tests. Such as, for example, low overnight glucose levels, high blood glucose levels between meals, and early morning spikes in blood glucose levels as well as how diet and physical activity affect blood glucose along with the effect of therapy changes.

In addition to collection device 24 and software 34, clinicians 14 can prescribe other diabetes therapy devices for patients 12 such as an ambulatory insulin pump 46 as well as electronically based insulin pen 48 (FIG. 1). The insulin pump 46 typically includes configuration software such as that disclosed in the manual "Accu-Chek® Insulin Pump Configuration Software" also available from Disetronic Medical Systems AG. The insulin pump 46 can record and provide insulin dosage and other information, as well as the electronically based insulin pen 48, to a computer, and thus can be used as another means for providing biomarker data as requested by the structured collection procedure 70 (FIG. 2) according to the present invention.

It is to be appreciated that, and as mentioned above previously, one or more of the method steps discussed hereafter can be configured as a paper tool 38 (FIG. 1), but preferably all the method steps are facilitated electronically on system 41 (FIG. 2) or on any electronic device/computer, such as collection device 24, having a processor and memory as a program(s) residing in memory. As is known, when a computer executes the program, instructions codes of the program cause the processor of the computer to perform the method steps associated therewith. In still other embodiments, some or all of the method steps discussed hereafter can be configured on computer readable medium 40 storing instruction codes of a program that, when executed by a computer, cause the processor of the computer to perform the method steps associated therewith. These method steps are now discussed in greater detail hereafter with reference made to FIGS. 5A and 5B.

Create a Structured Collection Procedure

Figure 5A:
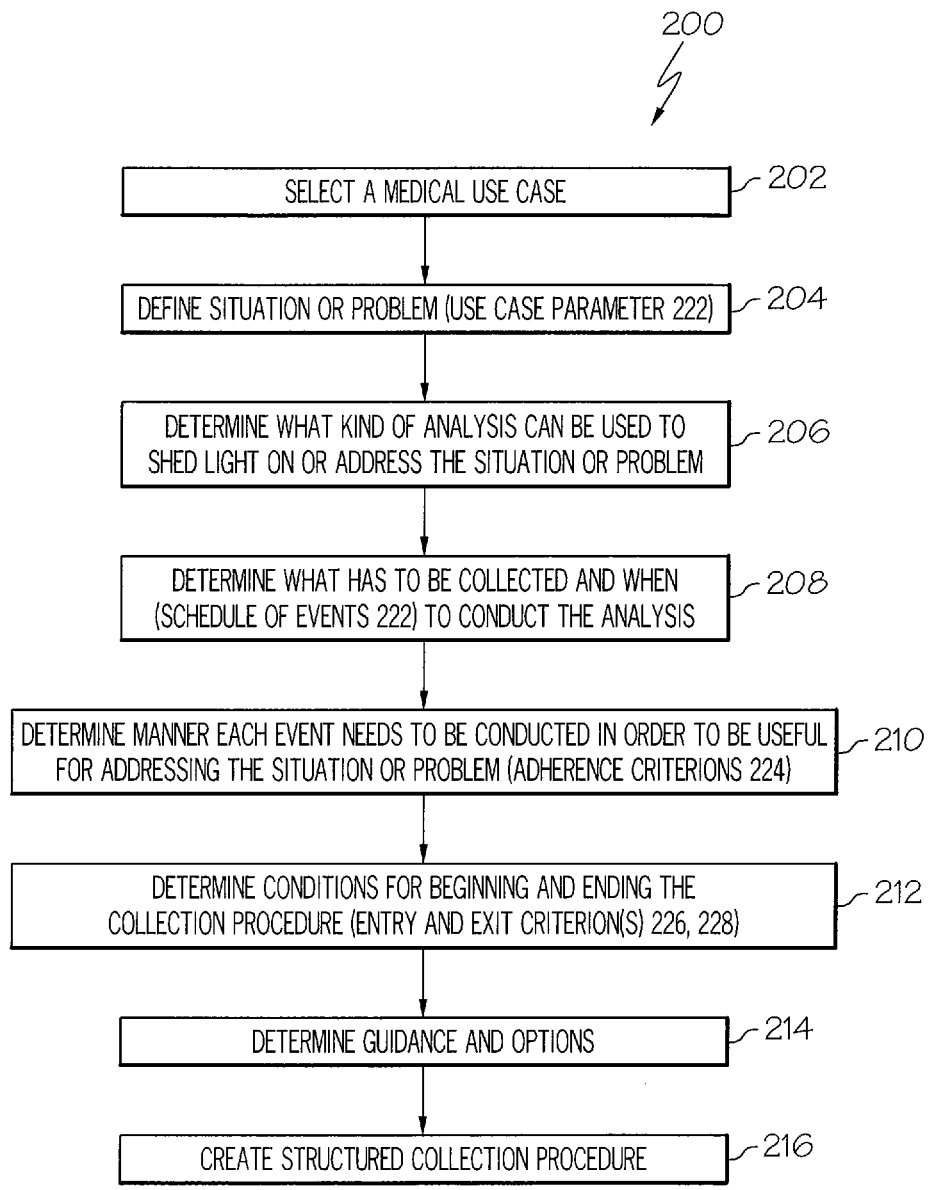
FIG. 5A depicts a method of creating a structured collection procedure for a medical use case and/or question according to an embodiment of the present invention.
Figure 5B:
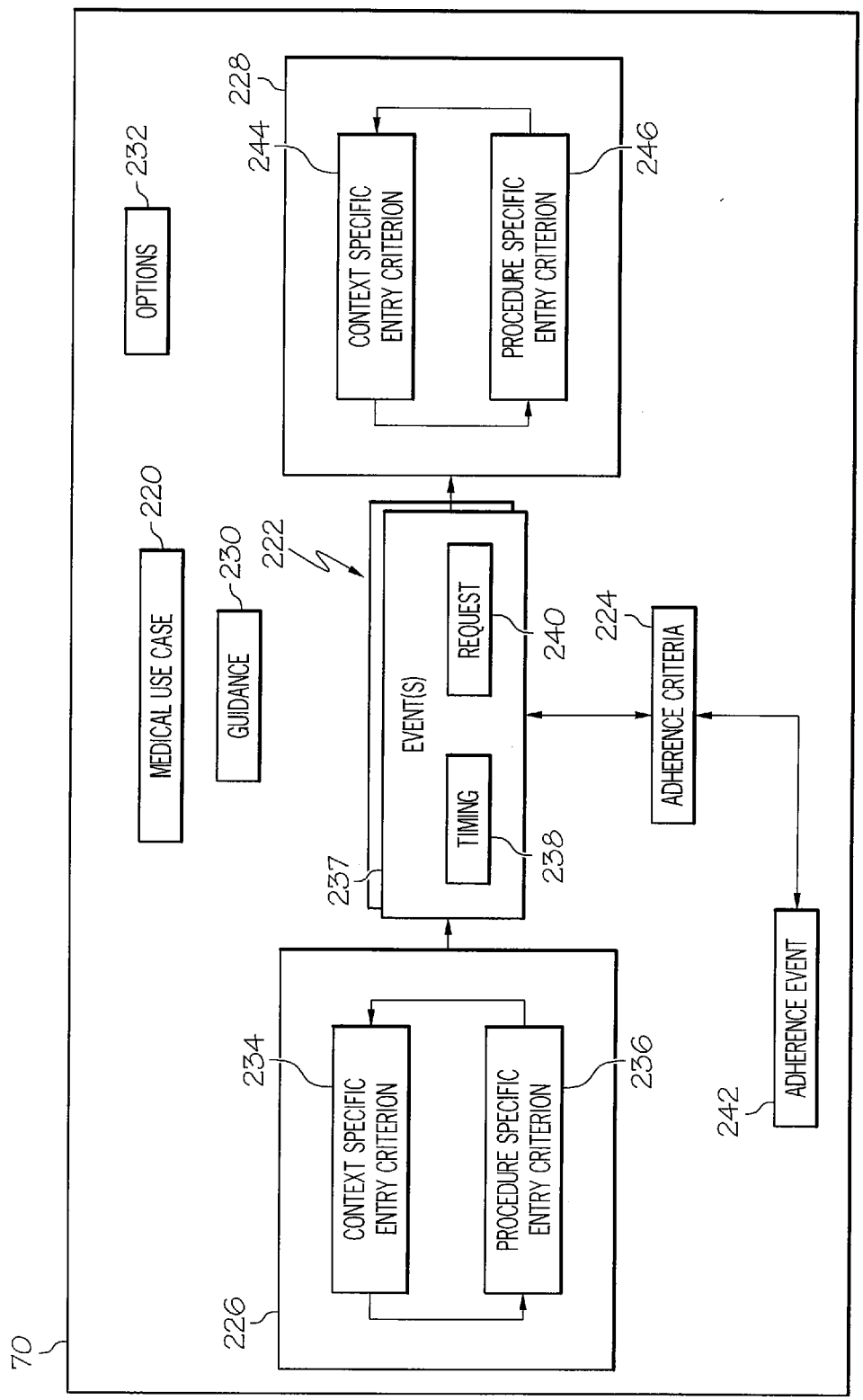
FIGS. 5B and 5C show parameters defining a structured collection procedure and factors which can be considered to optimize a patient's therapy using the structured collection procedure, respectively, according to one or more embodiments of the present invention.

FIG. 5A depicts a method 200 of creating a structured collection procedure 70 illustrated by FIG. 5B for a medical use case or question which may be implemented in any one of the above described devices 18, 24, 25, 26, 28, 36, 52 as stand alone software, as part of the diabetes software 34 or portions there of as part of paper tool 38. In step 202, a medical use case or question, hereafter referred to generally as use case(s), is selected and/or can be defined. It is to be appreciated that use cases may be, for example, questions concerning finding a diagnosis, how best to initialize therapy for a patient, finding a determination of status of a patient disease progression, finding the best ways to optimize a patient therapy, and the like. Still other examples can be providing such structured collection procedures 70 which can be used to help address medical questions regarding fasting blood glucose, pre-prandial glucose values, postprandial glucose values, and the like. Other medical questions can be to control the biomarker in a predefined context, to optimize the biomarker in a predefined context, related to therapy onset, type of therapy, oral mono-therapy, oral combination therapy, insulin therapy, lifestyle therapy, adherence to therapy, therapy efficacy, insulin injection or inhalation, type of insulin, split of insulin in basal and bolus, and the likes. For example, medical questions regarding oral mono-therapy and oral combination could include those involving sulfonylureas, biguanides, thiazolidinediones, alpha-glucosidase inhibitors, meglitinides, dipeptidyl peptidase IV inhibitors, GLP-1 analogs, taspoglutide, PPAR dual alpha/gamma agonists, aleglitazar. The selected use case can be assigned to a medical use case parameter 220 depicted in FIG. 5B.

Figure 5C:
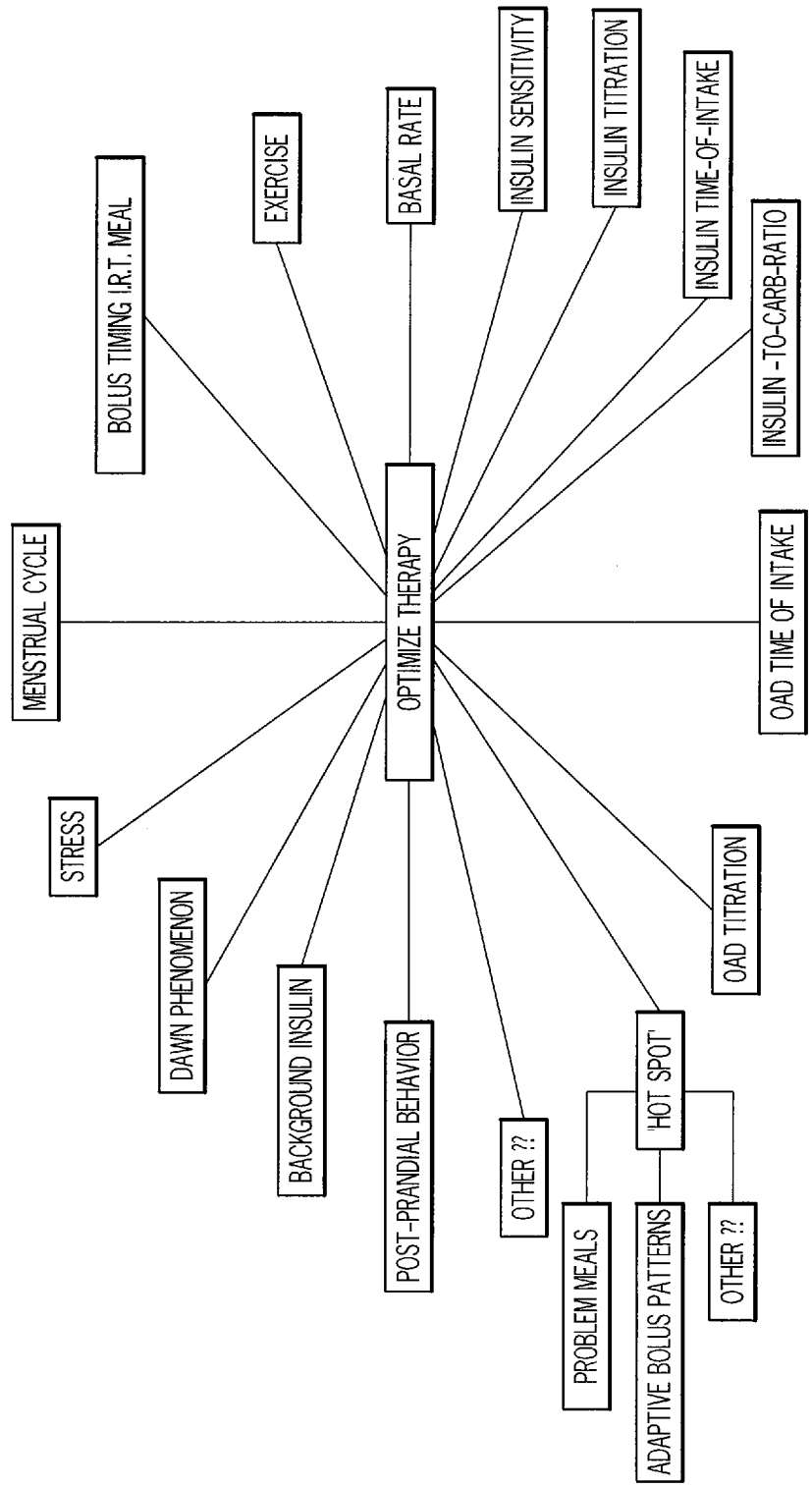

In step 204, the situation or problem surrounding the selected use case can be defined. This can be accomplished via looking at all the factors which may affect a change in the use case. For example, in the use case of desiring to know how best to optimize a patient's therapy some factors to look at may include stress, menstrual cycle, pre-dawn effect, background insulin, exercise, bolus timing with respect to a meal, basal rate, insulin sensitivity, post-prandial behavior, and the like such as shown by FIG. 5C.

In step 206, a determination can be made as to what kinds of analysis can be used to address or shed light on the situation or the problem. Such analysis may be, for example, selected from the following: evaluating the change in fasting blood glucose (FPG) values over the course of the structured collection procedure 70, monitoring one or more particular value over the duration of the structured collection procedure 70, determining an insulin to carbohydrate (I:C) ratio, determining insulin sensitivity, determining best time for administering a drug with respect to another variable, such as meal(s), and the like. In step 208, a sampling group determination can be made as to which information has to be collected, such as what biomarker(s) and the context(s) in which the biomarkers shall be collected, as well as when this information needs to be collected to conduct the analysis. For example, the sampling group can be defined as a string of data objects, each of which consists of: target type, e.g., time based which can use a target time (e.g., used for an alerting feature), a lower time window bound, an upper time window bound, etc., or data based which defines a data type (single, aggregate, or formula), the conditions for accepting the data (e.g., none, below a value, above a value, a formula, etc.), the type of collection (e.g., user input, sensor, data, etc.), as well as any reminder screen text (e.g., static, and/or dynamic in both formatting and value insertion) for each collection. The result of this process is a schedule of collection events 222 (FIG. 5B). Next in step 210, the manner in which each or a group of the schedule of collection events 222 is/are to be conducted in order to be useful for addressing the situation or problem of the selected use case is then determined. This results in one or more adherence criterions 224. In addition to and/or instead of the manner for performing a collection, the adherence criterion(s) 224 may also be based on one or more biomarker values falling into a pre-defined range or is equal to a certain pre-defined value. In other embodiments, the adherence criterion(s) can be a formula(s) which uses a biomarker datum or group of such data to determine if the resulting value falls into the pre-defined range or is equal to a certain pre-defined value.

For example, adherence criteria 224 can describe the parameters around the data collection events 237 that the patient 12 needs to perform such as tests within a certain window, fasting for a given amount of time, sleeping for a given amount of time, exercise, low stress, not menstruating, etc. As such, an adherence criterion 224 can establish the context of the information about to be provided. Adherence criteria 224 can also be used as mentioned above previously in another context to provide an assessment of whether the data is acceptable and when used in such a context may be referenced to as "acceptance" criteria. For example, before a sample is taken, the adherence criteria 224 can establish whether steps leading up to taking of the sample are accomplished. For example, the processor 102 in response to a request 240 displays the question, "Have you been fasting for the last 8 hours?", wherein a "Yes" response received by the processor via the user interface 146 meets the adherence criterion 224 for this step. In another example, after the sample is taken, the processor 102 can assess the received data for reasonableness using other adherence (acceptance) criterion(s). For example, based on prior data, a fasting bG sample should be between 120-180 mg/dl, but the received value was of 340 mg/dl, and thus fails such adherence (acceptance) criteria since being out of the predefined range for an acceptable value. In such an example, an adherence event 242 occurs wherein the processor 102 could prompt for an additional sample. In such a case, if the re-sampling fails too (i.e., not between 120-180 mg/dl), the assessment provided by the processor 102 is that the patient 12 has not fasted, and thus the processor 102 as instructed by the adherence criterion upon a failing of the re-sampling extend automatically the collection events 237 in the schedule of collection events 222 accordingly.

In still other embodiments, the adherence criteria 224 can be used as a logical switch to decide which data values to display and which one not to display according to a desired quality or characteristic of the data collected for each event 237. In one such embodiment, data values collected according to the schedule of collection events 222 which meet the defined adherence criterion(s) 224 of the collection procedure 70 can be designated automatically as viewable data by the processor 102 in the data file 145, or vice versa in another embodiment. For example, the adherence criteria 224 in the collection procedure 70 can be pre-defined, and/or customized by the clinician as desired, to display only those data values which have a desired event quality or characteristic, such as, e.g., those data values which fall into a desired range or vice versa, those data values that are a particular value or vice versa, those data values taken within a particular time window or vice versa, those data values taken at a certain time or vice versa, those data values which shows a desired variation between a particular number of previous data values collected from previous events 237 or vice versa, those data values which shows a desired rate of change between a particular number of previous data values collected from previous events 237 or vice versa, and combinations thereof. It is to be appreciated that providing such a logical switch via the use of the adherence criteria 224 in the collection procedure 70 provides the clinician with the flexibility to screen (i.e., filter) and display data values as needed in order to look at only particular data quality markers in the collected data values. Such a feature is also useful in a collection procedure 70 which collects a large amount of data values, such as one that may be carried out over a very long period of time (e.g., 7 days or more), or when the collection device 24 is a continuous glucose monitor 28 providing a large amount of data values (i.e., 1000 or more data values per day). A method of implementing such a display switching feature on the collection device 24 for a collected data value is discussed herein after in a later section.

Next in step 212, the condition(s) and context(s) in which the schedule of collection events 222 is to be started and ended can be determined. This results in one or more entry criteria 226 and exit criterions 228 being provided for the schedule of collection events 222 as well as possibly for a group of other schedule of events to which the schedule of collection events 222 belongs if providing a package of structured collection procedures, e.g., procedures 70*a*, 70*b*, 70*c*, and 70*d*, which may run concurrently and/or sequentially one after the other.

For example, the one or more entry criteria 226 can be used to determine whether the patient meets the conditions to use the collection procedure by the processor 102 checking that, for example, the patient 12 meets the entry criterion 226 based on current age being in a range, HbA1c being in a range, that the patient has a particular disease, has had the disease over a minimum period of time, has a Body Mass Index (BMI) in a range, had a Fasting Plasma Glucose (FPG) in a range, had a particular drug sensitivity, is taking a particular drug, taking a particular drug dosage, meets one or more prerequisites of another structured collection procedure, has completed one or more of another structured collection procedure, does not have one or more particular preconditions, e.g., pregnant, not fasting, or contraindications, e.g., feeling ill, feverish, vomiting, etc., and combinations thereof. Entry criterion 226 can also initiate the schedule of collection events 222 by an initiation event such as a time of day, a time of week, meal, taking a meal with a time offset, exercise, and exercise with a time offset, use of a therapeutic drug, use of a therapeutic drug with time offset, physiological circumstances, biomarker range, and biomarker within a pre-determined range calculated as an offset from a prior biomarker value. Example of a physiological circumstance can be that entry criterion will be met to start a structured collection procedure when a pre-determined number of a physiological event, e.g., hyperglycemia, hypoglycemia, a certain temperature at a certain of day, and the like, occur within a pre-defined amount of time, e.g., hours, day, weeks, etc. Accordingly, the entry criterion can be used to support the use of need to met prerequisites, indications for usage, and/or contraindications for usage. For example, an entry criterion 226 could define a prerequisite condition which in order for the structured collection procedure 70 to run an Insulin Sensitivity optimization, the processor 102 must verify first that a structured collection procedure for a Basal titration is completed and/or has a desired result and/or as well as another structured collection procedure for an insulin to carbohydrate ratio is completed and/or has a desired result. In another example, an entry criterion 226 could be defined with needing to meet certain indications for usage in which certain structured collection procedures could provide segregated uses for diabetics who are Type 1 vs. Type 2 as well as types of structured collection procedures which can be used to titrate for specific drugs. In another example, the entry criterion 226 could be defined with needing to meet certain contraindications for usage, in which for example, certain structured collection procedures 70 will not run if the patient 12 is pregnant, sick, etc.

Examples of the one or more exit criteria 228 can be based on the processor 102 determining that a particular value is reached, that a mean average of the primary samples values are in a range, that a particular event(s) and/or condition(s) have or have not occurred, and combinations thereof. Other conditions when the procedure may stop can include adverse events such as, for example, a hypoglycemic event, the patient is sick, the patient undergoes a therapy change, and the likes. Additional detail may also by provided by the processor 102 on the display 108 to the patient 12 based on what the specific exit criterion has been met. For example, in one example, if the patient 12 measures a glucose value indicating hypoglycemia, upon exiting the procedure, the processor 102 run automatically another alternative procedure which instructs the patient 12 to ingest carbohydrates and measure his blood glucose value every half an hour until the blood glucose exceeds 120 mg/dL. For this alternative procedure, the patient 12 can also be requested by the processor 102 to document his meals, activity, stress, and other relevant details to ensure that the conditions that led to hypoglycemia are recorded. The patient 12 may also be instructed by the processor 102 to contact the clinician 14 in this and other such special cases as deemed fit. Exit criteria can also include, for example, criterion for ending such as exiting after a successful completion, or exiting after an indeterminate completion, such as expiration of a predetermined timeout (logistical end), e.g., no result after n days, where n=1 to 365 days, or by termination e.g., exit with unsuccessful termination due to a fail-safe. It is to be appreciated that the structured collection procedure 70 can also be defined to end automatically not only based on meeting the exit criterion 228, but also when the patient 12 fails to perform a request to an acceptable level of compliance and/or when a patient physiological state has changed such that the patient is should not carry out the schedule of collection events 222, thereby failing adherence criteria 224, wherein the adherence event 242 is to end the structured collection procedure.

In step 214, guidance 230 for the user during collection can be determined as well as any options 232 for customizing the collection. For example, for guidance 230, the clinician 14 can use a default list of messages, or tailor messages to guide the patient 12 during execution of the structured collection procedure 70. As an example, one message could be provided on a successful data acquisition (i.e., meets the adherence criteria 224) would read, "Thank you. Your next scheduled measurement is at 12:30 pm." Alarms, such as provided by indicator 148, can also be associated with the structured collection procedure 70 that remind the patient 12 to take a measurement and can include a snooze functionality should the patient 12 need additional time to conduct the measurement. The snooze functionality as well as other device features is discussed further in later sections.

The result of steps 208-214 is the structured collection procedure 70 being created in step 216 which associates together the use case parameter 220, the schedule of collection events 222, the adherence criterion(s) 224, the entry criterion(s) 226, the exit criterion(s) 228, guidance 230, and the options 232. In one embodiment, at the time of generating a structured collection procedure 70 the clinician 14 also generates printed material (e.g., via computer 25) that explains to the patient the following aspects (at a minimum): the purpose of the structured collection procedure 70 and expected ideal outcome, i.e., setting a goal for the structured collection procedure 70; the structured collection procedure 70 design and the number of measurements needed; the entry criteria 226 that the patient 12 must satisfy before initiating the structured collection procedure 70 and before taking each reading; and the exit criteria 228 defining conditions under which device 24 will or the patient 12 should cease to continue the structured collection procedure 70. Such printed material as well as the guidance 230 that can be provided during the execution of the structured collection procedure 70 ensures that the patient is fully aware of why the data collection procedure is being carried out.

Examples, of the structured collection procedure 70 may be, for example, a structured collection procedure for determining an insulin-to-carbohydrate ratio, for determining bolus timing in respect to meal start, and for determining an exercise equivalent to ingested carbohydrates. In step 218, the structured collection procedure 70 is then made available for implementation and use in the system 41, such as in any of the above discussed manners mentioned with regards to FIGS. 1, 2, and 3. A structured collection procedure 70 accordingly may be provided via the above process, such as by either the medical community or healthcare companies 64, to help the clinician 14 address and/or investigate a defined medical use case or problem.

FIG. 5B shows the interactions of the parameters 222, 224, 226, and 228 of the structured collection procedure 70 for obtaining contextualized biomarker data from a diabetic patient to address a medical use case upon which the structured collection procedure is based. As mentioned above, the use case parameter 220 may be provided to identify the medical use case or question to which the parameters 222, 224, 226, and 228 address. For example, the processor 76 of the clinician computer 25, the processor 102 of the collection device 24, and/or the server 52 may read the medical use case parameters 220 from a plurality of structured collection procedures 70a, 70b, 70c, 70d (FIG. 2), such as provided on these devices and/or within the system 41, and provide a list of the available structured collection procedures, such as on the display 82 of the clinician computer 25 or the display 108 of the collection device 24. Additionally, the clinician computer 25, the patient computer 18, and/or the server 52 can use the medical use case parameter 220 for locating/sorting/filtering such structured collection procedures according to a medical use case(s).

As mentioned above, the entry criterion(s) 226 establishes the requirements for initiating the structured collection procedure 70 to obtain patient data which includes biomarker data, particularly, collected in a predefined context. In one embodiment, the processor 102 of the collection device 24 can use the entry criterion(s) 226 to determine when an associated structured collection procedure 70 is appropriate for the patient's physiological context and to ensure that all of the necessary inputs to the associated structured collection procedure have been established. Therefore, it is to be appreciated that the start date and/time of a structured collection procedure may dynamically change automatically by the processor 102 of the collection device 24 if the predefined condition(s) of the entry criterion(s) 226 is not satisfied. Accordingly, until the entry criterion 226 is satisfied, the start date and/time of the associated structured collection procedure 70 can be at some unknown time in the future.

For example, in one embodiment, a structured collection procedure 70 can be chosen automatically by the processor 102 from a plurality of structured collection procedures 70a, 70b, 70c, 70d, such as provided in memory 110 of the collection device 24, memory of the computers 18, 25 and/or from server 52, based on satisfying the condition(s) of a defined entry criterion 226 for an associated structured collection procedure. For example, in one embodiment, a first structured collection procedure, such as procedure 70d, is useful for showing trends in blood glucose levels ("bG Level Trending"). Therefore, an entry criterion 226 for the first structured collection procedure 70d may be for the patient to have a bG level mean which has elevated over a defined period (e.g., a past number of days, weeks, and months from the current date) above a certain pre-defined rate. For a second structured collection procedure, such as procedure 70a, its entry criteria 226 may require a particular number of bG measurement for a pre-breakfast measurement over a defined period (e.g., a past number of days, weeks, months, from the current date) being below a pre-defined bG value. In such an example, the processor 102 upon start up in one embodiment when commanded, such as via input received via the user interface, in another embodiment, or at a scheduled time as programmed by the software 34 in another embodiment, can run through the various entry criteria 226 provided by the various structured collection procedures 70a and 70d that are, for example, provided in memory 110 of the collection device 24 and determine whether the stated condition(s) for the entry criteria 226 of a particular structured collection procedure 70 is satisfied. In this example, the processor 102 determines that the historical data from past measurements in memory 110 indicate that the patient's bG level mean has been elevating, and that the entry criterion 226 for the first collection procedure 70d has been met, but not the entry criteria for the second structured collection procedure 70a. In this example, the processor 102 then automatically selects and starts the first structured collection procedure 70d based on the above-mentioned analysis.

It is also to be appreciated that the use of the entry criterion 226 can help to reduce the misallocation of medical expenses by assuring that the indications of use for the structured collection procedure 70 have been met before starting the schedule of collection events 222. The entry criterion 226 as well can help assure that any requests to perform multiple structured collection procedures do not overlap if incompatible, are not unnecessary repeats of each other, or provide a significant burden on the patient. In this manner, many of the noted problems in which a patient may avoid any further attempts to diagnose their chronic disease or to optimize therapy can be both addressed and avoided automatically by the processor 102 of the collection device 24 via use of the entry criterion 226.

As shown by FIG. 5B, the entry criteria 226 can include context specific entry criterion 234, procedure specific entry criterion 236, and combination thereof. Examples of context specific entry criterion 234 can include one or more variables to identify meals, low blood glucose events, insulin type and dosage, stress, and the like. In another example, the context specific entry criterion 234 can be defined such as in the form of a specific question(s), to which the processor 102 requires a specific answer to be received from patient via input from the user interface 146. For example, the processor 102 in executing the entry criterion 226 may display on the display 108 the question of whether the patient is willing and able to perform the structured collection procedure 70 over the required period. If the patient responses affirmatively via the user interface 146, then the entry criterion 226 has been satisfied and the processor 102 continues automatically with performing the collection events 237 according to the their associated timing as defined in the structured collection procedure 70. If the patient responses in the negative to the displayed question, then the processor 102 will not continue with the structured collection procedure 70, and may for example, re-schedule the asking of such a question to a future time, such as if designated by an options parameter.

Examples of procedure specific entry criterion 236 can include one or more variables to identify disease state, disease status, selected therapy, parameter prerequisites, insulin to carbohydrate ratio prior to testing insulin sensitivity, incompatible collection procedures, and the like. In one embodiment, the procedure specific entry criterion 236 can be defined such that the processor 102 will continue automatically with the structured collection procedure 70 with one of three initiators—the patient 12, the clinician 14, or data, e.g., if the condition(s) of the entry criterion 226 is satisfied. For example, the procedure specific entry criterion 236 can be satisfy if the clinician 14 has prescribed the structured collection procedure 70, such as via an authorized user entering via the user interface 146 a valid password to unlock the particular structured collection procedure for use, in one embodiment. In another embodiment, the clinician 14 can send the password or an authorization code from clinician computer 25 and/or server 52 to the collection device 24 which prescribes (authorizes) the structured collection procedure 70 for use by the patient 12 on the collection device 24. It is to be appreciated that one or more structured collection procedure 70 can be provided in memory 110 of the collection device 24 which cannot be used by the patient 12, and which can be also hidden from being viewed on the display 108, such as in a selection list, by the patient until authorized by the clinician 14. In still another embodiment, the clinician 14 can be also an authorized user, e.g., who can enter via the user interface 146 a valid password to unlock the particular structured collection procedure for editing, wherein the rights for editing and the rights can be differentiated by entering different passwords.

The procedure specific entry criterion 236 can be satisfied by a user for example, by the user selecting a particular structured collection procedure 70 from a listing of structured collection procedures 70a, 70b, 70c, 70d provided on the display 108. An example of a data initiated procedure for the procedure specific entry criterion 236 would be that a biomarker measurement(s) provided to the processor 102 indicates a certain condition which must have occurred or be present in order for the entry criteria 226 for the particular structured collection procedure to be satisfied. Such a condition, for example, can be the occurrence of a single event, such as a severe hypoglycemic event, or a series of events, such as hypoglycemic events within a given, a predetermined time frame, such as in 24 hours from a start time, in one week from a start time, etc., a calendar date-time, and the like. In still other embodiment, the entry criteria 226 for a particular structured collection procedure can be satisfied by also meeting a start time, e.g., a pre-defined time, calendar date-time, and the likes.

Accordingly, the entry criteria 226 can be a single criterion or multiple criteria that establish context and/or condition of the patient's physiology that are relevant to the medical use case being addressed by the structured collection procedure 70. In another embodiment, the entry criteria 226 can be assessed after patient data has been collected, such as, on historical patient data.

The schedule of collection events 222 specifies one or more collection events 237 which each comprises at least one or more variables defining a performance time or timing 238, the guidance 230 to perform the event, requests 240 for patient actions, which may include a request for information from the patient and/or a request for collection of at least one type of biomarker data from the patient, and combinations thereof. For performance time 238, the schedule of collection events 222 can specify timing of each collection event 237, such as for a biomarker sampling at a particular time on three consecutive work days, or one sample at time of wake-up, one sample thirty minutes later, and another sample one hour later.

The guidance 230 for each collection event 237 and for any criteria 224, 226, 228 may include, for example, providing electronic reminders (acoustic, visual) to start, end and/or wake up at a particular time, to perform a bG collection at a particular time, to ingest a particular meal or food(s) at a particular time, to perform a certain exercise(s) at a particular time, take medication at a particular time, and the like. Guidance 230 may also include information, questions and requests to record particular information about physiology, health, sense of well-being, etc., at a particular time, suggestion to improve compliancy with the collection procedure, encouragement, and positive/negative feedback.

It is to be appreciated that the collection events 237 define all the steps that are necessary to be preformed in advance of as well as after a biomarker sampling according to a request 240, such that a reproducible set of circumstances, i.e., context before and/or after the sampling, is created in the biomarker data for the biomarker sampling. Examples of such biomarker data, in the context of diabetes, include fasting blood glucose values, pre-prandial glucose values, postprandial glucose values, and the like. Examples of a set of circumstances can include data associated with the biomarker value which identifies collected information in the patient data about meals, exercises, therapeutic administration, sleep, hydration, and the likes.

Each of the collection events 237 in the schedule of collection events 222 can be time-based, event-based, or both. A collection event 237 can also be a start of a meal, a wake-up time, start of exercise, a therapeutic administration time, a relative offset used with a prior glucose value, or a time indicating movement above or below a predetermined biomarker value threshold. The collection events 237 can also include any required patient actions necessary to be performed in advance of and during biomarker sampling such that reproducible circumstances are created at the time of biomarker sampling. This can includes one or more of meals, exercise, therapeutic administration, sleep, hydration, and the like. Additionally, the collection events 237 in the schedule of collection events 222 can be adjusted (number, types, timing, etc.), to accommodate work schedule, stressors, and the like of the patient 12.

As mentioned above previously, the adherence criteria 224 is used to assess qualitatively whether a collection event 237 performed according to the schedule of collection events 222 provided data which is acceptable to addressing the medical use case upon which the structured collection procedure 70 is based. In particular, the adherence criteria 224 can provide variables and/or values used to validate data from a performed collection event 237. For example, an adherence criterion 224 can be a check performed by the processor 102 of the collection device 24 that a value collected in response to a collection event 237 is within a desired range, or is above, below, or at a desired value, wherein the value may be a time, a quantity, a type, and the like. The same or different adherence criteria 224 may be associated with each of the collection events 237 within the schedule of collection events 222 as well with the entry criterion(s) 226 in one embodiment, and as being the exit criterion 228 in another embodiment, such as illustrated by FIG. 6D (i.e., "stop exercising when bG back in target range" which defines both the adherence and exit criteria). In one embodiment, one or more collection events 237 in the schedule of collection events 222 may be modified (e.g., added, deleted, delayed, etc.) if a particular event or events fail to met the adherence criterion 224 for the particular event or events. In one embodiment, the meeting of an adherence criterion(s) 224 for a particular event 237 can trigger an adherence event 242. In one embodiment, upon occurrence of an adherence event 242 due to the associated adherence criterion(s) 224 for a collection event 237 being met or satisfied, the processor 102 sends automatically a message to the clinician 14 notifying him or her of the patient 12 meeting the associated adherence criterion(s) in one embodiment as well as providing the context data associated with the meeting of the adherence criteria 224 in still another embodiment. In another embodiment, the failure of the adherence criterion(s) 224 for a particular event can trigger an adherence event 242. In one embodiment, upon occurrence of an adherence event 242 due to the associated adherence criterion(s) 224 for a collection event 237 not being met or satisfied, the processor 102 sends automatically a message to the clinician 14 notifying him or her of the failure of the associated adherence criterion(s) in one embodiment as well as any context data associated with the failure of the adherence criteria 224 in still another embodiment. In yet another embodiment, upon occurrence of an adherence event 242 due to the associated adherence criterion 224 for a collection event 237 not being met or satisfied, the processor 102 may be required one or more additional actions as a consequence. For example, the processor 102 may prompt on the display 108 additional information to the patient, and/or prompt a question to determine whether the patient 12 is sick, stressed, or unable to perform the request e.g., eat the meal, or exercise. If the patient answers "Yes", e.g., via the user interface 146, then as part of the adherence event 242 the processor 102 can provide a delay to the schedule of event (i.e. suspend). In one embodiment, the delay can continue until the patient indicated that he or she is better in response to another question prompter by the processor 102, such as the next day or after a predefined amount of time as also part of the adherence event. For example, the patient 12 is prompted by the processor 102 to administer a drug, but the patient is not at home, such as for example, where his/her insulin is located. The patient 12 can select the delay via the user interface 146, wherein the processor 102 re-prompts the patient after a predetermined amount of time. This delay may also have an upper limit in which if the schedule of events is not re-started within a certain amount of the time, the structured collection procedure 70 in such a circumstance may just end. In another embodiment, another form of an adherence event is a violation event, which results when the person executing a structured collection procedure 70 fails to make a recommended change in response to a request. For example, the request may be for the patient to adjust a drug dosage from 10 U to 12 U, wherein the patient answers in the negative to a question on the displayed on the display 108 asking if the patient will or has complied with such a change. In response to such a violation event, the processor 102 may also send a message, for example, to the clinician 14, and/or provide a delay as previously discussed above concerning the adherence event.

In another example and in one embodiment, a bG measurement must be collected before each meal in order for a structured collection procedure 70 to provide data that is useful in addressing the medical use case or question for which it was designed, such as identified by the use case parameter 220. If, in this example, the patient fails to take a bG measurement for the lunch meal in response to a request 240 for such a collection according to the timing 238 of the collection event 237, and hence the adherence criteria 224 for that collection event 237 fails to be satisfied, the processor 102 in response to the associated adherence event 242 can be programmed according to instructions in the structured collection procedure 70 to cancel all remaining collection events 237 in the schedule of collection events 222 for that day, mark the morning bG measurement stored in the data file (such as data file 145 (FIG. 4) as invalid, and reschedule the schedule of collection events 222 for the next day. Other examples of further actions in which the processor 102 may take in response to an adherence event 242 may be to dynamically change the structured collection procedure by switch to a secondary schedule of event, which may be easier for the patient to perform, provide additional events for measurements to make up the missing data, change the exit criteria from a primary to a secondary exit criterion providing modified criterion(s), change the adherence criteria from a primary to a secondary adherence criterion, fill in the missing data for the failing event with (an estimate from) historical data, perform a particular calculation to see if the structured collection procedure 70 can still be successfully performed, send a message to a particular person, such as a clinician, of the failing event, provide a certain indication in the associated data record 152 to either ignore or estimate the missing data point, and the likes. In still another embodiments, the adherence criteria 224 can be dynamically assessed, such as for example, based on one or more biomarker values and/or input received from the user interface in response to one or more questions, via an algorithm which determines whether the collected data provides a value which is useful in addressing the medical use case or case. In this example, if the calculated adherence value is not useful, for example, does not fall into a desired range or meet a certain pre-define value, then further processing as defined by the resulting adherence event would then take place, such as any one or more of the processes discussed above.

The exit criteria 228 as mentioned previously above establishes the requirements for exiting or completing the structured collection procedure 70. In one embodiment, the exit criteria 228 can be used to ensure that the structured collection procedure 70 has adequate contextual data to answer the medical question addressed by the structured collection procedure 70. In such an embodiment, the exit criterion 228 thus can help increase the efficiency of the structured collection procedure 70 by minimizing the number of required samples needed to address the medical use case. By "addressing", it is meant that sufficient patient data has been collected in which the clinician 14 may render an assessment to the medical use case. In other embodiments, the assessment may be indicated by a given confidence interval. A confidence interval is a group of discrete or continuous values that is statistically assigned to the parameter. The confidence interval typically includes the true value of the parameter at a predetermined portion of the time.

As with the entry criteria 226, the exit criteria 228 can comprise one or more of context specific exit criterion 244, procedure specific entry criterion 246, and combinations thereof. Examples of context specific exit criterion 244 can include one or more variables to identify mood, desired blood glucose events (i.e., blood glucose level), to indicate stress, illness, contraindications, such as for example, hyperglycemia, hypoglycemia, vomiting, a fever, and the likes. Examples of procedure specific entry criterion 246 can include one or more variables to identify a number of events meeting the adherence criteria, biomarker values being in a desired pre-determined range and/or at a desired pre-determined value, a desired disease state, desired disease status, no change in the biomarker after a pre-determined period, or no significant progress over a pre-determined period to a desired biomarker value, a predefined date-time, and the like. It is to be appreciated that in one embodiment the exit criterion 228 can establish the condition(s) needed to be met for entry criterion 226 of a second structured collection procedure 70. For example, upon having a suitable Insulin-to-Carbohydrate (I:C) determined with a first collection procedure, such as for example, structured collection procedure 70*b* (FIG. 6B), running a structured test for determining the best time for administering a bolus in regards to a start of a meal, such as for example, structured collection procedure 70*c* (FIG. 6C), which needs a current I:C ratio, can be conditioned such that the processor 102 can implement automatically a schedule of events of the second structured collection procedure 70*c* upon meeting the exit criterion of the first structured collection procedure 70*b*, which can be in one particular embodiment, after a pre-defined date-time, or in another embodiment at some unknown time if the conditions for meeting the exit criteria is dependent on non-date time condition(s). For example, the exit criterion 228 of a first structured collection procedure 70 that is being run by the processor 102 according to the schedule of collection events 222 and the entry criterion 226 of the second structured collection procedure 70 both can be based on the same one or more contraindications, such as mentioned above. In such an embodiment, upon occurrence of a contraindication being provided to and/or detected by the processor 102, such as via the user interface 146 and/or the biosensor 140, respectively, which in this example meets the exit criterion 228 of the first structured collection procedure 70, the processor 102 would automatically start the schedule of events of the second structured collection procedure 70 as the entry criterion 226 of the second structured collection procedure 70 has also been met. An example of such a second structured collection procedure 70 which can be started via exiting a first structured collection procedure can be one which has a schedule of collection events 222 which requests a biomarker samplings at a routine interval, e.g., every 30 minutes, every hour, every day at a particular time, etc., until the contraindication(s) clears (e.g., biomarker value(s) reaches a desire range or value, patient 12 indicates to processor 102 via user interface 146 no longer having a contraindication(s), expiration of a predefined period, etc.). Such an embodiment is useful if recording the context and values of the events after the occurrence of the contraindication(s) is a desire and in which the first collection procedure should be exited when a contraindication(s) occurs.

The exit criteria 228 can be a single criterion or multiple criteria that establish the conditions to exit the structured collection procedure 70. The conditions are provided in a preferred embodiment such to ensure that adequate contextualized biomarker data has been obtained to answer the medical question being addressed by the collection method. For example, such that a predetermined number of valid samples have been acquired, or that the variability in the samples is below a predetermined threshold. Therefore, in such an embodiment the end date and/time of the structured collection procedure 70 may be dynamic and be changed automatically by the processor 102 if the predefined condition(s) of the exit criterion(s) 228 is not satisfied. Likewise, in another embodiment, the conditions of the exit criterion 228 may be dynamic and be changed automatically be the processor 102 such for example if a particular adherence criterion 224 is satisfied or not satisfied. For example, in one embodiment if adherence criterion 224 for a particular collection event 237 is met, then the processor 102 is instructed to use a first exit criterion and if not met, then the processor 102 is instructed to use a second exit criterion that is different from the first exit criterion. Accordingly, until the exit criterion 228 is satisfied in such embodiments, the end date and/or time of the structured collection procedure 70 can be at some unknown time in the future. In another embodiment, the exit criteria 228 can be assessed after patient data has been collected, such as, on historical patient data.

It is to be appreciated that the entry and exit criteria 226, 228 together with the adherence criteria 224 can help to reduce both the time to perform the structured collection procedure 70 and the expense associated with the collection by defining one or more of the acceptable conditions, values, structure and context needed to perform the schedule of collection events 222 in an effort to make every collection event 237 count and/or reduce consumption of test strips 30 with unneeded collections that do not help address the medical use case or question. Hereafter reference is made to FIGS. 6A-6E.

Structured Collection Procedure Examples

FIGS. 6A-E illustrate examples of some structured collection procedures 70a, 70b, 70c, and 70d depicting their functions which can easily be translated by one of ordinary skill in the related art into instruction code which may be implemented on any one of the devices the above described devices 18, 24, 25, 26, 28, 36, 52. Therefore, for brevity, no discussion is provided concerning pseudo-code or actual code relating to these illustrated functions.

Figure 6A:
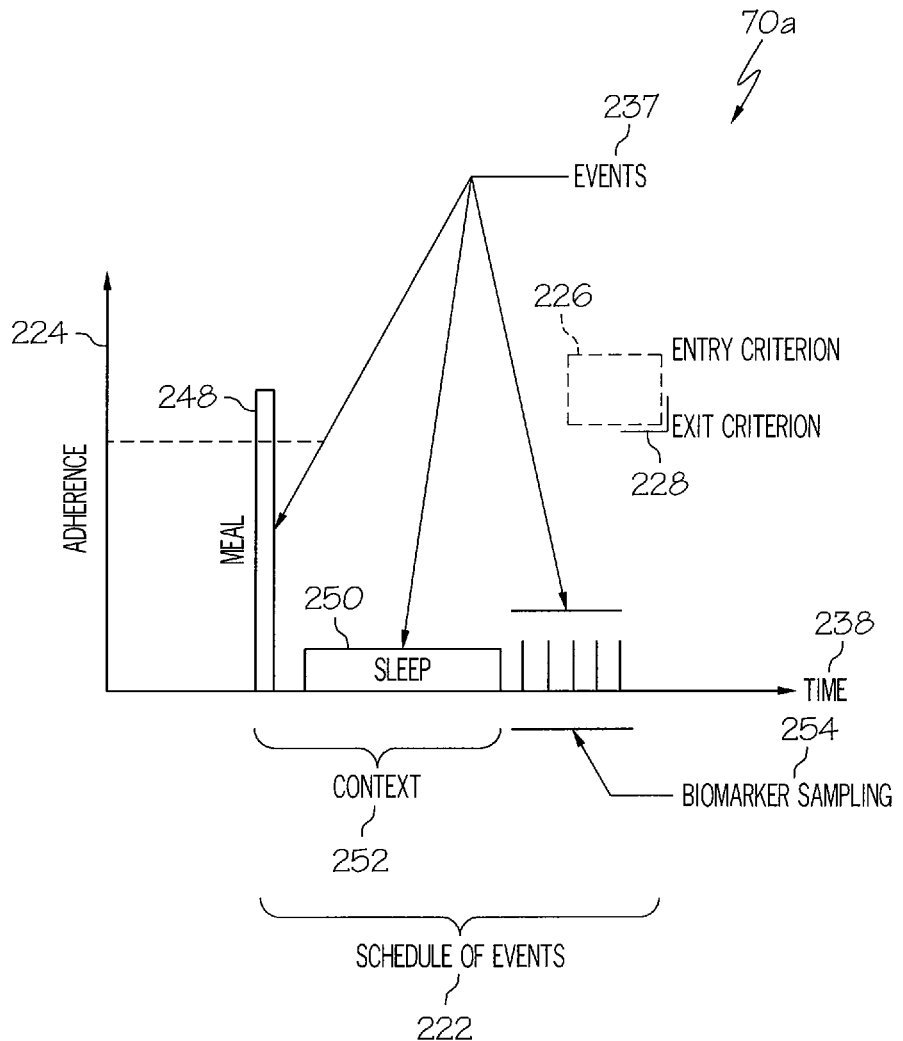

FIG. 6A diagrammatically illustrates an embodiment of a structured collection procedure 70a used to obtain contextualized biomarker data from a diabetic patient. The horizontal axis shows the performance times 238 of the various collection events 237, and the vertical axis shows adherence criterion 224 without values. In the illustrated embodiment, the collection events 237 can include recording information regarding a meal 248 and sleep 250 in which to provide context 252 for the five-biomarker samplings 254 also collection events 237 that are part of the schedule of collection events 222. In this example, the adherence criterion 224 for the meal 248 can be a value which must be greater than a minimum value, e.g., for a carbohydrate amount. The entry criterion 226, for example, can comprise a biomarker value being above a particular value such as required to meet contextualization requirements to begin the structured collection procedure 70a. The exit criterion 228 as well can comprise a biomarker values being below a particular value such as also required to meet contextualization requirements to end the structured collection procedure 70a. Such a structured collection procedure 70 is useful for helping to address a number of medical use cases.

GLP1 Structured Collection Procedure

For example, several epidemiological studies have confirmed that elevated postprandial glucose (PPG) levels are a significant predictor of cardiovascular mortality and morbidity in type 2 diabetes (T2D). For this reason, there is a family of human once-weekly long acting glucagon-like peptide-1 (GLP 1) drugs which can be prescribed to T2Ds who show high post prandial bG values. These GLP 1 drugs are similar to the natural hormone GLP-1 which has a key role in blood sugar regulation by stimulating insulin secretion and suppressing glucagon secretion. Therefore, a structured collection procedure 70 can be provided in one embodiment which proposes an intensive measurement of bG values during the time after one or more meals over time allows therapy efficacy to be shown by means of observed reduced postprandial bG values. Based on such observed values, doses recommendation for a GLP 1 drug and/or whether a particular GLP 1 drug is the right drug at all for the patient can be determined.

For example, the structured collection procedure 70 could be provided on a collection device 24 for when a patient has been prescribed to administer a particular drug, e.g., a GLP 1 drug. In the case of a GLP 1 drug, in which determination of drug efficacy is desired, the entry criterion 226 for such a structured collection procedure could then be that the patient must affirm to the processor 102 in response to a question displayed on the display 108 to perform the structured collection procedure 70 over a period of time (e.g., over the next 4 to 24 weeks) and/or the processor 102 has determined that the mean PPG level of the patient from prior post prandial bG values over a period (e.g., week, month, etc.) are high (e.g., greater than 141 mg/dl). Still other factors could be used as the entry criterion(s) 226, such as fasting blood glucose being more than a certain value, e.g., 126 mg/dl or less than a certain value, e.g., 240 mg/dl.

After the conditions of the entry criterion(s) 226 have been satisfied and confirmed by the processor 102, the schedule of collection events 222 is then automatically run by the processor 102. The schedule of collection events 222 would specify desired collection events 237 in which the processor 102 would automatically prompt the patient for entering post prandial bG values after breakfast, lunch, and dinner (i.e., performing a bG measurement on a sample provided to a test strip that is read by the measurement engine and provided to the processor for storing in a data record and display). As customized by the prescribing clinician, the schedule of collection events 222 could also define a collection event 237 with a performance time 238 in which the patient must administer the drug as well as to provide a reminder of the dosage and a request 240 for confirmation from the patient when the drug has been administered. For example, the processor 102 in executing the schedule of collection events 222 would automatically prompt the patient to administer dosages at the times specified by the collection events 237 in the schedule of collection events 222, e.g., 10 mg of Taspoglutide on a certain day of the week, and then after a period, a second dosage according to a second interval, e.g., after 4 weeks, then 20 mg also on a certain day of the week. A collection event 237 could also be defined in the schedule of collection events 222 in which the processor 102 makes a request on the display 108 for information, such as whether the patient is feeling well, to provide an indication of energy level, to provide an indication of size of meals consumed, and the like.

A condition(s) for the adherence of each entered post prandial bG value could be provided via the use of adherence criteria 224 in which any post prandial bG value entered (i.e., measured) an amount of time before or after the prompting, e.g., a testing window of ±30 minutes, such a measured value would not be accepted as a valid measurement for the schedule of collection events 222 by the processor 102. In one embodiment, the processor 102 can take further action automatically based on the adherence criteria 224 assessment preformed automatically by the processor 102. For example, if a bG measurement was taken before a measurement prescribed by a collection event in the schedule of collection events 222 and outside the defined testing window, e.g., −30 minutes before the collection event time, the processor 102 in such a case will automatically notify the patient that a measurement is still needed at the prescribed time as the previous measurement was not accepted since outside the testing window. Likewise, if after the testing window, e.g., the collection event time+30 minute, the processor 102 can automatically notify the patient that the previous measurement was not accepted since outside the testing window and provide encouragement on the display 108 to the patient to make an effort take a measurement within the testing window.

The exit criterion 228 for such a GLP 1 structured collection procedure 70 could be an indication that the mean bG value, in using a minimum amount of time (e.g., days, weeks, months, etc.), a minimum number of accepted measurements, or both, has reached a desire value. Likewise, the exit criterion 228 could be an indication that the mean bG value, after a maximum amount of time (e.g., days, weeks, months, etc.), a maximum number of accepted measurements, or both, has not reached a desire value. Still further, the exit criterion 228 can be other factors which indicate that the drug or dosage is not at all right for the patient, such as the patient responding as having nausea and/or vomiting each day for a minimum number of days in response to a collection event for such information prompted by the processor 102 on the display 108. Still other factors could be used as the exit criteria 228, such as fasting blood glucose being less than a certain value, e.g., 126 mg/dl or greater than a certain value, e.g., 240 mg/dl. The data collected from such a drug base structured collection procedure 70 can then be used by a clinician to make a dosage recommendation for the GLP 1 drug and/or determine whether the particular GLP 1 drug is the right drug or not for the patient.

Figure 6B:
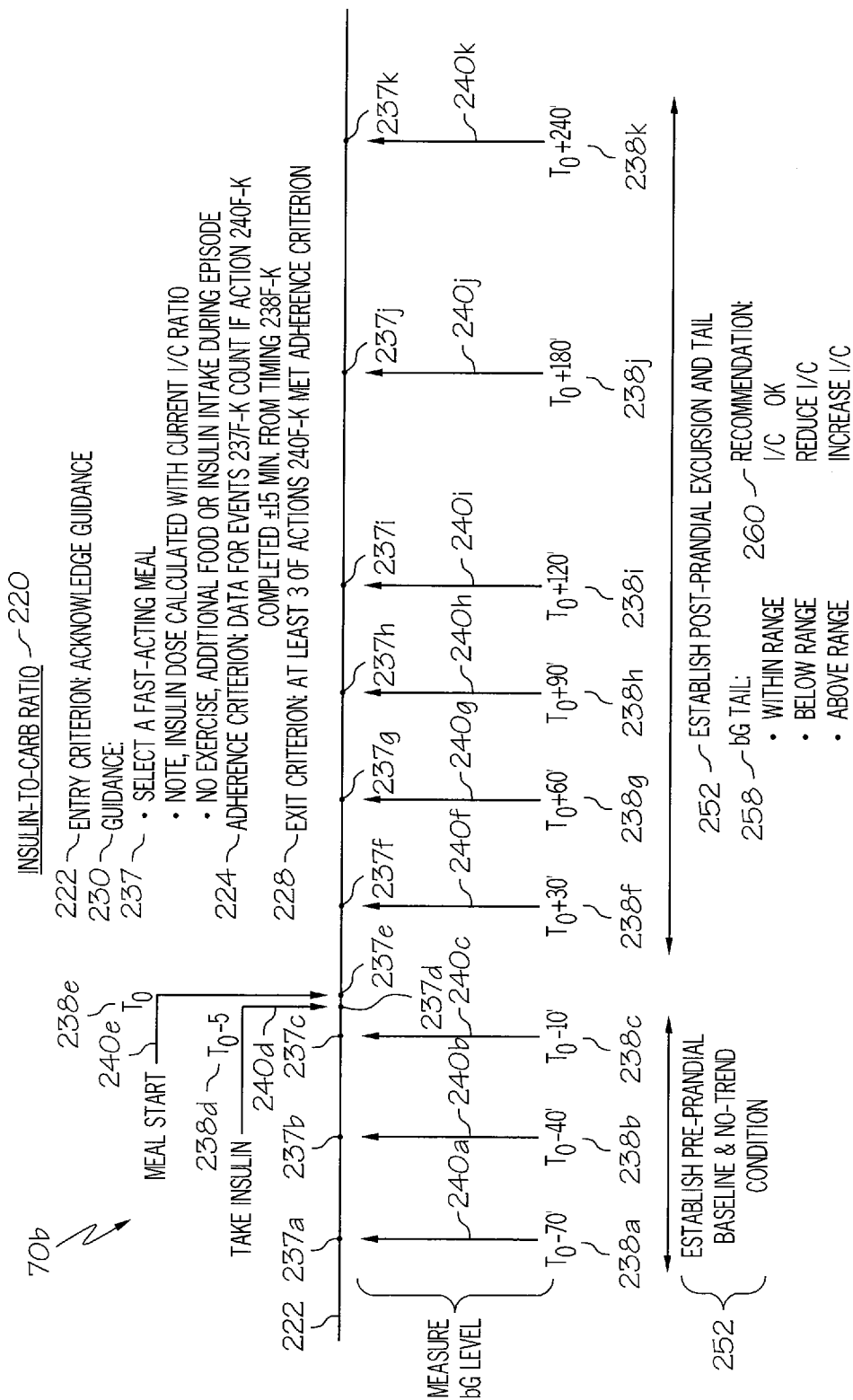
Figure 6D:
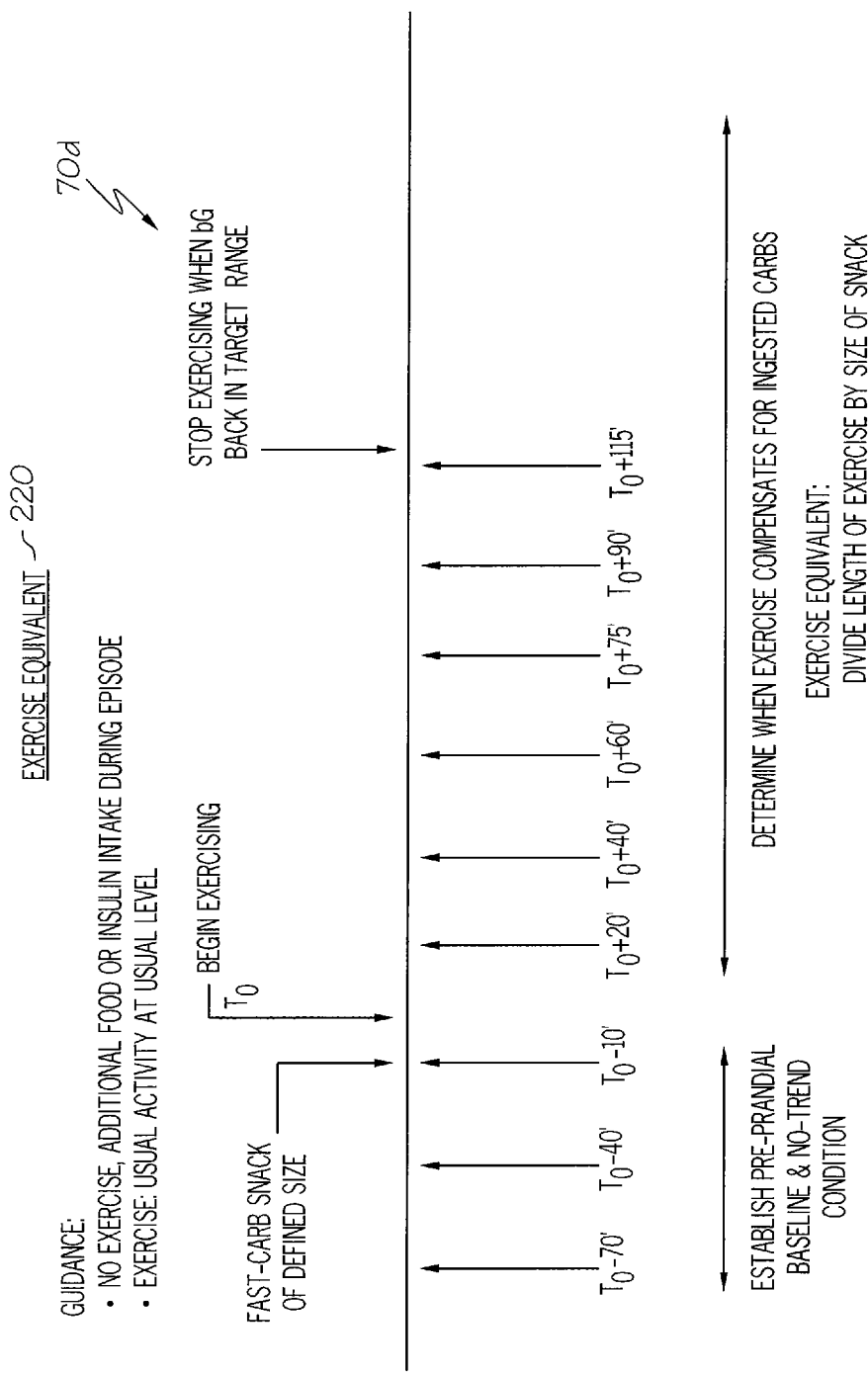

Another example is diagrammatically depicted by FIG. 6B which shows a structured collection procedure 70b which has a defined medical use case parameter 220 indicating that the procedure can be helpful for determining suitability of an insulin to carbohydrate (I:C) ratio. As illustrated, the entry criterion 226 is defined as having the patient simply acknowledge guidance 230 of selecting a fast-acting meal, to note that the insulin dose is calculated with the current I:C ratio as well as agreeing not to exercise, take additional food or insulin during the testing period. For example, the processor 102 can present on the display 108 such guidance 230, which the user can then acknowledge after reading with either a "Yes" or a "No" entered via using the user interface 146 for the desired entry choice. If the user enters "Yes", then the entry criterion 226 is satisfied, and the processor 102 automatically starts the schedule of collection events 222 defined in the structured collection procedure 70b. In another embodiment, the entry criterion 226 may be or include satisfying a request 240 for selecting a fast-acting meal. For example, the request 240 for selection can be the processor 102 displaying on the display 108 a selection menu providing a listing of fast-acting meals to which input of such a selection via the user interface 146 is needed. For example, selection of a fast-acting meal may be made via a press of one of the buttons 147, 149 or via the touch screen interface if provided by display 108. Such a selection can then be stored in memory 110 of the collection device 24 such as setup data 163 (FIG. 4) which may be part of the data file 145 (FIG. 4) for the structured collection procedure 70b. In an alternative embodiment, a particular fast-acting meal may be recommended by the structured collection procedure 70b.

As shown, the schedule of collection events 222 can comprise one or more events, such as the plurality of collection events 237a-k illustrated and with each having associated performance times 238a-k and requests (for action) 240a-k. As shown, the requests for action 240a-c and 240f-k are requests for the user to take a bG level measurement, request 240d is to take an insulin dose, and request 240e is to eat the fast acting meal. Also shown is that events 237f-k each have an adherence criterion 224, which must be met if the data for events 237f-k are to be recorded in the data file 145. In this example, the adherence criteria 224 requires that the requests 240f-k be completed within ±20 minutes of their corresponding performance times 238f-k in order for a data record 152 recording the received value(s) for the corresponding collection event 237f-k to count towards completing the structured collection procedure 70b. In one embodiment, the processor 102 will make each of the requests 240a-k at their associated performance times 238a-k in order to obtain resulting data values e.g., data 256a-k (FIG. 4) at the time the requests are performed.

For example, the processor 102 can prompt the patient 12 with a request 240a to take a bG level (biomarker) measurement at performance time 238a. The resulting measurement when received by the processor 102, such as automatically from the measurement engine 138 after reading the test strip (bio sensor) 140 for the desired biomarker, is then recorded automatically by the processor 102 in the date file 145 as a corresponding data value 256a for the associated collection event 237a. For requests 240d and 240e, at a required time, the processor 102 can automatically prompt the patient 12 to take the prescribed action at the required time, and again automatically prompt the patient thereafter to confirm that the required action has been taken, or that a predefine status has been achieved. A date-time stamp 169 can also be provided in the date record 152 automatically by the processor 102 upon triggering of the requests 240a-k, acknowledgement of the requests 240a-k, upon completion of the collection event 237a-k, upon receiving a data value 256a-k for the collection event 237a-k, and combinations thereof. Additionally, in another embodiment, the patient 12 can record data values 256a-k for one or more collection events 237a-k by entering the data directly into the collection device 24 via the user interface 146, wherein the processor 102 stored the entered data values/information in the associated data record 152 for the collection event 237a-k, or in other embodiments can record a voice message with the information for later transcription into digital data. In still other embodiments, the patient 12 can be guided by the collection device 24 to record data for a collection event 237a-k using a paper tool 38.

As mentioned previously above, each collection event 237 can be a recording of a biomarker value, or a request for a required patient action that is necessary in order to create a context for the biomarker value, such as for example, meals, exercise, therapeutic administration, and the like. In the illustrated embodiment, the context 252 for completing collection events 237a-c is to establish a pre-prandial baseline and a no-trend condition, and for collection events 237f-k to establish a post-prandial excursion and tail. Such context 252 for these events may also be associated with the corresponding data records 152 for each event as contextual information 156 (FIG. 4). Such information is useful later when reconstructing the data and/or when there is a desire to know the context for which the data record was created.

It is to be appreciated that any patient action taken outside of the required requests 240a-k can also be recorded by the processor 102 but will not be considered by the processor 102 as part of the structured collection procedure 70b. Data 256a-k for collection events 237a-k that are prospective can be identified based on a type of event, the time of the event, the trigger of the event, and combination thereof. Each of the performance times 238a-k can be fixed or variable based on prior data. Some of the collection event 237a-k in other embodiments can also be a past, current, or a future event such as for meals, exercise, and the like, or data values such as for hypoglycemic events, hyperglycemic events, or data of a specific value of interest. In some embodiments, the collection events 237a-k can be identified via a paper tool 38 that is procedure based.

As also shown, the structured collection procedure 70b will end if the condition of the exit criterion 228 is satisfied. In this example, the exit criterion 228 is satisfied if at least three of the requests 240f-k met the adherence criterion 224. For example, the processor 102 may provide a unique identifier 167 (e.g. a unique identifier (e.g. one or more numbers, letters, and/or characters which will only appear once in the data file to identity data associated therewith, e.g., an incremental count, pointer, etc.) (FIG. 4) in the data file 145 for each collection event 237a-k performed and to which satisfied the adherence criterion 224 if required. In the illustrated embodiment of FIG. 4, collection events 237a-c and 237e-k each receive a unique identifier but not collection event 237d, e.g., <null>, since not satisfying an associated adherence criteria (not shown). In addition, analysis logic 258 and resulting recommendations 260 can also be provided in the structured collection procedure 70b which the processor 102 may apply automatically to the data collected upon satisfying the exit criterion 228 in one embodiment.

Similar features are also provided in the examples illustrated by FIGS. 6C and 6D, wherein FIG. 6C depicts a structured collection procedure 70c which has a defined medical use case parameter 220 indicating that the procedure is helpful for determining suitability of a bolus in regards to a meal start. Likewise, FIG. 6D depicts a structured collection procedure 70d which has a defined medical use case parameter 220 indicating that the procedure is helpful for determining suitability of an exercise equivalent to a carbohydrate intake. In addition to the above examples, other such structured collection procedures may be designed to address other various medical use cases such as, for example, the following: determining the effects of eating a particular food on a biomarker level of a patient; determining the best time to take medication before and/or after a meal; and determining the affect of a particular drug on a biomarker level of a patient. Still other structured collection procedures can be provided which may be useful in addressing questions concerning how best to initialize therapy for a patient, finding a determination of status of a patient disease progression, finding the best ways to optimize a patient therapy, and the like. For example, the clinician 14 can define and/or use a pre-defined structured collection procedure 70 which looks at factors which may have an effect on the therapy of the patient. Such factors can include, for example, stress, menstrual cycle, pre-dawn effect, background insulin, exercise, bolus timing with respect to a meal, basal rate, insulin sensitivity, post-prandial behavior, and the like.

Figure 6E:
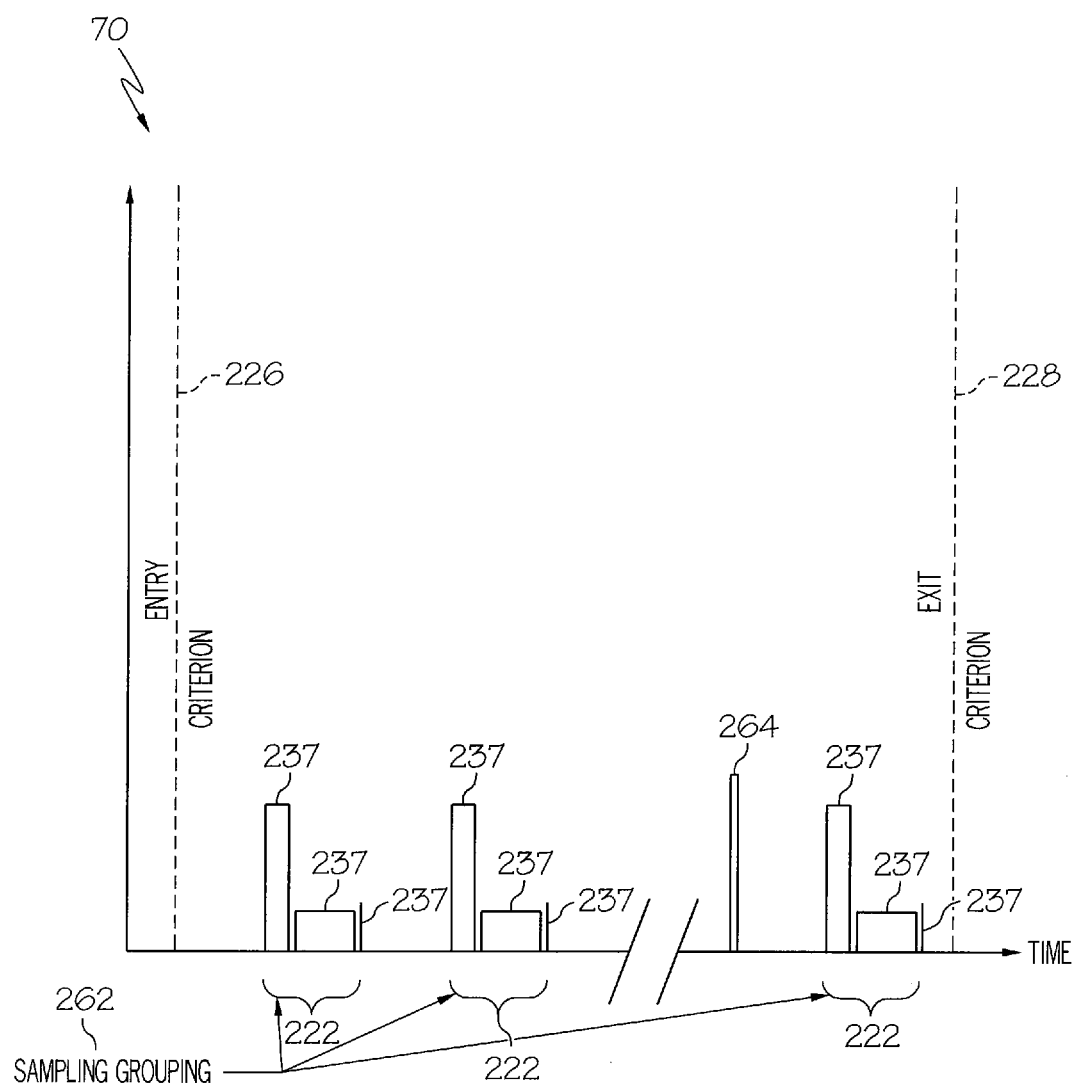

FIG. 6E shows a diagram structured collection procedure 70 comprising one or more multiple sampling groupings 262 each comprising a recurring schedule of collection events 222 provided between the entry criterion 226 and the exit criterion 228. In this example, the schedule of collection events 222 comprises one or more collection events 237 occurring each day at consistent times of day. As the structured collection procedure 70 in the process of obtaining contextualized biomarker data from a diabetic patient 12 can span over multiple days, even week and/or months before the exit criterion 228 is met, one or more checks 264, such as for parameter adjustment, and/or evaluation of whether to re-run the sampling groupings 262, can also be provided between the entry and exit criterions 226, 228 in one embodiment. The duration between such checks 264 can be used for physiological system equilibration, evaluation of treatment efficacy, or convenience. For example, either between each sample grouping 262, or after a predefined number such sampling grouping 262 (as shown), an analysis for the check 264 can be performed by the processor 102 to determine whether an adjustment to any parameter in the structured collection procedure 70 is needed.

For example, such analysis may be either for a parameter optimization or efficacy assessment. For the parameter optimization, the processor 102 can run calculations on the samples provided within a previous schedule of collection events 222 or sample grouping 262, using information from prior optimizations, clinician set parameters, and a collection or therapy strategy, recommends a new parameter value. For the efficacy assessment, the processor 102 can evaluate data not utilized by the optimization analysis. Additionally, it is to be appreciated that after a group of samples, i.e., sampling group 262, are taken the processor 102 can also evaluate the data from the sampling group 262, such as if such data is need in order to alter/optimize a person's therapy. Adherence criteria can be applied to the perform this evaluation to the data of the sampling group 262. For example, a first adherence criterion 224 can be used by the processor 102 to assess whether a minimum amount of data is provided by the sampling group 262 and if not, for example, the alteration/optimization of the patient's therapy will not take place. Another adherence criterion 224 could permit the processor 102 to assess whether the data is acceptable to permit an adjustment called for by the check 264, such as looking at spread of the data, whether there is too much variability (noise), as well as other data attributes to use the data. In this example, if meeting such adherence criterion, then the processor 102 has assessed that there is minimum risk that adjusting a parameter of the procedure could readily result in a severe event, e.g., hyper- or hypoglycemic event. Lastly, an adherence criterion can be used by the processor 102 to assess the exit criteria based on the data of sampling group, for example, the exit criterion is met when the data from the sampling group 262 satisfies the adherence criterion, such as for example, discussed above, for the sampling group.

It is to be appreciated that collection or therapy strategies can be categorized into scale based (sliding or fixed) assessments or formula based assessments. As input to the collection or therapy strategy, the processor 102 in one embodiment can utilize the data collected from a predetermined number of prior sample grouping(s) 262. This data can be either used as individual points (only the formula based collection or therapy strategies), or combined with filtering for use in a scale based assessment. In another embodiment, for example, the result of a check 264 performed by the processor 102 can also result in a status or recommendation being provided by the processor 102 automatically. Such status or recommendation may be e.g., a status of continuing with current parameter values, a recommendation to change particular parameters, a recommendation to change the adherence and/or exit criterion, a status that the processor 102 switched to a secondary adherence and/or exit criterion based on the analysis performed on the data from a prior schedule of events or prior sample grouping, or a recommendation to terminate the collection procedure, and the likes. A discussion of performing a structured testing method using a structured collection procedure according to an embodiment of the present invention is provided hereafter with reference made to FIG. 7A.

Structured Testing Method Using a Structured Collection Procedure

Figure 7A:
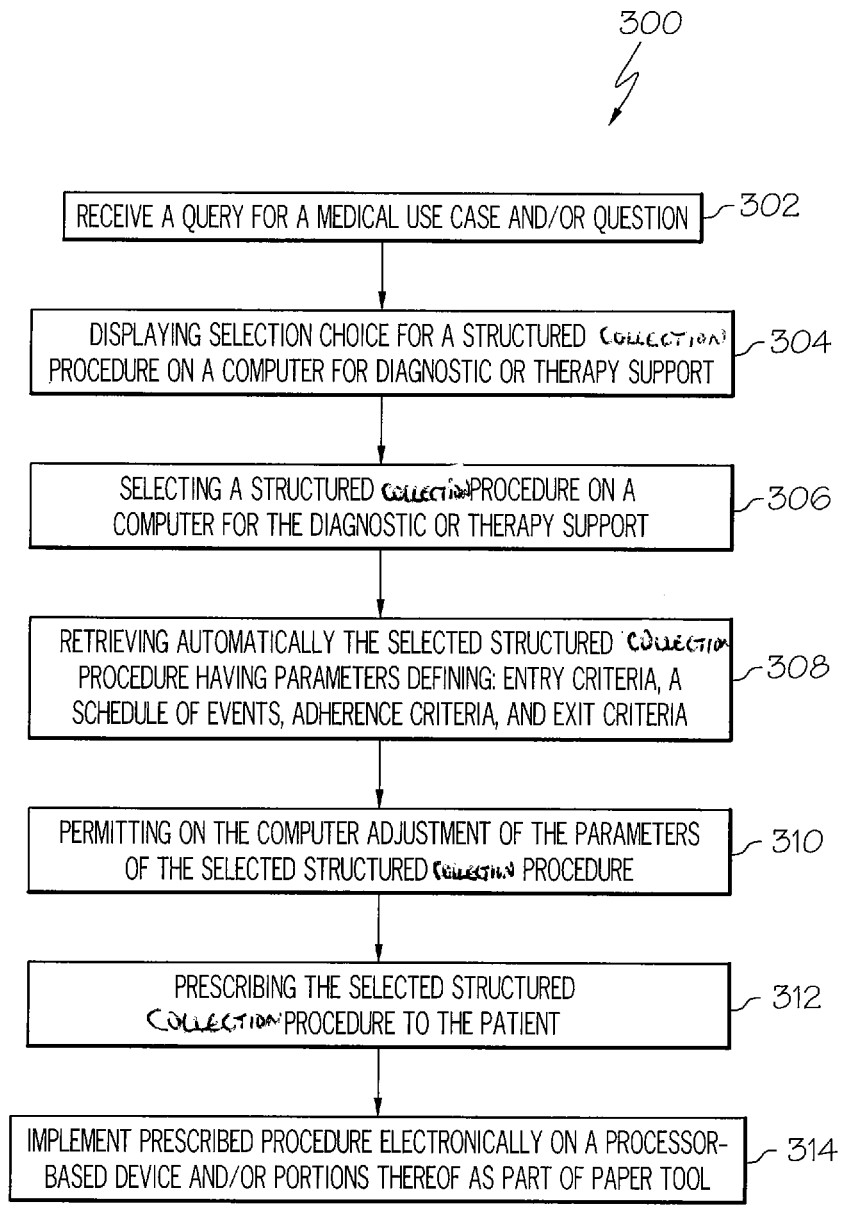
FIG. 7A depicts a structured collection procedure for diagnostic or therapy support of a patient with a chronic disease according to an embodiment of the present invention.

FIG. 7A depicts a structured testing method 300 for diagnostic or therapy support of a patient with a chronic disease through the use of a structured collection procedure. The method 300 may be implemented as instruction codes of a program running on a computer with a processor and memory, such as preferably clinician computers 25 (FIG. 2) as stand-alone software, as part of software 34, or as software provided as a service by server 52 via a secure web implementation over public network 50. Upon a processor 76 executing the program from memory 78 of the clinician computer 25, as one function among others, the processor 76 after receiving a query for a medical use case and/or question, searches memory 78, computer readable medium 40, and/or server 52 for all structured collection procedures 70a-d, which matches the submitted query in step 302. For example, the processor 76 may read the medical use case parameter 220 of each available structured collection procedures 70a-d and using a conventional search algorithm (e.g., list, tree, heuristics, etc.), provide on a display 82 a selection choice for those structured collection procedure matching the query in step 304 in one embodiment.

In one embodiment, the list displayed can reflect, for example, the structured collection procedures 70a, 70b, 70c, and 70d available for use from the server 52. In still another embodiment, the list of selection choices displayed can be dynamically created based on a type of medical use case the clinician 14 wishes to investigate. For example, prior to step 302, a list of selectable medical use cases can be displayed on the display 82 by the processor 76. In such an embodiment, the clinician 14, using the user interface device(s) 86 may selected from among the displayed medical use cases, for example, the medical use case "Determining meal effect on patient's therapy." After the clinician makes such a selection, which the processor 76 receives as input from the user interface device(s) 86, the processor 76 after using decision logic (e.g., if . . . then) provided by the software 34 would then display in step 304, for example, structured collection procedure 70b (e.g., a structured collection procedure to determine a more accurate insulin-to-carbohydrate ratio) and 70c (e.g., a structured collection procedure to determine bolus timing in regards to meal start), and not structured collection procedures 70a and 70d, which are structured collection procedures unrelated to the medical use case. Likewise, a "show all structured collection procedures" could also be a choice among the displayed medical use cases, in which the complete list of available structured collection procedures would then be displayed in step 304. In another embodiment, step 302 may be skipped and the processor 76 in step 304 can just provide a display of the structured collection procedures 70a-d available in memory 78 of the clinician computer 25.

In step 306, a clinician using the user interface devices 86 can select a structured collection procedure 70 on the clinician computer 25 for diagnostic or therapy support. For example, the selecting process can include choosing from the list displayed in step 304, which provided one or more structured collection procedures. After the clinician makes such a selection in step 306, which the processor 76 receives as input from the user interface device(s) 62, the processor 76 of the clinician computer 25 retrieves automatically from an electronic component, e.g., computer memory 78, server 52, or computer readable medium 40, and displays the selected structured collection procedure 70 on display 82 for viewing.

It is to be appreciated that each structured collection procedures 70a, 70b, 70c, and 70d is based on a medical use case and has parameters defining entry criteria 226, a schedule of collection events 222, adherence criteria 224, and exit criteria 228. As mentioned above, the entry criteria 226 establish the conditions needed to be met prior to obtaining biomarker data from the patient. Each collection event 237 of the schedule of collection events 222 comprises a performance time, patient guidance to perform the event, patient actions, a request for information from the patient, a request for collection of at least one type of biomarker data from the patient, and combinations thereof. The adherence criteria 224 is used to qualitatively assess whether a collection event 237 performed according to the schedule of collection events 222 provided data which is acceptable to addressing the medical use case upon which the structured collection procedure 70 is based. Additionally, as mentioned above, the exit criteria 228 establish the conditions needed to be met prior to exiting the structured collection procedure 70.

In step 310, after the processor 76 displays the selected structured collection procedure 70, the clinician 14, to meet the needs of the patient 12 and/or interests of the clinician, may adjust any one of the parameters 222, 224, 226, and 228 which are also displayed on the display 82. Safe guards may be implemented to ensure that only the clinician 14 can modify such parameters and/or run the software 34, such as via password protection. The processor 76 receives any such changes to the parameters 222, 224, 226, and 228 as input via user interface devices 86 and saves the revised structured collection procedure 70 in memory 78. Next, in step 312, the selected structured collection procedure 70 is prescribed on the clinician computer 25 to the patient 12 by the clinician 14, wherein the processor 76 of the clinician computer 25 provides as output the selected structured collection procedure 70 to the patient 12 to perform. For example, in step 314, the prescribed structured collection procedure 70 is implemented electronically on a processor based device, such as collection device 24, or any of the other above described devices 18, 28, and 36 (FIG. 1), as part of the software 34 or in other embodiment, portions thereof as part of paper tool 38.

In one embodiment, the prescribed structured collection procedure 70 may be implemented from the clinician computer 25 (FIG. 2) to the collection device 24 via communication link 72, via the public network 50 through a webpage and/or made available for downloading on server 52. In still other embodiments, the prescribed structured collection procedure 70 can be provided through the computer readable medium 40 and loaded by one of the devices 18, 24, 28, and 36, downloaded from another one of the devices 18, 24, 25, 26, 28, and 36, or downloaded via cell phone or telephone connection from server 52. Notice that a new/updated/prescribed structured collection procedure 70 available for use on the devices 18, 24, 25, 26, 28 and 36 may be provided in any standard fashion, such for via postal letters/cards, email, text messaging, tweets, and the likes. Reference hereafter is also made to FIG. 7B to further describe the features of the present invention.

Customizing a Structured Collection Procedure

FIG. 7B conceptually illustrates one example of a predefined structured collection procedure 70, which has a defined medical use case parameter 220 indicating that the procedure is helpful for medical use cases or questions which need to know the trends in blood glucose (bG) levels of a patient and/or the relationships between blood glucose values and time of day, meal size, and energy level. As mentioned above previously, the use case parameter 220 can be used as an identity tag in which the processor 102 may locate the associated structured collection procedure 70 in response to a search query, such as, for entered use case or question. For example, the search query can be entered into the collection device 24 via the user interface 146 and/or received from the clinician computer 25. Such a search query may result from a desire to know which uses case can be addressed by the structured collection procedures 70 currently available on the collection device 24, or to know which structured collection procedure 70 would be useful to address a particular use case or question. Therefore, the use case parameter 220 in one embodiment permits a structured collection procedure 70 to be automatically chosen by the processor 102 from a plurality of structured collection procedures 70a-d, such as provided in memory 110, memory 78, computer readable medium 40, and/or server 52 based on a selection, such as from a displayed list on the display 108 provided by the processor 102, or from input received by the processor 102 from the user interface of a defined medical question. In other embodiments, the use case parameter 220 may also indicate the structured collection procedure 70 is also useful for showing relationships between bG level values and time of day, meal size, and/or energy level.

In one embodiment, the pre-defined parameters of the structured collection procedure 70 can be displayed for modification/customization by the processor 102 of the collection device 24 on the display 108 and/or by the processor 76 of the clinician computer 25 on the display 82 by an authorized user. Such an authorized user may be identified, for example, on the collection device 24 and/or the clinician computer 25 by a password entered via the user interface device 146, 86, respectively. In such an embodiment, the pre-define parameters of structured collection procedure 70 can be displayed on the display 108, 82 in which customizable parameters can provide editable or selectable variables via drop-down boxes with various selection choices, radio buttons, check boxes, formatted fields requesting a specific type of information (mm-dd-yyyy, number, letter, etc.), text boxes to enter messages to be displayed, and the likes. The structured collection procedure 70 can be displayed for editing in tabular format (as illustrated) in one embodiment or in a sequential manner listing one parameter at a time in a scroll-through fashion in another embodiment. In still another embodiment, structured collection procedures can be provided which cannot be modified.

As shown by FIG. 7B, the structured collection procedure 70 may further comprise parameters defining one or more criteria setting the conditions needing to be met by the patient 12 to start of the structured collection procedure, i.e., entry criterion(s) 226, to end the structured collection procedure i.e., exit criterion(s) 228, and combinations thereof. In one embodiment, the processor 102 of the collection device 24 uses the one or more criteria to automatically start, evaluate, and end the structured collection procedure 70 if the condition(s) defined by the structured collection procedure are met. In still another embodiment, adherence criterion(s) 224, which are the conditions needing to be met in order for the collected datum/data to be accepted, can also be provided in the structured collection procedure 70.

As also shown in FIG. 7B, the structured collection procedure 70 further comprise parameters defining one or more collection events 237 which together form the schedule of collection events 222. Each of the collection events 237 comprises one or more requests 240, e.g., for a measurement from the measurement engine 138 of a biomarker value for a sample provided to the biosensor 140, and/or for information to be entered by the patient via the user interface 146 such as in response to a question presented by the processor 102 on the display 108. In the illustrated embodiment, the requests 240 are for a bG measurement, a meal size indication (S, M, or L), and an energy level indication (1, 2, 3, 4, 5), in which 1 is lowest and 5 is highest. Other such requests 240 can include indicating whether the patient exercised, indicating a particular food that was consumed, indicating which medicine was administered, indicating dosage of the medicine administered, and the like may also be provided in other structured collection procedures 70. In the illustrated embodiment, the collection events can be customized by selecting which request 240 the processor 102 should perform via a yes/no selection box.

The structured collection procedure 70 may also include guidance 230 and timing or performance time 238 associated with each of the collection events 237 as well as with each of the entry, exit, and adherence criterion/criteria 226, 228, and 224. Such guidance 230 is provided by the processor 102 to the display 108 upon the occurrence of the associated collection event 237 or other parameters. For example, a collection event 237 for a bG measurement before breakfast may also have a request 240 for an indication of the energy level of the patient. Therefore, in this example, the associated guidance 230 which states, "Please indicate energy level" is provided on the display 108 by the processor 102. It is to be appreciated that the guidance 230 is a text box, field, area, which enables for information to be provided to the patient to help the patient in performance of the structured collection procedure 70. In this example, selection of a number from 1 to 5 may be made via press of one of the buttons 147, 149 or via the touch screen interface if provided by display 108 as a data entry for such a request 240, which is then stored by the processor 102 in memory 110 of the collection device 24 as part of a data file 145 (FIG. 4) for the structured collection procedure 70.

The timing parameter 238 of the structured collection procedure 70 is used to specify for any one of the associated collection event 237, the entry, exit, and adherence criterion/criteria 226, 228, 224, either a specific date and/or time (mm-dd-yyyy, hh:mm), or a period (n) after a preceding collection event in which to perform the associated collection event. The periods $n_1$, $n_2$, $n_3$ in the illustrated embodiment for the respective collection events 237 indicate hours, but in other embodiments can be indicated in minutes or seconds. In another embodiment, the timing or performance time parameter 238 for an associated collection event 237 and for the entry, exit, and adherence criterion/criteria 226, 228, 224 can be modified by another collection event and/or by the criterion/criteria.

For example, in the illustrate embodiment, the entry criterion 226 is modified by the adherence criterion 224 by adding a day if the guidance 230 provided in the form of a question "Are you willing to conduct a test over 3 consecutive days?" is not affirmed by the patient 12 e.g., via a "No" selection provided on the collection device 24. In this illustrated example, the "Affirms guidance" may be a drop down selection provided in a combo box for customizing the adherence criterion 224 of the associated collection event 237, which when selected causes the processor 102 to wait for the accepted/not accepted input (e.g., via buttons 147, 149) before executing the remaining logic ("if not add 1 day to timing") of the adherence criterion 224. Still further in this example, the processor 102 in accordance with the logic provided in the adherence criterion 224 associated with the exit criterion 228, can set the timing or performance time parameter 238 of the exit criterion 228 to the date (mm-dd-yyyy) that is 3 days after completing the entry criterion 226. It is to be appreciated that the various possible combinations of logic statements which may be performed by the structured collection procedure 70 can be pre-defined and selected by a drop down box in order to be customized in one embodiment, and/or logic statements can be built in another embodiment.

Further details of the use of the entry, exit, and adherence criterion/criteria 226, 228, 224, respectively, are provided by U.S. patent application Ser. No. 12/643,338 filed Dec. 21, 2009 entitled "Contextualized biomarker data for diabetes diagnostics and therapy support," and assigned to Roche Diagnostics Operations, Inc., which is hereby incorporated by reference.

The structured collection procedure 70 can also includes in one embodiment an options parameter 232 associated with each of the collection events 237 as well as with each of the entry, exit, and adherence criterion/criteria 226, 228, 224. The options parameter 232 can have a customizable value(s) to govern whether the data and/or results of the associated collection event 237 or any of the other parameters e.g., entry, exit, and adherence criterion/criteria 226, 228, 224, in the structured collection procedure 70 meets a particular condition such that still further processing may be carried out by the processor 102 if such a condition(s) is meet. For example, such options can be to have the processor 102 automatically send a message to the clinician indicating that the patient has started the structured collection procedure 70 via satisfying the entry criterion 226, or to provide a message to the patient and/or the clinician if the patient fails a collection event 237 by not satisfying an adherence criterion, or to provide a message to the clinician when the patient completes the structured collection procedure 70 when the exit criterion is satisfied, or combinations thereof. For example, such an options parameter 232 can have a global list of such actions which is selected on the display 108, for example, by a selected value from a range of values associated with each option. For example, the options for each parameter can be customized via selecting from a drop down box having option choices (e.g., 1, 2, 3, 4, 5, . . . , A, B, C, etc.). In the illustrated embodiment depicted by FIG. 7B, for example, having Option 1 provided in the options parameter 232 of the collection procedure 70 will cause the processor 102 to provide a message to the clinician if the patient fails the associated "Before Breakfast" collection event 237, i.e., by not satisfying the adherence criterion 224. In still another embodiment, Option 2 can be a message which provides the patient positive reinforcement for successfully completing a collection event 237 e.g., "Good Job!," which the processor 102 automatically displays to the patient 12 on the display 106 of the collection device 24 when the associated adherence criterion 224 is satisfied. Likewise, in still another embodiment, Option 3 can be a message which provides negative reinforcement if the collection event 237 is not successfully completed, which the processor 102 automatically displays to the patient 12 on the display 106 of the collection device 24 when the associated adherence criterion 224 is not satisfied.

In another embodiment, the structured collection procedure 70 can also include a view flag parameter 239 associated with each of the collection events 222 as well as with each of the entry, exit, and adherence criterion/criteria 226, 228, 224 and checks 264 (if viewable data is generated and record by the processor 102 in an associated data record 152 of the data file 145). It is to be appreciated that most clinicians 14 rely on data to perform physiological assessment, therapy selection, therapy optimization, and therapy monitoring. Such data typically is a combination of clinical laboratory data, ambulatory or self-monitored data as well as findings discovered or measured by the clinician 14 during a clinical visit by the patient 12. The clinician's reliance on such data is based on the assumptions of data context, representativeness, completeness, accuracy, and precision.

Self-monitored data takes a prominent roll in the management of people with a chronic disease, such as diabetes. As clinical lab values such as HbA1c provide a metric for the 'average self care' provided over a minimum of a four week process, the metric does not provide information which is actionable by the person with diabetes, nor does the HbA1c provide information as to why the value is either good or bad. Spot/continuous bG monitoring coupled with a well documented log book of meals, exercise, stressors, and therapeutic administrations often provide the best source of information to the clinician 14.

It is to be appreciated that prior to the present invention, the typically manner of providing such self-monitored data by patients with diabetes to their clinicians is in the form of 'casual' data. Casual data is data collected under varying circumstances and for various reasons. Casual data presents itself as capricious values to the clinician—primarily due to lack of defined processes leading up to the measured values. Casual data requires the clinician to impute the datum circumstances from time of day. For example, the clinician would ascribe the first datum of the day as a fasting sample, providing it was in the morning. Some improvements have been made in the art, such as for example, permitting the patient 12 to mark such casual data—either manually with 'fasting', 'pre-dinner', 'post-dinner' markers and the like, or automatically by a timestamp. By doing so, the clinician no longer had to impute the datum circumstances. However, before the various embodiments of present invention, the coupling of what the clinician required for differential diagnosis to what the patient 12 provided at time of service had not been addressed successfully in the art. Historically, the clinician 14 was required to tease patterns from the data, and speculate on causal agents e.g., by looking at a table of data, and trying to identify whether each interval within a day is adequately managed.

To address the above noted issues, embodiments of the present invention provide further capabilities to the structured collection procedure 70 described previously above which leverage the advantages presented by such a procedure. Some of the noted advantages of the structured collection procedure 70, and not to be limited thereto, are that: the steps necessary for the patient to produce reliable results are enforced within the system, which changes the identification of 'circumstances' of data points to 'context' of a data point; a method is provided which helps to ensure that an adequate quantity of contextualized data points to provide a representative data set are collected, which changes the data from casual—one which the physician must guess—to actionable; and permits therapy optimizations to be accomplished at the patient's home with little clinician oversight, and minimal additional risk to the patient.

It is to be appreciated that the structured collection procedures 70 can be further classified into two general classes—assessments and optimizations. Assessment procedures (mentioned previously above in an early section) generally are used to collect data that will later be assessed, analyzed, and actioned on by the clinician 14. Optimization procedures are used to adjust therapy parameters and the like, and function by collecting repeated samples under known conditions, then making adjustments to the parameters until an exit criteria is met. The Accu-Chek 360 View form, also mentioned previously above, is an example of an assessment procedure, which acquires three days of seven data points per day. The clinician 14 can then utilize such data from the form in order to assess how well the patient 12 is self managing their diabetes based on therapy prescriptions determined by the clinician.

It is further to be appreciated that through clinical trials, which used the Accu-Chek 360 View form, it was discovered that although the data showed a betterment of data values occurring on day 3 versus day 1, repeated measures of the same patients with the same tests showed regular regression after this day 3 trended toward better indications of self management. In other words, the patients were getting better through the use of the form, then going back to their old ways of self management. Accordingly, the data was not representative of the normal behavior of the patient.

Therefore, to address the above mentioned issue, the view flag parameter 239 associated with each of the collection events 222 as well as with each of the entry, exit, and adherence criterion/criteria 226, 228, 224 and checks 264 provided in an embodiment of the structured collection procedure 70 provides the clinician 14 with the opportunity to blind desired ones of the data point values as well as the associated contextualized data (e.g., the contextualized biomarker data) from the patient 12, i.e., the associated ones of the data records 152 in the data file 145. In this manner, the patient 12 would not have any information by which to adjust their behavior, while maintaining the safety of the user. Such an embodiment should lead to better, more representative data befitting of the patient's real lifestyle.

In one embodiment, the view flag parameter 239 has a viewable value and a non-viewable value, e.g., binary, character, etc. The view flag parameter 239 in the structured collection procedure 70 governs whether the data and results of the associated collection event 237 or any of the other parameters e.g., entry, exit, and adherence criterion/criteria 226, 228, 224, and checks 264, in the structured collection procedure 70 can by displayed on the display 108 by the processor 102. If the viewable value (e.g., "Yes") is set for the view flag parameter 239 in the structured collection procedure 70, then the data and results of the associated collection event 237 (or other parameters) may be displayed by the processor 102 in the display 108 and if the non-viewable value (e.g. "No" or <null>), then such data and results cannot be displayed by the processor 102 in the display 108. In one embodiment, the setting of each of the view flag parameters 239 is predetermined by the structured collection procedure 70 e.g., when authored by a third party, and which in another embodiment may be modified (edited) at the discretion of the clinician 14. For example, the clinician 14 can modify/edit any of the structured collection procedure 70 on the clinician computer 25, and/or on the collection device 24 e.g., by entering a password designating the clinician 14 as an authorized user having editing rights. In one embodiment, the clinician 14 is presented e.g., on clinician computer 25 and/or on collection device 24, with a selection menu showing each of the collection events and/or the documenting and interrelating conditions that (or will) surround the associated biomarker measurement(s) for contextualization, e.g., a listing of biomarker events listed by pre-prandial measurements events, post prandial measurement events, before bed events, etc., which permits the authorized user to select either the viewable value or non-viewable value for the view flag in order to designate which ones of the collection events 237 are either viewable or non-viewable. It is to be appreciated that in other embodiments, instead of listing each particular collection event 237 (and/or their associated context) in the structured collection procedure 70, other selection menus having globally selectable view parameter values based on the contextualization type of the collection event e.g., all collection events 237 before and/or after exercising, all collection events 237 before and/or after a meal type and size, all collection events 237 before and/or after an amount of sleep, all collection events 237 before and/or after a specific time, date-time, etc., can also be provided.

It is to be appreciated that the patient 12 is still provided with the necessary data for managing their condition. For example, in the case of a patient with diabetes, key data points used to adjust insulin dosages would, by default, always be presented to the patient 12 on the display 108 by the processor 102. By default, it is meant that special case conditions—those requiring immediate action by the user—such as hypoglycemic events (e.g., bG values below 70 mg/dl), or severe hypoglycemic events (e.g., bG values below 56 mg/dl), or hyperglycemic events (e.g., bG values greater than 450 mg/dl), would be presented to the patient on the display 108 by the processor regardless of the state of the view flag parameter 239.

In another embodiment, the view flag parameter 239 has value (e.g., "AC") which causes the processor 102 to check whether the data value collected according to the event 237 meets the adherence criteria 224, and if so will designated the data associated with the event 237 in the data file 145 as viewable. In still another embodiment, the view flag parameter 239 has value (e.g., "nAC") which causes the processor 102 to check, and designated in the data file 145 as viewable, the data value collected according to an event 237 which does not meet the adherence criteria 224.

It is to be appreciated that in one embodiment, not only during the execution of the structured collection procedure 70 would such flagged data be masked from the patient 12, but also upon completion of the procedure such flagged data would also be masked from review by the patient, i.e., neither via the display 108 nor on any computing system connected to the device e.g., patient computer 18 (such as via Smart Pix device, Accu-Chek 360 end user software, and the likes), without proper authorization. Typically, the clinician 14 will only have the proper authorization e.g., via a password and/or encryption, in order to gain access to such data in the data file 145. As passwording and/or encrypting a data file or portions thereof is well known to those skilled in the related art, for brevity no further discussion is provided.

In another embodiment, after completion of the structured collection procedure 70, the patient may, at the discretion of the clinician 14 (or author of the procedure), have data visibility. In another embodiment, any data created as part of a structured collection procedure 70 is prevented from deletion by the end user, thereby stopping the patient 12 from selectively presenting data to the clinician 14. An example in the context of patient 12 being diabetic is provided hereafter to further illustrate the above mentioned features of having a collection device 24 running the above mentioned structured collection procedure 70 according to the present invention.

A typical patient with Type 2 diabetes may measure his/her blood glucose once per day after waking up in the morning. At a routine office visit, the patient's HbA1C result is found to be elevated. The clinician recommends that the person goes through three days of intensified glucose monitoring, and selects the structured collection procedure which is useful for this purpose. The structured collection procedure 70 is then customized as discussed above such that during these three days the collection events 237 are defined with a number bG measurement requests 240 such that the patient can be requested by the processor 102 to measure his/her blood glucose before and two hours (e.g., $n_1=2$) after breakfast, before and two hours ($n_2=2$) after lunch, before and two hours ($n_3=2$) after supper, and at bedtime. Additionally, the patient 12 can be requested via other associated requests 240 for each collection event 237 to provide an assessment of the relative size of the ingested meals at the appropriate times as well as an indication how he/she feels with regard to energy level. In the illustrate embodiment of FIG. 7B, the processor 102 can request the indication of energy level with each collection event 237 and the assessment of the relative size of the ingested meals every other collection event 237 (i.e., after the meal). Furthermore, the clinician has provided a condition via adherence criterion 224 of having to perform the meal assessment within ±30 minutes of period (n) of the associated collection event 237 in order for such information to be useful in the assessment. Such information is useful to contextualize the collected data and for the analysis performed on the collected data.

Additionally, the clinician 14 would like to be notified when the patient has failed to complete the "before breakfast" collection event 237. Therefore, to facilitate the notification option, the clinician 14 customizes the structured collection procedure 70 by set the options parameter 232 associated with the "before breakfast" collection event, via a drop down box to "Send a message to the clinician if adherence criterion fails." All other collection events 237 have their associated options parameter 232 default to indicate that the processor 102 is not to take any additional action with regards to the options parameter.

Furthermore, since the clinician 14 would like to assess the patient's usual behavior to draw conclusions about the cause of the elevated HbA1C value, the clinician 14 does not want the patient 12 to change his/her behavior over these three days. Therefore, the collection device 24 (e.g., blood glucose meter 26) should only display test results that are taken according to the patient's usual testing habit. In this example, where the patient usually only measures directly after waking up, the collection device 24 should only display a test result taken according to the structured collection procedure 70 when the test time is close enough to the usual test time of the patient and no other test that has been taken on the current day could be interpreted as wake-up time measurement. Furthermore, the clinician 14 decides that positive and negative reinforcement may be needed at particular times.

To make the above assessment, the clinician 14 asks the patient 12 about his/her usual testing habit. In this example, the clinician 14 then customizes the structured collection procedure 70 by marking the view flag parameter 239 of the "Before breakfast" collection event 237 to indicated that such a result is okay for the processor 102 to display on the display 108, i.e., View flag 239 set to "Y" as depicted by FIG. 7B. However, for this particular example, the clinician 14 decided to have the next two collection events 237, i.e., "$n_1$ Hours After Breakfast" and "Before Lunch" as well as the "Before Dinner" and "Before Bed" collection events 237 to have their associated view flag parameter defaulted to indicate that they are not to be displayed by the processor 102, i.e., view flag 239 set to "N" as also depicted by FIG. 7B. Additionally, the clinician 14 further wants the "$n_2$ Hours after Lunch" collection event 237 to be conditionally viewable (i.e., displayable on the display 106 by the processor 102) only if the adherence criteria 224 associated therewith is satisfied i.e., the data value collected within ±30 minutes of $n_2$ event 237 and to provide a message for reasons of positive reinforcement in this example. To do this, the clinician 14 customized the collection procedure 70 by setting the view flag 239 associated with the "$n_2$ Hours after Lunch" collection event 237 to being conditionally viewable, i.e., view flag 239 set to "AC" and to provide the Option 2 message (e.g., a positive reinforcement message) as depicted by FIG. 7B. Finally, the collection procedure 70 was further customized by the clinician 14 to permit the data value collected for the "$n_3$ Hours after Dinner" collection event 237 to be displayable by the processor 102 only if the adherence criteria 224 associated therewith i.e., "±30 minutes of $n_3$" is not satisfied via setting the associated view flag 239 to "nAC" and to provide the Option 3 message (e.g., the negative reinforcement message) as depicted by FIG. 7B in this example. In still other embodiments, other combinations of messages and collected data that is viewable, not viewable, or being conditionally viewable can be provided in various collection procedures 70, either pre-defined and/or customized by the clinician 14 as desired via simply setting one of the above mentioned parameters of the options 232 and view flag 239 in the collection procedure 70 as described above. It is to be appreciated, and in still another embodiment, the patient 12 can choose at any time to take a measurement outside of the structured collection procedure 70 in which the results of such a measurement will be displayed by the processor 102 on the display 108 as usual.

It is to be appreciated that the above described features and arrangements illustrated embodiment of FIG. 7B, provides a simply and convenient interface and method for customizing a structured collection procedure, such as for parameter adjustments carried out in step 310 of method 300 previously discussed above in reference to FIG. 7A.

Implementing and Performing a Structured Collection Procedure

Figure 8A:
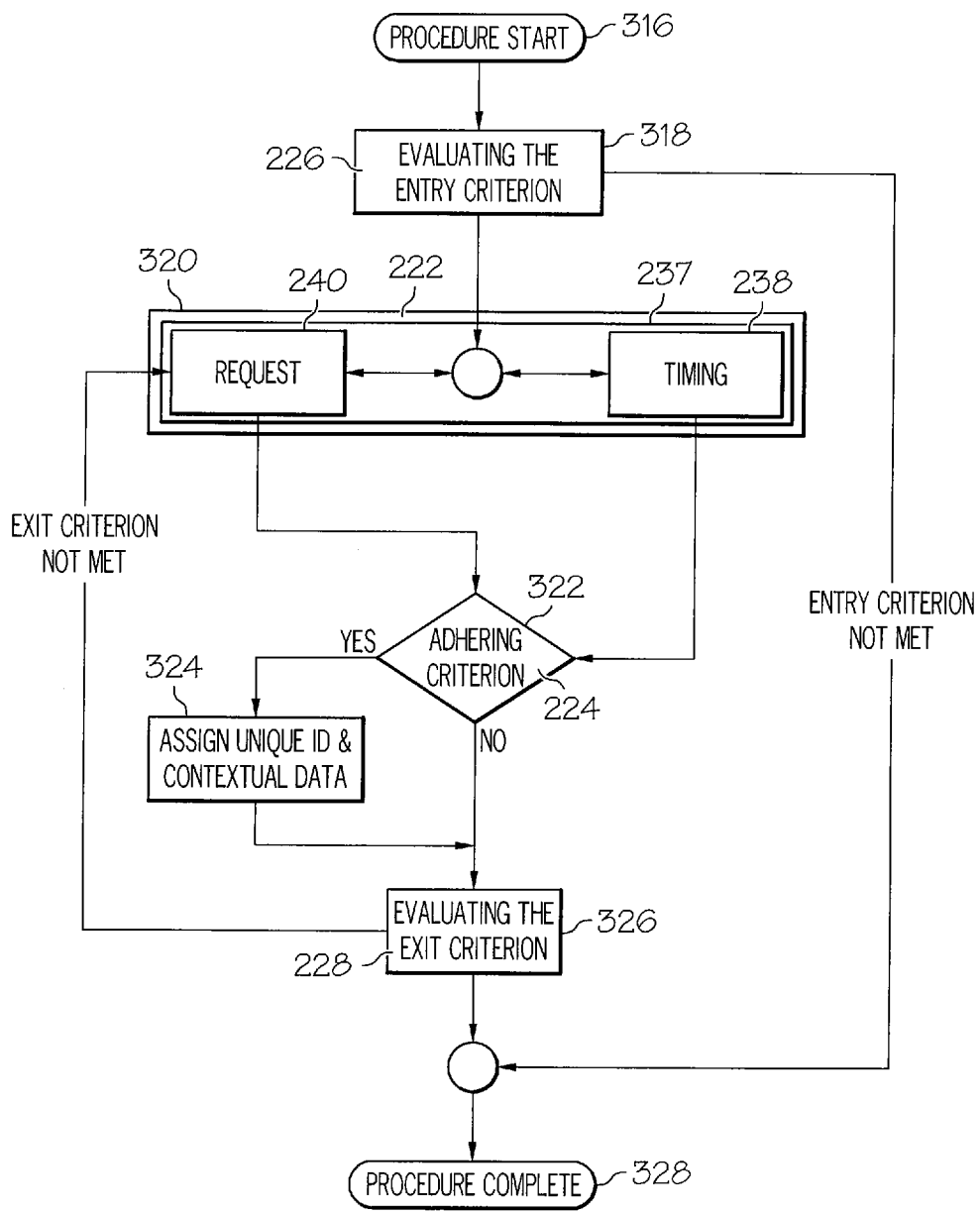
FIG. 8A shows a method for performing a structured collection procedure according to an embodiment of the present invention.

FIG. 8A shows a flowchart of the method for implementing and performing a structured collection procedure 70 to obtain contextualized biomarker data from a patient 12 according to an embodiment of the invention. It is to be appreciated that a number of structured collection procedures 70a-d (FIG. 2) prescribed in step 312 and implement in step 314 (FIG. 7A) may be stored in memory 110 (FIG. 3) of the collection device 24 and selected for execution at any desired time. For example, upon pressing a certain combination of the buttons 147, 149, the patient can select a desired structured collection procedures 70a-c and the date when to start a structured collection, i.e., a set mode function. For example, a date range to choose from may be to begin the testing tomorrow and end at today +90 days, which the processor 102 can also recorded in the data file 145 (FIG. 4) as part of the setup data 163. In such an implementation, the processor 102 as instructed by the software 34 reads the setup data 163 for the selected structured collection procedure 70 and indicates on the display 108 that the collection device 24 is in a structured testing mode, for example, from one day before the chosen start date until the end of the structured collection procedure.

It should be appreciated that multiple structured collection procedures 70a-d can be executed sequentially or simultaneously at any given time. However, in one embodiment, the software 34 permits the user only to schedule another structured collection procedure 70 if the start date is later than the end date of the current structured collection procedure 70 being executed. The software 34 also permits the user to override a scheduled date for a structured collection procedure 70. If a structured collection procedure 70 is scheduled and the user enters the set mode function again, the software 34 causes the processor 102 to display the scheduled date on the display 108 as the default date; if the user exits the set mode without modifying the date, the previously scheduled date stays active. If a structured collection procedure 70 has started, the software 34 permits the user to enter the set mode and cause the processor 102 to cancel the current structured collection procedure 70. Upon cancellation, in one embodiment, the software 34 causes the processor 102 to de-tag (e.g., null the unique identifiers 167) the data records 152 in the data file 145 for the data collected for the cancelled structured collection procedure 70.

Upon reaching the procedure start in step 316 (FIG. 8A), the processor 102 evaluates the whether entry criterion(s) 226 is met in step 318 to begin the structured collection procedure 70 selected to obtain biomarker data to address a predefined use case or question (e.g., use case parameter 220). In step 320, the processor 102 specifies requests 240 according to their associated timing 238 for each collection event 237 in the schedule of collection events 222 for the structured collection procedure 70. It is to be appreciated that the schedule of collection events 222 provides a sampling plan for biomarker data collection that is performed by the processor 102 to obtain biomarker data in a predefined context. In performing the schedule of collection events 222 in step 320, the software 34 causes the processor 102 to assign a unique identifier (e.g. incremental count) 167 in a date record 152 which corresponds to each collection event 237 in the structured collection procedure 70. Optionally, each criterion 226, 228, 224 may also be provide with a date time stamp 169 to indicate when such criterion was satisfied, if desired.

Adherence criterion 224 is then applied to the input received (e.g., biomarker data or information) in response to a request 240 to determine whether the input received meets the adherence criterion 224. When a structured collection procedure 70 has started, all data collected according to requests 240 in the structured collection procedure 70 and which satisfy the adherence criterion 224, if required in step 322, are then assigned (tagged) in the data file 145 by the processor 102 with the unique identifier 167 in step 324. It is to be appreciated that the unique identified also serves to associates the collected data e.g., data values 256 with their collection event 237, the request 240, and a date-time stamp 169 to indicate when the collection in response to the request 240 was received by the processor 102. While a structured collection procedure 70 is being executed, in one embodiment the software 34 permits the user to perform a measurement on the collection device 24 at any time without interfering with the episode and be able to view the measurement results on the display 108 (i.e., another special case condition).

In one embodiment, the software 34 permits reminders for biomarker measurements to be 'snoozed' as mentioned above for a period, such as for example, 15 minutes and up to a number of times, for non-critical measurements. In another embodiment, biomarker measurements or data entries that are performed close enough in time to a request 240 in step 320 are designed as valid measurements or data entry for the request 240 by the software 34. As such, the processor 102 will tag the associated data record 152 for the collection event 237 with the unique identifier 167 for such a biomarker measurement or data entry accordingly. In the case of biomarker measurements, if the measurement is accepted as valid for the request 240, the software 34 causes the processor 102 to prompt the user to input additional information if needed by the structured collection procedure 70 to provide context 252 for data resulting from the request 240. Such additional input, may include, for example, a rating of energy level from 1 to 5, where 1 is low and 5 is high; meal size from 1 to 5 where 1 is small and 5 is large, and exercises from yes or 1 to mean over 30 minutes, and no or 2 to mean less than 30 minutes. Such additional information or contextual information 156 when inputted via the user interface 146 is stored by the processor 102 in the data file 145 associated with the unique identifier 167 for the data event request 240 requiring the additional information also in step 324.

In one embodiment, biomarker measurements determined by the processor 102 as not being close enough in time to the data event request 240 defined by the structured collection procedure 70 will not be tagged with a unique identifier 167 in the data file 145 by the processor 102. Such is illustrated in the shown data file 145 with request 240d and data values 256d not being associated with a unique identifier 167 e.g., <null>. An example of a definition of 'close enough in time to the collection procedure' as instructed by the structured collection procedure 70 and/or software 34 to cause the processor 102 to make such a determination may be defined as being relative to a prescheduled time or a snoozed time. For example, for pre-prandial measurements up to 15 minutes in anticipation is acceptable; for post-prandial measurements, up to 10 minutes in anticipation is acceptable; and for bedtime measurements, up to 15 minutes in anticipation is acceptable. Other definitions may be provided in other structured collection procedures 70 and/or software 34.

In step 326, the processor 102 then evaluates whether the exit criterion 228 for the selected structured collection procedure 70 is satisfied. If not, then the processor 102 continues with performance the schedule of collection events 222 until the exit criterion 228 is satisfied. Upon satisfying the exit criterion 228, the structured collection procedure 70 ends in step 328. In one embodiment, the structured collection procedure 70 may also end if in step 318, the entry criterion 226 is also not met.

In some embodiments, the structured collection procedure 70 can be configured for performance as a paper tool 38; diabetes software 34 integrated into a collection device 24 such as a blood glucose meter 26; diabetes software 34 integrated into the computing device 36, such as a personal digital assistant, handheld computer, or mobile phone; diabetes software 34 integrated into a device reader 22 coupled to a computer; diabetes software 34 operating on a computers 18 and/or 25, such as a personal computer; and diabetes software 34 accessed remotely through the internet, such as from a server 52. When diabetes software 34 is integrated into a collection device 24 or a computing device 36, the diabetes software 34 can prompt the patient to record diary information such as meal characteristics, exercise, and energy levels. The diabetes software 34 can also prompt the patient to obtain biomarker values such a blood glucose values.

GUI Interface Providing a Selectable Structured Collection Procedure

Figure 8B:
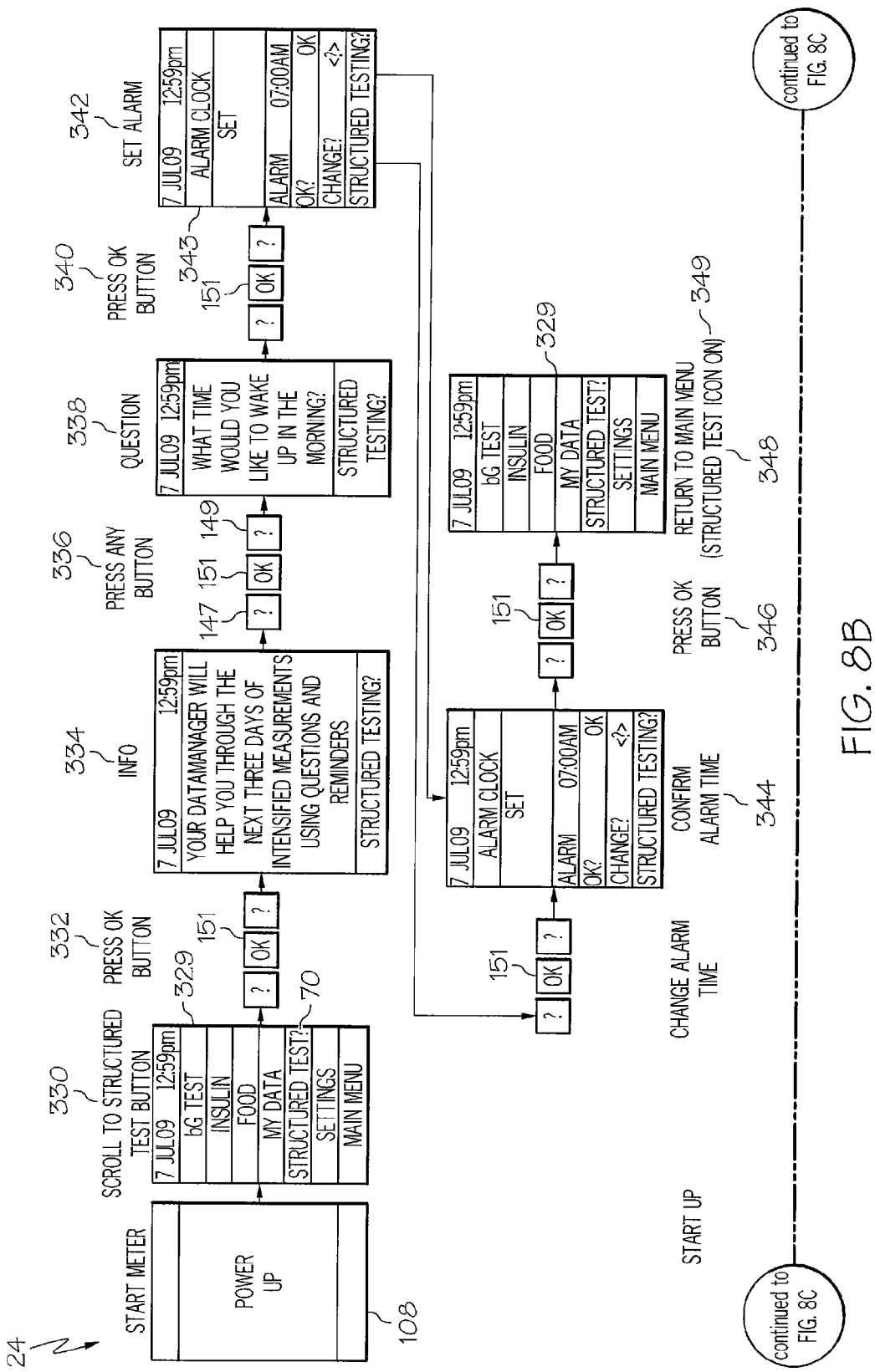

FIG. 8B shows a method of implementing the structured collection procedure via a graphical user interface provided on a collection device 24, which when executed on the collection device, cause the processor 102 to perform the following steps. Upon pressing a certain combination of the buttons 147, 149, the patient 12 can scroll to the structured collection procedure 70 available for selection in a list 329 provided by the processor 102 on the display 108 of the collection device 24 in step 330. If desiring to start the structured collection procedure, the patient 12, for example, selects via pressing an OK button 151 in step 332, the desired structured collection procedure 70. In this example, the entry criteria 226 (FIG. 6) of the structured collection procedure 70 provides information in step 334 which the processor 102 displays to the user on the display 108. After reading the displayed information, the user presses any button in step 336 in which the next procedure in the entry criteria 226 is performed by the processor 102. In this illustrated example, as part of the entry criteria 226, a question is then asked in step 338 by the processor 102. If the patient 12 is still desirous of starting the structured collection procedure, the patient 12 selects the OK button 151 in step 340; otherwise, any other press via button 147, 149 will cause the processor to go back to the list 329, thereby stopping the set-up procedure for the structured collection procedure 70.

After the patient 12 presses the OK button 151, the processor 102 in step 342 will provide on the display 108 an alarm clock 343 for setting the time to begin the selected structured collection procedure 70. It is to be appreciated that all the required collection events 237 for biomarker sampling, patient information, etc., is automatically schedule by the processor 102 in accordance with the schedule of collection events 222 for the structured collection procedure 70 in which timing, values, questions, viewable fields, viewable data, etc., therein may have been adjusted by the clinician 14 as discussed previously above in reference to FIGS. 7A and 7B. Therefore, other than entering the start time as permitted by the entry criteria 226, no other parameter adjustments in the structured collection procedure 70 is required by the patient 12 (or permitted in one embodiment).

In the illustrated embodiment, the patient in step 344 can adjust the start time of the structured collection procedure for the next day, e.g., Day 1, via buttons 147, 149. Upon confirming the start time in step 346 via pressing the OK button 151, the start time is recorded in memory 110 as part of the setup data 163 in the data file 145 (FIG. 4) for the structured collection procedure 70 by the processor 102. The processor 102 then displays the selection list 329 on the display 108 in step 348, thereby completing the set-up procedure, which satisfies the entry criterion 226, and indicates on the display 108 that the collection device 24 is in a structured testing mode 349.

It should be appreciated that in one embodiment multiple structured collection procedures can be executed sequentially or simultaneously at any given time, and hence in one embodiment the mode 349 provided on the display 108 will indicated which structured testing is being performed. However, in one preferred embodiment, the software 34 does not permits the user to schedule another structured collection procedure, unless the start date is later than the end date of the current structured collection procedure being executed via the user interface 146. It is to be appreciated that processor 102 may re-schedule the following structured collection procedures automatically if the current structured collection procedure is still running due to the exit criteria 228 not being met. The software 34 in another embodiment may also permit the user to override a scheduled date for a structured collection procedure. If a structured collection procedure is scheduled and the user enters the set mode function again, the software 34 causes the processor 102 to display the scheduled date on the display 108 as the default date; if the user exits the set mode without modifying the date, the previously scheduled date stays active. If a structured collection procedure has started, the software 34 permits the user to enter the set mode and cause the processor 102 to cancel the current structured collection procedure, if desired.

In step 350, an alarm condition 351 can be provided by the processor 102 the next day (as indicated by the symbol Day1) as was set in the above-mentioned procedure the previous day (as indicted by the symbol Start Up). Upon the user selecting any button 147, 149, 151 in step 352, the processor 102 as instructed by schedule of collection events 222, provides a first scheduled collection event 237 which is information 353 to be displayed on display 108 in step 354, which the patient 12 acknowledges with any button 147, 149, 151 being pressed in step 356. Next in step 358, the processor 102 is instructed by the schedule of collection events 222 to execute a second scheduled event, which is to display on the display 108 a question 359 for the patient, which the patient 12 acknowledges with any button 147, 149, 151 pressed in step 360. In the illustrated embodiment, the patient in step 362 indicates the start time of breakfast in minutes from the wake up alarm 351 previously acknowledged in step 352. Upon confirming the meal start time in step 364 to the processor 102, via pressing the OK button 151, the meal start time is recorded in memory 110. For example, the meal start time is recorded in the data file 144 in the associated data record 152 as data for the collection event 237 by the processor 102. Additionally, in step 366, the processor 102 displays to the patient 12 the information regarding the timing for the next schedule event as a reminder. In step 368, upon reaching the next scheduled event indicted by the schedule of collection events 222, the processor 102 provides a request 240 on the display 108 for the patient to take a measurement, e.g., a blood glucose measurement. Additionally, in step 370, the processor 102 also makes a request 240 for information on the size of the meal that is to be ingested as required by the schedule of collection events 222 in order to provide contextual information 156 to the measurement value.

As mentioned above previously, for each event the software 34 causes the processor 102 to assign a unique identifier (e.g. incremental count) 167 (FIG. 4) to the data of each request 240 provided in the schedule of collection events 222 which meet the adherence criterion 224 in the associated date record 152 for the collection event 237. Therefore, while the structured collection procedure 70 is being executed, the software 34 permits the user to perform a measurement on the collection device 24 at any time out side the schedule of collection events 222. Such a measurement since not being performed according to a request 240 will not be evaluated for the adherence criterion 224, and thus will not be provided with a unique identifier 167 in the date file but will only be provided with a date-time stamp and its measurement value. Such data is still recorded in the data file 145, as such data may still be useful for another analysis.

Figure 8C:
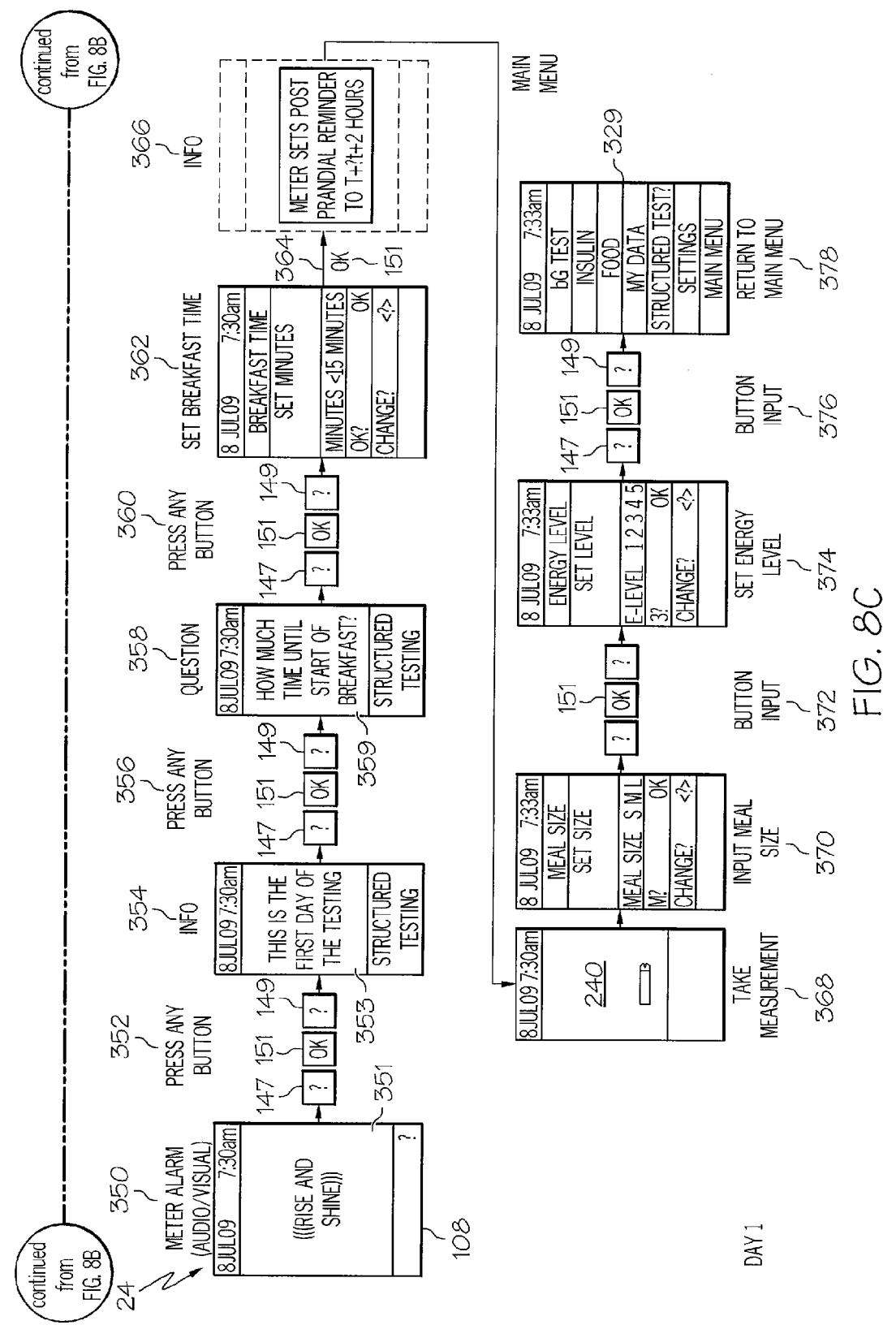

In another embodiment, the software 34 also permits reminders for biomarker measurements, such as provided in step 368 (FIG. 8C). For example, in one embodiment, the processor 102 provides an alarm and/or alert message for a reminder via the indicator 148 and/or on the display 108, respectively, to provide a measurement. For example, at the time 238 of a particular request 240 for taking a biomarker measurement (or reading), the processor 102 prompts the patient 12 by at least displaying on the display the message, "It is now time for your reading." An audible alarm and/or tactile alarm (vibrations) can be provided by the processor 102 via indicator 148 in another embodiment. For example, in one embodiment, the collection device 24 will provide such a prompt even when already powered on, such as by the patient 12 for another reason, e.g., to conduct a non-scheduled event, when in, for example, a window of time in which to take the requested measurement/reading, or even when powered downed, such as in a standby mode, by waking up to provide the reminder via the prompt. In another embodiment, the provided reminder or prompt can be 'snoozed' for a pre-defined period as mentioned above, that still falls within the window of time in which to take the requested (critical) measurement/reading such as for example, 15 minutes or any other such suitable time that falls in the window of time. It is to be appreciated that the snooze feature for a measurement/reading that is considered critical to the structured collection procedure 70, e.g., a measurement/reading needed for helping to address the medical use case or question, needed to meet adherence criteria 224, and/or needed in subsequent analysis for some determination, etc., the snooze feature will not extend the request 240 beyond the window of time provided by the structured collection procedure 70 via, e.g., adherence criterion 224 for the request 240. For example, in one embodiment one or more collection events 237 in the schedule of collection events 222 can be pre-defined as critical as well as being a primary sample via use of the options parameter 232 (FIG. 7B) provided in the structured collection procedure 70. For example, a collection event 237 which is designated as critical is one that cannot be missed, but if missed can be replaced by another sample already in the date file 145. A collection event 237 which is designated as a primary sample is one that cannot be missed, and which cannot be replaced by another sample, even if available in the date file 145. In still another embodiment, the snoozing can be up to a number of times, for non-critical measurements. For example, certain collection events 237 in the structured collection procedure 70 could be designated as having a non-critical request 240, which can be snoozed, such as via selecting such an option that is provided as one of the options parameter 232 (FIG. 7B). The options parameter 232 in this embodiment could for example provide the snooze option as well as a selectable time interval (e.g., 1-60 minutes, etc.) and a selectable number of times (e.g., 1-5, etc.) that the user is permitted to snooze the request 240. In still another embodiment, the collection device 24 permits for an alarm shut off i.e., the indicator 148 if providing the reminder (audible, vibratory) can be shut off for the entire window of time via the user interface 146, but wherein processor 102 still accepts the measurement/reading as long as it is made in the window of time.

In still another embodiment, the collection device 24 provides a skip reading option also received by the processor 102 via a selection entered using the user interface 146, e.g., from a list of selectable options, such as for example, snooze, alarm shut off, skip reading, provided on the display 108, in which again no reminder/prompt will be provided as patient 12 has indicated to the processor 102 that he/she does not want to take that particular requested measurement/reading. It is to be appreciated that selecting the skip reading selection option can result in an adherence event 242 resulting in further processing, such as discussed previously above in early sections, if adherence criterion 224 had been associated with the collection event 237 prompting the request 240.

In still another embodiment, the adherence criteria 224 can require biomarker measurements to be performed close enough in time to a data event request 240. Therefore, if such biomarker measurements are performed within the period specified by the adherence criteria 224, the processor 102 can indicate that the measurements or data entry for the event is acceptable and tags (i.e., assigns the unique identifier 167) the value of the biomarker measurement or data entry in the data file 145 accordingly. In the case of biomarker measurements, if the measurement is accepted as valid for the data event request 240 (i.e., meets the adherence criterion(s) 224), the schedule of collection events 222 may causes the processor 102 to prompt the user to input additional information if needed by the structured collection procedure 70, such as mentioned above regarding step 370 to provide contextual information 156 (i.e., context) to the measurement received in response to a request 240.

Such contextual information 156 when inputted via the user interface 146 can be stored by the processor 102 in the data file 145 associated with the unique identifier 167 for the data event request 240 requiring the additional information. Biomarker measurements determined by the processor 102 as not being close enough in time to the data event request 240 as defined by the adherence criteria 224 will not be tagged in the data file 145 by the processor 102. Such is illustrated in the shown data file 145 (FIG. 4) with data event request 240d and data values 256d not being associated with a unique identifier 167. An example of a definition of 'close enough in time to the collection procedure' as instructed by the adherence criteria 224 to cause the processor 102 to make such a determination may be defined as being relative to a prescheduled time or a snoozed time. For example, for pre-prandial measurements up to 15 minutes in anticipation is acceptable; for post-prandial measurements, up to 10 minutes in anticipation is acceptable; and for bedtime measurements, up to 15 minutes in anticipation is acceptable. Other definitions may be provided in other adherence criteria 224 for other events in the schedule of collection events 222 as well as in other structured collection procedure.

Figure 9:
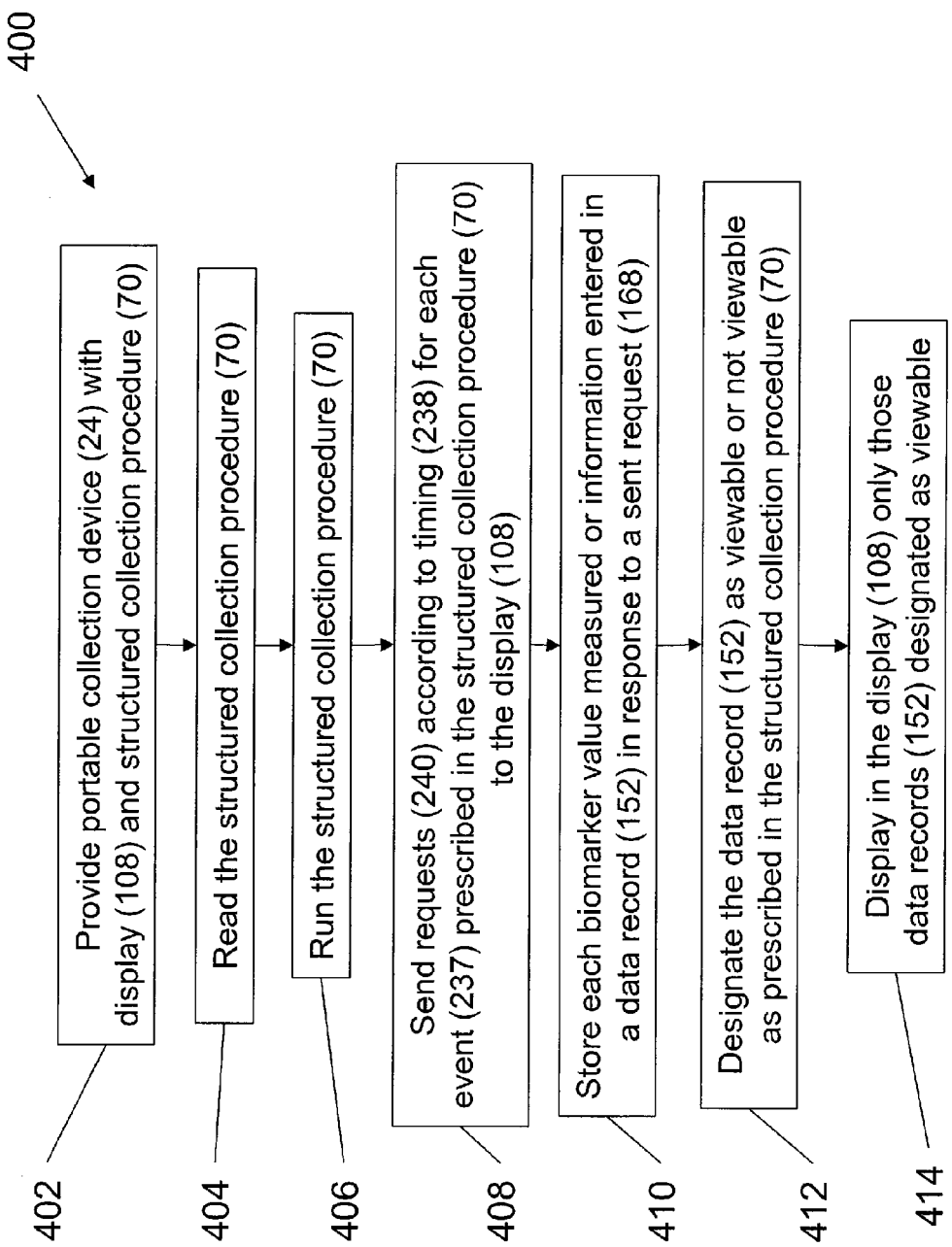
FIG. 9 depicts a flow diagram depicting a testing method according to an embodiment of the present invention.

In the illustrated embodiment, the user uses the buttons 147, 149 to scroll to a selection, which is entered by the processor in the data record 152 for the associated request 240 via pressing Okay button 151 in step 372. In one embodiment, the meal size can be indicated via a number range, such as for example, from 1 to 5, where 1 is small and 5 is large. In the illustrated embodiment, additional input for contextual information 156 regarding a rating of energy level from 1 to 5, where 1 is low and 5 is high is requested in step 374, which is entered in the data file 145 as mentioned previously above via the processor 102 receiving input for the request 240 by using the user interface 146 in step 376. In other embodiment, other contextual information 156 may include indicating whether the patient exercised and/or how long. For example, the user interface 146 may be use in which yes or 1 to mean over 30 minutes, and no or 2 to mean less than 30 minutes. In the illustrated embodiment, as the exit criterion 228 is now meet via successfully performing steps 368-376, the structured collection procedure 70 ends in step 378, wherein the processor 102 again displays the list 329, such that the patient 12 may perform other tasks on the collection device 24, if so desired. Reference is now made to FIG. 9 hereafter to discuss the selective display method according to an embodiment of the present invention. It is to be appreciated that one or more of the method steps discussed hereafter can be provided as computer instructions stored on a computer readable medium that, when executed by a computer, cause the computer to perform one or more of the methods.

Method Example

With reference to FIG. 9, in the illustrated method 400, a portable collection device 24 (FIG. 3) is provided in step 402 which comprises a display 108, a user interface 146, a measurement engine 138 to measure a biomarker value, and memory 110 containing the data file 145 and a structured collection procedure 70 (FIG. 7B). The structured collection procedure 70 has parameters defining one or more collection events 222, timing 238 for the collection events, and a view flag parameter 239 associated with each of the collection events. The view flag parameter 239 has a viewable value and a non-viewable value, and each collection event 237 comprises one or more requests 240 for a measurement of the biomarker value and/or information. The collection device 24 further comprises a processor 102 connected to the display 108, the user interface 146, the measurement engine 138, and the memory 110 as well as power supply 150 for powering the collection device 24. Software 34 is also provided on the collection device 24 which has instructions that when executed by the processor 102 causes the processor to perform the following processing steps. In step 404, the processor 102 reads the structured collection procedure 70 from memory 110, and runs the structured collection procedure in step 406. In step 408, the processor 102 sends the requests 240 to the display 108 for the measurement of the biomarker value and/or for the information according to the timing 238 of each of the collection events 237 prescribed in the structured collection procedure 70. In step 410, the processor 102 stores each biomarker value measured by the measurement engine 138 or information entered via the user interface 146 in an associated data record 152 in the data file 145 (FIG. 4) in response to a sent request 240, stores and links automatically contextual information associated with each biomarker value or the information entered in the associated data record 152 of the data file 145 to form contextualized biomarker data, and designates the associated data record 152 containing the contextualized biomarker data as viewable if the view flag parameter 239 (FIG. 7B) provided for the associated collection event 237 has the viewable value (e.g., Yes) or as not viewable if the view flag has the non-viewable value (e.g., No or <null>) in step 412. In one embodiment, the default condition is not viewable wherein the processor 102 makes the data record 152 containing the contextualized biomarker data viewable as prescribed in the structured collection procedure 70 for each collection event 237 or vice versa in another embodiment. Finally, in step 414, the processor 102 provides to the display 108 only those data records 152 containing the contextualized biomarker data designated in the memory 110 as viewable. In another embodiment, the processor 102 will only provide to the display 108 the biomarker value measured by the measurement engine 138 per the sent request 240 if the view flag parameter 239 provided in the associated collection event 237 has the viewable value (e.g., Yes).

By the above disclosure, various embodiments of the present invention have been presented. For example, in one embodiment, the portable collection device is a blood glucose meter. In another embodiment, the structured collection procedure 70 is provided predefined in memory 110 of the collection device 24. In another embodiment, the portable collection device 24 further comprises a communication module 124, wherein the structured collection procedure 70 is programmed externally and received by the processor 102 from an external device 132 (e.g., devices 18, 25, or 52) via the communications module and stored into memory 110 by the processor 102. In still another embodiment, the structured collection procedure 70 is received via I/R communications between the processor 102 and the external device 132. In still another embodiment, the structured collection procedure 70 is stored into memory 110 of the collection device 24 via network-based communications between the processor 102 and the external device 132. In still another embodiment, the network-based communications is one of wireless and wired communications. In still another embodiment, the collection device 24 further comprises an interface connector 116, wherein the processor 102 receives the structured collection procedure 70 via a removable storage unit 120 connected to the interface connector 116, and in which the removable storage unit 120 contains the structured collection procedure 70. In still another embodiment, the processor 102 downloads the structured collection procedure 70 from the external device 132.

In still another embodiment, the structured collection procedure 70 programmatically spans multiple days. In still another embodiment, the portable collection device 24 contains in memory 110 various structured collection procedures 70 each having a different use case parameter 220 (FIG. 5B), which can be recorded in the data file 145 in an associated use case field 158 (FIG. 3) to associate such use case with the generated data records 152 (FIG. 4). In one embodiment, one of the various structured collection procedures 70 is selected through the user interface 146 for execution by the processor 102. In another embodiment, one of the various structured collection procedures 70 is selected remotely by an authorized device 134 for execution by the processor 102. In still another embodiment, the any biomarker value measured by the measurement engine 138 not in response to a sent request 240 of the structured collection procedure 70 is viewable on the display 108.

In still another embodiment, the user interface 146 and the display 108 are provided as a touch screen. In still another embodiment, the user interface 146 comprises user-operated buttons 147, 149. In still another embodiment, the processor 102 implements the structured collection procedure 70 when invoked by input received via the user interface 146.

In still another embodiment, the collection device 24 further comprises a communication module 124, and the processor 102 implements the structured collection procedure 70 when invoke by input received from the communication module 124 from a remote device 132 having authorization to invoke the structured collection procedure 70. In still another embodiment, the request 240 comprises an indication of meal size, an indication of energy level, an indication of performing exercise, and combinations thereof.

In still another embodiment, the timing 238 indicates at least one of a specific date (mm-dd-yyyy), a specific time of day (nn:mm), and an amount of time (n) after a previous collection event 237. In still another embodiment, the collection events 222 are at least one of before breakfast, after breakfast, before lunch, after lunch, before dinner, after dinner, before bed, before exercising, after exercising, before receiving a drug, after receiving a drug, and combination thereof.

In still another embodiment, the processor 102 designates automatically the associated data record 152 containing the contextualized biomarker data as viewable if the view flag 239 provided in the structured collection procedure 70 for the collection event 237 has the viewable value by writing a flag (e.g., a binary value, a hex value, an alpha numeric symbol, etc.) to an associated flag field 159 (FIG. 4) in the data record 152 and as not viewable if the view flag has the non-viewable value by not writing the flag to the field in the associated data record. It is to be appreciated that in the embodiments where the view flag 239 is set to be conditional viewable, e.g., either parameter "AC" or "nAC" provided in the collection procedure 70 (FIG. 7B), the associated flag field 159 of the data file 145 will reflect the results of the checking automatically performed by the processor 102 to see if the associated adherence criteria 224 is satisfied or not as the case maybe. For example, if the adherence criteria 224 is not satisfied in the case of the associated collection event 237 having an "AC" designated view flag 239, then the associated data record 152 containing the contextualized biomarker data will reflect that the record is not viewable, i.e., not viewable flag "N" recorded by the processor 102 automatically in the associated flag field 159. On the other hand, if the adherence criteria 224 is satisfied in the case of the associated collection event 237 having an "AC" designated view flag 239, then the associated data record 152 containing the contextualized biomarker data will reflect that the record is viewable, i.e., viewable flag "Y" recorded by the processor 102 automatically in the associated flag field 159. Likewise, the opposite conditions are provided for by the "nAC" view flag 239, where if the adherence criteria 224 is not satisfied, then the processor 102 automatically makes the associated data record 152 containing the contextualized biomarker data viewable, i.e., viewable flag "Y", and on the other hand, not viewable, i.e., not viewable flag "N" recorded in the associated flag field 159, if the adherence criteria 224 is satisfied.

In still another embodiment, the software causes the processor 102 to permit an authorized user to select at least one (viewable) criterion under which a data record 152 of the data file 145 for the structured collection procedure 70 is designated as viewable. For example, in one embodiment, the viewable criterion selected for the biomarker values, that are collected according to the events 237, can be a threshold value, value(s) above and/or below a range, or values that fall within a range. In another embodiment, the viewable criterion can be selected from the contextualized data of such biomarker values, e.g., all morning biomarker values are viewable, all lunch biomarker values are viewable, all dinner biomarker values are viewable, all bedtime biomarker values are viewable, all pre-prandial biomarker values are viewable, all post-prandial biomarker values are viewable, and combinations thereof. In such embodiments, the software then causes the processor 102 to designate automatically the associated data record 152 (of the data file 145 in the memory 110) containing the contextualized biomarker data as viewable if either the view flag 239 associated with the sent request 237 in the structured collection procedure 70 (when being run) has the viewable value e.g., "Y" or the at least one viewable criterion is met and as not viewable if either the view flag 239 has the non-viewable value e.g., "N" or the at least one criterion is not met. In the above embodiments, the software causes the processor 102 to provide only those data (e.g., biomarker) values 256 associated to data records 152 of the data record 152 if the data records are designated (i.e., via the associated flag field 159) as viewable.

In still another embodiment, the data file 145 can be downloaded to a remote computer, e.g., clinician computer 25 having analysis software 29 in which to view and analyze all data records 152 contained in the data file 145.

In one embodiment of present invention, the collection device 24 is a blood glucose meter having a specialized mode of operation that may be invoked directly through the meter or remotely is disclosed. The glucose meter enables the assessment of certain aspects of a person's medical situation by providing built-in support for the automatic execution of a testing regime or structured collection procedure 70 defining measurement and a schedule of collection events 222 and maintaining the validity the executed structured collection procedure (protocol) by blinding the person to all or some of the test results.

In another embodiment, the patient 12 operates the collection device 24 to place the device in a specialized mode of operation which executes a (selected) structured collection procedure 70. In the specialized mode of operation, the collection device 24 interacts with the patient to support the execution of the structured collection procedure 70 that will enable later the analysis of the targeted medical use case situation. The structured collection procedure 70 may be pre-programmed in the collection device 24, programmed by a clinician 14 on the collection device 24 and/or the Clinician computer 25, and downloaded directly and/or from a server 52 via a network 50. In the specialized mode of operation, the structured collection procedure 70 allows the patient to view certain test results but not others. In a particular embodiment, the structured collection procedure 70 contains information about which of the test results may be viewed by the patient and which may not. This information may be solely protocol related but in another embodiment may also take into consideration the usual testing habits of the patient.

It is to be appreciated that embodiments of the present invention enhance existing software and/or hardware that acquires and processes blood glucose (bG) data. The embodiments of the invention can be directly incorporated into existing home glucose monitors, or used for the enhancement of software that retrieves and processes bG data, by introducing a method for monitoring a patient according to a desired structured collection procedure while preventing the patient from modifying his or her behavior based on collection results. The invention further relates to a computer program and product for implementing the above-mentioned method.

Having described the disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

What is claimed is:

1. A portable, handheld collection device for the management of diabetes comprising:
   a display;
   a user interface;
   a measurement engine to measure a biomarker value;
   a non-transitory memory containing a data file and a structured collection procedure, the structured collection procedure having parameters defining:
      a schedule of collection events having one or more collection events which provide a request for a measurement of the biomarker value under defined conditions which are related to the biomarker value as contextual information associated with the biomarker value, and
      a view flag associated with each of the one or more collection events, the view flag having a viewable value and a non-viewable value;
   a processor connected to the display, the user interface, the measurement engine, and the memory; and
   a power supply for powering the device;
   wherein the processor is programmed to:
      read the structured collection procedure from the memory,
      permit an authorized user to select at least one criterion under which a data record of the data file for the structured collection procedure is designated as viewable,
      run the structured collection procedure,
      send automatically the request of each of the one or more collection events according to the structured collection procedure,
      store automatically biomarker value(s) measured by the measurement engine or information entered via the user interface in an associated data record of the data file in the memory in response to sent request,
      store and link automatically contextual information associated with each biomarker value or the information entered in the associated data record of the data file to form contextualized biomarker data,
      designate automatically the associated data record in the memory containing the contextualized biomarker data as viewable if the view flag associated with the sent request in the structured collection procedure has the viewable value or the at least one criterion is met and as not viewable if the view flag has the non-viewable value or the at least one criterion is not met, and
      provide to the display only biomarker values associated to data records containing the contextualized biomarker data if the data records are designated in the memory as viewable.

2. The portable collection device according to claim 1, wherein the structured collection procedure further comprises entry criterion defining one or more conditions which when satisfied start the schedule of collection events, and exit criterion defining one or more conditions which when satisfied end the structured collection procedure, and wherein the software having instructions that when executed by the processor further causes the processor to run automatically the structured collection procedure when the entry criterion is satisfied, and end automatically the structured collection procedure when the exit criterion is satisfied.

3. The portable collection device according to claim 1, wherein the at least one viewable criterion is at least one of a threshold value for the biomarker value, value(s) above and/ or below a range, or values that fall within a range.

4. The portable collection device according to claim 1, wherein the at least one viewable criterion is selected from the contextualized data of the biomarker value.

5. The portable collection device according to claim 1, wherein the portable collection device is a blood glucose meter or a continuous glucose monitor.

6. The portable collection device according to claim 1, wherein the portable collection device further comprises a communications module, wherein the structured collection procedure is programmed externally and the processor receives the structured collection procedure from an external device via the communications module.

7. The portable collection device according to claim 6, wherein the structured collection procedure is received via I/R communications between the processor and the external device.

8. The portable collection device according to claim 6, wherein the structured collection procedure is received via network based communications between the processor and the external device.

9. The portable collection device according to claim 8, wherein the network based communications is one of wireless and wired communications.

10. The portable collection device according to claim 1, wherein the portable collection device further comprises an interface connector, and wherein the processor receives the structured collection procedure via a removable storage device connected to the interface connector, the removable storage device containing the structured collection procedure.

11. The portable collection device according to claim 1, wherein the processor downloads the structured collection procedure from an external device.

12. The portable collection device according to claim 1, wherein the structured collection procedure has parameters defining that the schedule of collection events spans multiple days.

13. The portable collection device according to claim 1, wherein the portable collection device contains in memory various structured collection procedures each defining a different structured collection procedure, and wherein one of the various structured collection procedures is selected through the user interface for execution by the processor.

14. The portable collection device according to claim 1, wherein the device contains in memory various structured collection procedures each defining a different structured collection procedure, and wherein one of the various structured collection procedures is selected remotely by an authorized device for execution by the processor.

15. The portable collection device according to claim 1, wherein the processor provides to the display any biomarker value measured by the measurement engine not in response to a sent request.

16. The portable collection device according to claim 1, wherein any biomarker value measured by the measurement engine which indicates a hypoglycemic or hyperglycemic condition is viewable on the display.

17. The portable collection device according to claim 1, wherein the user interface and the display are provided together as a touchscreen.

18. The portable collection device according to claim 1, wherein the user interface comprises user-operated buttons.

19. The portable collection device according to claim 1, wherein the processor implements the structured collection procedure when invoked through input received from the user interface.

20. The portable collection device according to claim 1, wherein the device further comprises a communication device, and the processor implements the structured collection procedure when invoked by input received from the communication device from a remote device having authorization to invoke the structured collection procedure.

21. The portable collection device according to claim 1, wherein the collection event further comprises a request for an indication of meal size, a request for an indication of energy level, a request for an indication of completion of prescribed exercise, and combinations thereof.

22. The portable collection device according to claim 1, wherein a timing indicates at least one of a specific date, a specific time of day, or an amount of time after a previous collection event.

23. The portable collection device according to claim 1, wherein the collection events are at least one of before breakfast, after breakfast, before lunch, after lunch, before dinner, after dinner, before bed, before exercising, after exercising, before receiving a drug, after receiving a drug, or combinations thereof.

24. The portable collection device according to claim 1, wherein the processor designates the contextualized biomarker data in the associated data record as viewable if the view flag provided in the structured collection procedure for the collection event has the viewable value by writing a flag to a field in the associated data record and as not viewable if the view flag has the non-viewable value by not writing the flag to the field in the associated data record.

25. The portable collection device according to claim 1, wherein the data file is downloaded to a remote computer having analysis software in which to view and analyze all data records contained in the data file.

26. The portable collection device according to claim 1, wherein the structured collection procedure further has a parameter defining one or more adherence criteria, and the view flag of the structured collection procedure further has a conditionally viewable value, and wherein the software has instructions that when executed by the processor causes the processor to use the one or more adherence criteria as a logical switch to decide whether the associated data record in the memory is viewable when the view flag associated with the sent request in the structured collection procedure has the conditionally viewable value.

27. The portable collection device according to claim 24, wherein the processor automatically designates the contextualized biomarker data in the associated data record in the memory as viewable when the view flag associated with the sent request in the structured collection procedure has the conditionally viewable value and the one or more adherence criteria is satisfied by the biomarker value measured by the measurement engine or the information entered via the user interface in response to the sent request.

28. The portable collection device according to claim 24, wherein the processor automatically designates the contextualized biomarker data in the associated data record in the memory as viewable when the view flag associated with the sent request in the structured collection procedure has the conditionally viewable value and the one or more adherence criteria is not satisfied by the biomarker value measured by the measurement engine or the information entered via the user interface in response to the sent request.

29. The portable collection device according to claim 24, wherein the structured collection procedure further has a parameter defining one or more options, and wherein the software has instructions that when executed by the processor further causes the processor to send a message when the one or more adherence criteria is satisfied by the biomarker value measured by the measurement engine or the information entered via the user interface in response to the sent request.

30. The portable collection device according to claim 24, wherein the structured collection procedure further has a parameter defining one or more options, and wherein the software has instructions that when executed by the processor further causes the processor to send a message when the one or more adherence criteria is not satisfied by the biomarker value measured by the measurement engine or the information entered via the user interface in response to the sent request.

31. The portable collection device according to claim 1, wherein the software has further instructions that when executed by the processor causes the processor to permit an authorized user to select which of the one or more collection events is assigned the viewable value or the non-viewable value of the view flag.

* * * * *